United States Patent
Brahmachari et al.

(10) Patent No.: US 7,363,166 B2
(45) Date of Patent: Apr. 22, 2008

(54) COMPUTATIONAL METHOD FOR THE IDENTIFICATION OF CANDIDATE PROTEINS USEFUL AS ANTI-INFECTIVES

(75) Inventors: Samir Kumar Brahmachari, Delhi (IN); Srinivasan Ramachandran, Delhi (IN); Tannistha Nandi, Delhi (IN); Chandrika Bhimarao, Delhi (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/820,843

(22) Filed: Mar. 30, 2001

(65) Prior Publication Data
US 2003/0039963 A1    Feb. 27, 2003

(51) Int. Cl.
*G06F 19/00*    (2006.01)

(52) U.S. Cl. .............................. 702/19; 702/30; 703/2; 707/6; 707/100

(58) Field of Classification Search .................. 702/19, 702/20; 530/350; 720/19, 20
See application file for complete search history.

*Primary Examiner*—Carolyn L. Smith
(74) *Attorney, Agent, or Firm*—Sughrue Mion, PLLC

(57) ABSTRACT

The present invention relates to a novel method for the identification of candidate proteins in pathogens useful as anti-infectives and more particularly, the present invention describes a novel computational method involving calculation of several sequence attributes and their subsequent analysis lead to the identification of some outlier proteins in different pathogens which are either vaccine candidates, diagnostics or drug targets and also are provided the genes encoding the candidate proteins.

8 Claims, 1 Drawing Sheet

*M.tuberculosis*

$D_{fixed}/L$ vs %hydrophobicity

FIGURE 1

COMPUTATIONAL METHOD FOR THE IDENTIFICATION OF CANDIDATE PROTEINS USEFUL AS ANTI-INFECTIVES

FIELD OF INVENTION

The present invention provides a novel method for the identification of candidate proteins in pathogens useful as anti-infectives. More particularly, the present invention relates to candidate genes for these proteins. The invention further provides new leads for development of candidate genes, and their encoded proteins, and the study of their functional relevance to predictive, preventive or curative approaches. This computational method involves calculation of several sequence attributes and their subsequent analysis, leading to the identification of some outlier proteins in different pathogens. Thus, the present invention is useful for identification of some of the outlier proteins in pathogenic organisms. These outlier proteins are either virulence proteins or antigens or they may be used as drug targets. The outlier proteins from different genomes constitute a set of candidates for functional characterization through targeted gene disruption, microarrays and proteomics. Further, these proteins constitute a set of candidates for further testing in development of anti-infectives such as vaccine candidates, diagnostics or drug targets. Also, the genes encoding the candidate proteins are provided.

BACKGROUND OF THE INVENTION AND PRIOR ART DISCUSSION

The progress in genome sequencing projects has generated a large number of inferred protein sequences from different organisms and, it is likely to increase in the coming years. The availability of complete genome sequences offers an opportunity for increased understanding of the biology of these organisms because it not only provides biological insights on any given organism, but also provides substantially more information on the physiology and evolution of microbial species through comparative analysis (Fraser et al. 2000). The set of microbes whose genomes have been sequenced so far is a diverse one, ranging from organisms living under extreme condition of environment to model organisms of biology, and to some of the most important human pathogens (see, U.S. National Center for Biotechnology Information, U.S. National Institutes of Health, website).

It is expected that the availability of the information on the complete set of proteins from the infectious human pathogens will enable us to develop novel drugs to combat them. This is important in cases such as the emerging epidemic of multiple drug-resistant Mycobacterial isolates (Barry et al. 2000) although, so far, no new drugs derived from genomics-based discovery have been reported to be in a development pipeline (Black and Hare 2000). A paradigm for exploiting the genome to inform the development of novel antituberculars has been proposed, utilizing the techniques of differential gene expression as monitored by DNA microarrays coupled with the emerging discipline of combinatorial chemistry (Barry et al. 2000).

The whole genome sequences of microbial pathogens also present new opportunities for clinical applications such as diagnostics and vaccines (Weinstock et al. 2000). However, the predicted number of proteins encoded in different genomes is fairly large, and about half of that in any given genome is of unknown biological function (Fraser et al. 2000). Some of them are also unique in each organism. In this scenario, development of data mining tools and their application to decipher useful patterns in the protein sequence dataset can be useful for suitable experiments such as differential gene expression, heterologous expression for large-scale (Weinstock et al 2000) and proteomics studies (Chakravarti 2000). Recently, it has been demonstrated that utilization of genome sequences by application of bioinformatics through genomics and proteomics can expedite the vaccine discovery process by rapidly providing a set of potential candidates for further testing (Chakravarti 2000 (a) and (b)). Presently data mining is being carried out using traditional computer programs that perform motif search or identify distinct domains differing in physico-chemical properties such as hydrophobicity, sequence conservation. The drawback of these methods is that the functions of a half to one third number of the proteins remain unknown even after their applications. Therefore, through the application of the presently available computation tools it is likely that potential new candidate for vaccines, diagnostics or drug targets are missed. Therefore, need exists for development of a computational tool that uses different sequence attributes of protein sequences instead of sequence patterns. Through such a shift in framework, the applicants have overcome this limitation. The novelty of the present invention is in development of method based on different attributes of protein sequences, which is useful for prediction of functional role in virulence, immuno-pathogenicity and drug-response.

REFERENCES MAY BE MADE TO

Barry, C. E. 3rd, Slayden, R. A., Sampson, A. E., and Lee, R. E. (2000). Use of genomics and combinatorial chemistry in the development of new antimycobacterial drugs. *Biochem. Pharmacol.* 59(3):221-31.

Black, T., and Hare, R. (2000). Will genomics revolutionize antimicrobial drug discovery? *Curr. Opin. Microbiol.* 3(5):522-7.

Chakravarti, D. N., Fiske, M. J., Fletcher, L. D., and Zagursky, R. J. (2000a). Application of genomics and proteomics for identification of bacterial gene products as potential vaccine candidates. *Vaccine* 19:601-12.

Chakravarti, D. N., Fiske, M. J., Fletcher, L. D., and Zagursky, R. J. (2000b). Mining genomes and mapping proteomes: identification and characterization of protein subunit vaccines. *Dev. Biol.* (Basel) 103:81-90.

Fauchere, J. L. and Pliska, V. (1983). Hydrophobic parameters of amino acid side chains from the partitioning of N-acetyl-amino acid amides. *Eur. J. Med. Chem.-Chim. Ther.* 18:369-375.

Fraser, C. M., Eisen, J., Fleischmann, R. D., Ketchum, K. A. and Peterson, S. (2000). Comparative genomics and understanding of microbial biology. *Emerging Infectious Diseases*, Vol. 6, 505-512.

Hopp, T. P. and Woods, K. R. (1981). Prediction of protein antigenic determinants from amino acid sequences. *Proc. NatL. Acad. Sci. USA,* 78: 3824-3828.

Kester, K. E., McKinney, D. A., Tornieporth, N., Ockenhouse, C. F., Heppner, D. G., Hall, T., Krzych, U., Delchambre, M., Voss, G., Dowler, M. G., Palensky, J., Wittes, J, Cohen, J, and Ballou, W. R. (2001). Efficacy of Recombinant Circumsporozoite Protein Vaccine Regimens against Experimental Plasmodium falciparum Malaria. *J. Infect. Dis.* 183(4): 640-647.

Kyte, J. and Doolittle, R. F. (1982). A simple method for displaying the hydropathic character of a protein. *J. Mol. Biol.* 157:105-132.

Mande, S. S., Gupta, N., Ghosh, A. and Mande, S. C. (2000). Homology model of a novel xylanase: Molecular basis for high-thermostability and alkaline stability. *J. Biomol. Str. Dyn.* 18:137-144.

Mobley, H. L., Garner, R. M., Chippendale, G. R., Gilbert, J. V., Kane, A. V., and Plaut, A. G. (1999). Role of Hpn and NixA of Helicobacter pylori in susceptibility and resistance to bismuth and other metal ions. *Helicobacter* 4(3):162-169.

Nakashima, H. and Nishikawa, K. (1994). Discrimination of intracellular and extracellular proteins using amino acid composition and residue pair frequencies. *J. Mol. Biol.* 238: 54-61.

Ramachandran, S., Nandi, T., Ghai, R., B-Rao, C., Brahmachari, S. K., and Dash, D. Analysis of complete genome sequences using a novel complexity measure (submitted).

Ramakrishnan, L., Federspiel, N. A., and Falkow, S. (2000). Granuloma-specific expression of Mycobacterium virulence proteins from the glycine-rich PE-PGRS family. *Science* 288(5470):1436-9.

Roland, L. and Eisenberg, D. (1992). Protein in Sequence Analysis Primer. Eds. Gribskov, M. and Devereux, J. Oxford University Press, 61-87.

Rose, G. D., Geselowitz, A. R., Lesser, G. J., Lee, R. H., and Zehfus, M. H. (1985). Hydrophobicity of amino acid residues in globular proteins. *Science*, 229: 834-838.

Varadarajan, R., Nagarajaram, H. A., and Ramakrishnan, C. (1996). A procedure for the prediction of temperature-sensitive mutants of a globular protein based solely on the amino acid sequence. *Proc. Natl. Acad. Sci. USA* 93:13908-13.

Weinstock, G. M., Smajs, D., Hardham, J., and Norris, S. J. (2000). From microbial genome sequence to applications. *Res. Microbiol.* 151(2):151-8.

Wien Klin Wochenschr. (1997). August 8; 109(14-15): 551-6. Comparative genomics of mycoplasmas.

Wootton, J. C. (1994). Non globular domains in protein sequences: Automated segmentation using complexity measures. *Comput. Chem.*, 18: 269-285.

OBJECTS OF THE INVENTION

The main object of the present invention is to provide a computational method for identification of proteins useful as anti-infectives. These anti-infectives are vaccine candidates, diagnostics or drug targets.

Another object of invention is to provide proteins with unusual sequence characteristics identified as outliers in different pathogens.

Yet another object of the invention is for providing the use of gene sequences encoding the proteins useful as candidate anti-infectives.

SUMMARY OF THE INVENTION

The present invention relates to a computational method for the identification of candidate proteins useful as anti-infectives. The invention particularly describes a novel strategy to identify outlier proteins in different genomes of pathogens. These anti-infectives are vaccine candidates, diagnostics or drug targets.

BRIEF DESCRIPTION OF THE ACCOMPANYING DRAWINGS

Figure 1:
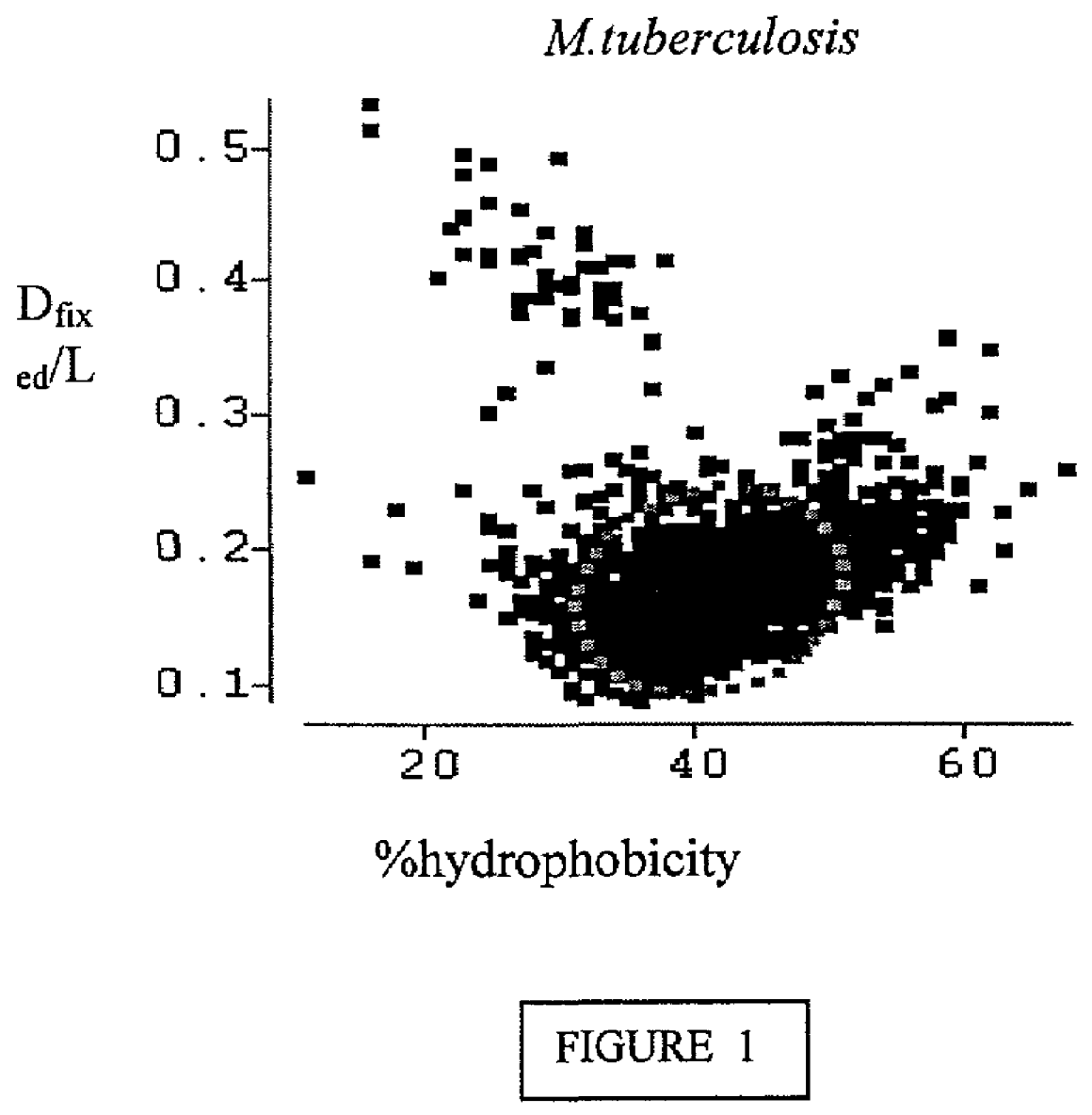

FIG. 1 represents the one of the bivariate relationship for *Mycobacterium tuberculosis*.

DETAILED DESCRIPTION OF THE INVENTION

Accordingly, the present invention provides a novel computational method for the identification of candidate proteins in pathogens useful as anti-infectives. Computational algorithms based on general principles are used to carry out data mining to decipher useful patterns for sequence characterization and classification. This computational method involves calculation of several sequence attributes and their subsequent analysis, leading to the identification of some outlier proteins in different pathogens. Thus, the present invention is useful for identification of some of the outlier proteins in pathogenic organisms. These outlier proteins are either virulence proteins or antigens or used as drug targets. The outlier proteins from different genomes constitute a set of candidates for functional characterization through targeted gene disruption, microarrays and proteomics. Further, these proteins constitute a set of candidates for further testing in development of anti-infectives such as vaccine candidates, diagnostics or drug targets. Also, the genes encoding the candidate proteins are provided.

The invention provides a set of candidate proteins and genes for further evaluation as diagnostic or vaccine candidate or useful for testing in diagnostics or drug susceptibility for human pathogens. The method of the invention is based on the analysis of protein sequence attributes instead of sequence patterns linked to biochemical functions. The present method is independent of the discrepancy inherent with such an approach. The invention provides a computational method, which involves multivariate analysis using Principle Component Analysis (PCA). The proteins termed 'outliers' were found to be excluded from the protein clusters in various pathogens' genomes. Several unique sequences were located on homology analyses of these 'outliers' protein sequences with those in Swiss Prot and PIR database. Some outlier sequences turned out to be identical or homologous to the virulent proteins implicated with antigenic and drug susceptible responses. By this approach, proteins could be identified (short-listed) for further testing in development of anti-infectives in pathogenic organisms.

Computational algorithms based on general principles are needed to carry out data mining to decipher useful patterns for sequence characterization and classification.

The invention has utility for providing new leads for development of anti-infectives of diagnostic, preventive and curative potential.

The present invention relates to a computational method for the identification of candidate proteins useful as anti-infectives.

Accordingly, the present invention provides a novel method for identifying the candidate proteins useful as anti-infectives, said method comprising:

i) calculating computationally the different sequence-based attributes from all the protein sequences of the selected pathogenic organisms.

ii) clustering computationally all the proteins of a genome based on these sequence-based attributes using Principle Component Analysis.

iii) identifying computationally the outlier proteins sequences which are excluded from the main cluster.

iv) matching the outlier protein sequences with the protein sequences in various databases.

v) selecting the unique outlier protein sequences not homologous to any of the protein sequences searched above.

vi) validating computationally the protein sequences as anti-infectives by comparing with the known protein sequences that are biochemically characterized in the pathogen genome.

In an embodiment of the present invention, the protein sequence data is taken from any organism, for example, but not limited to, organisms such as *Borrelia burgdorferi, Campylobacter jejuni, Chlamydia pneumoniae, Chlamydia trachomatis, Haemophilus influenzae, Helicobacter pylori, Leishmania major, Mycoplasma genetalium, Mycoplasma pneumoniae, Mycobacterium tuberculosis, Neisseria meningitis, Pseudomonas aeruginosa, Plasmodium falciparum, Rickettsia prowazekii, Treponema pallidum,* and *Vibrio cholerae.*

In another embodiment of the present invention, different sequence-based attributes used for identification of candidate anti-infective proteins are selected from the group comprising fixed protein and variable protein attributes.

In still another embodiment of the present invention, the fixed protein attributes are selected from the group comprising: percentage of charged amino acids, percentage hydrophobicity, distance of protein sequence from a fixed reference frame, measure of dipeptide complexity of protein, and measure of hydrophobic distance from a fixed reference frame.

In yet another embodiment of the present invention, the variable attribute is the distance of the protein sequence from a variable reference frame.

In one more embodiment of the present invention, the cluster analysis is carried out by Principle Analysis Technique using correlation coefficient between the attributes.

In one other embodiment of the present invention, the steps i) to iv) and vi) are performed computationally.

In an embodiment of the present invention, the clustering of the proteins is based upon analysis of sequence attributes instead of sequence pattern linked to biochemical functions.

In another embodiment of the present invention, the unique outlier protein sequences non-homologous to the known anti-infective sequences are specifically identified in the following pathogens, but not limited to, such as *B. burgdorferi, C. jejuni, C. pneumoniae, C. trachomatis, H. influenzae, H. pylori, L. major, M. genetalium, M. pneumoniae, M. tuberculosis, N. meningitis, P. aeruginosa, P. falciparum, R. prowazekii, T. pallidum,* and *V. cholerae.*

In still another embodiment of the present invention, the unique outlier sequences obtained by the method of invention that can serve as potential anti-infective candidates are listed in Table 1 and List 1.

In yet another embodiment of the present invention, the unique outlier hypothetical protein sequences from pathogenic genomes that can serve as anti-infective candidates are listed in Table 2.

In one more embodiment of the present invention are the genes encoding the unique proteins useful as anti-infectives.

Another embodiment of the present invention is the computer system, comprising a central processing unit, executing the DISTANCE program, followed by clustering of the protein sequences based on different attributes using by Principle Component Analysis, all stored in a memory device accessed by CPU, a display on which the central processing unit displays the screens of the above mentioned programs in response to user inputs; and a user interface device.

In an embodiment of the present invention are the unique outlier hypothetical protein sequences from pathogenic genomes that can be used for diagnostic purposes.

In another embodiment of the present invention are the unique outlier hypothetical protein sequences from pathogenic genomes that can be used as vaccine candidates.

In still another embodiment of the present invention are the unique outlier hypothetical protein sequences from pathogenic genomes that can be used for therapeutic purposes.

Unique outlier protein sequences non-homologous to the known anti-infective sequences are specifically identified in the following pathogens, but not limited to, such as *B. burgdorferi, C. jejuni, C. pneumoniae, C. trachomatis, H. influenzae, H. pylori, L. major, M. genetalium, M. pneumoniae, M. tuberculosis, N. meningitis, P. aeruginosa, P. falciparum, R. prowazekii, T. pallidum,* and *V. cholerae.*

Unique outlier protein sequences obtained by the method of invention that can serve as potential anti-infective candidates and having known properties are listed in Table 1 and List 1.

Unique outlier hypothetical protein sequences from pathogenic genomes that can serve as anti-infective candidates listed in Table 2. These protein sequences have hypothetical functions.

List 1 contains all the protein sequences that were marked as outlier by clustering method. These sequences were obtained from NCBI database.

Other and further aspects, features and advantages of the present invention will be apparent from the following description of the presently preferred embodiments of the invention given for the purpose of disclosure.

Description of Tables and Sequence Lists

List 1 contains all the protein sequences that were marked as outliers by clustering method. These sequences were obtained from NCBI database (see, U.S. National Center for Biotechnology Information, U.S. National Institutes of Health, website).

Table 1 gives the list of outlier proteins with known functions.

Table 2 gives the list of outlier proteins with hypothetical functions.

Brief Description of Computer Program:

The software program was written in PERL (Practical Extraction and Reporting Language) and operated on a Silicon Graphics Origin 200 using IRIX 6.5 operating system. The computer program gives a numerical data of the different attribute, column-wise, for each protein in one record along with its GI number. The values in each column represent the values of the different variates in the multivariate analysis. Using the rationale described above we have developed the data mining software and a software copyright has been filed.

Statistical Analysis

All statistical procedures were carried out using the SAS package (SAS Institute Inc., USA). Principal Component Analysis using correlation coefficients between the variates was carried out using this package.

Sequence Analysis

Homology analysis was carried out using the Wisconsin Package Version 10.0, Genetics Computer Group (GCG), Madison, Wis.

Details of the Invention

The whole genome sequences of microbial pathogens present new opportunities for clinical applications such as diagnostics and vaccines (Weinstock et al. 2000). The present invention provides new leads for the development of candidate genes, and their encoded proteins, in view of their functional relevance to drug responses for use in predictive, preventive or curative approaches.

The protein sequences of several pathogens were obtained computationally from the existing databases (NCBI, genbank/genomes/bacteria). Different sequence attributes like hydrophobicity, charge and measures of compositional distance and dipeptide complexity by a specially developed computer program 'DISTANCE' was used for computation. The attribute profile was obtained for all the proteins for each of the pathogenic genomes. These sequence-based attributes were then used to carry out cluster analysis by the Principal Component Analysis technique using correlation coefficients between the attributes. The proteins falling outside the protein cluster in each genome were identified and termed as outlier proteins. These outlier proteins were compared by BLAST with the sequence of known protein anti-infectives to identify potential candidates for anti-infective lead molecules which can be envisaged to be useful for predictive, preventive and curative purposes against pathogenic infections.

Accordingly, the invention provides a computer-based method for identifying the candidate proteins useful as anti-infectives, which comprises:

1. calculating computationally the different sequence-based attributes from all the protein sequences of the selected pathogenic organisms.
2. clustering computationally all the proteins of a genome based on these sequence-based attributes using Principle Component Analysis.
3. identifying computationally the outlier proteins sequences which are excluded from the main cluster.
4. matching the outlier protein sequences with protein sequences in various databases.
5. selecting the unique outlier protein sequences not homologous to any of the protein sequences searched above.
6. validating computationally the protein sequences as anti-infectives by comparing them with known protein sequences that are biochemically characterized in the pathogen genome.

In an embodiment of the invention, the protein sequence data may be taken from any organism, specifically, but not limited to, organisms such as *B. burgdorferi, C. jejuni, C. pneumoniae, C. trachomatis, H. influenzae, H. pylori, L. major, M. genetalium, M. pneumoniae, M. tuberculosis, N. meningitis, P. aeruginosa, P. falciparum, R. prowazekii, T pallidum,* and *V. cholerae.*

In an embodiment, the non-homologous outlier protein sequence may be compared with that of known anti-infective sequences in the selected pathogens. Several unique outlier sequences were identified to be similar to sequences known to play a role in anti-infectives. These unique sequences obtained by the method of the invention can serve as potential anti-infective candidates.

In another embodiment of the present invention, different sequence-based attributes used for identification of candidate anti-infective proteins comprise charge, hydrophobicity, distance from fixed and variable point of reference, hydrophobic distance and dipeptide complexity.

In another embodiment, the attributes may be of fixed type or variable type.

In another embodiment of the invention, the computer system comprises a central processing unit, executing the DISTANCE program, followed by clustering of the protein sequences based on different attributes using by Principle Component Analysis, all stored in a memory device accessed by CPU, a display on which the central processing unit displays the screens of the above mentioned programs in response to user inputs; and a user interface device.

The particulars of the organisms such as their name, strain, accession number in NCBI database and other details are given below:

| Genomes | Accession No. | No. of bp(s) | Date of completion |
|---|---|---|---|
| B. burgdorferi | NC_001318 | 910724 bp | Dec. 17, 1997 |
| C. jejuni | NC_002163 | 1641481 bp | Feb. 10, 2000 |
| C. pneumoniae CWL029 | NC_000922 | 1230230 bp | Dec. 1, 1998 |
| C. trachomatis | NC_000117 | 1042519 bp | May 20, 1998 |
| H. influenzae | NC_000907 | 1830138 bp | Jul. 25, 1995 |
| H. pylori | NC_000915 | 1667867 bp | Aug. 6, 1997 |
| L. major | | chromosome 1 | |
| M. genetalium | NC_000908 | 580074 bp | Jan. 8, 2001 |
| M. pneumoniae | NC_000912 | 816394 bp | Jun. 15, 1996 |
| M. tuberculosis | NC_000962 | 4411529 bp | Jun. 11, 1998 |
| N. meningitis MC58 | NC_002183 | 2272351 bp | Feb. 25, 2000 |
| P. aeruginosa | NC_002516 | 6264403 bp | May 16, 2000 |
| P. falciparum | | chromosome 2,3 | |
| R. prowazekii | NC_000963 | 1111523 bp | Nov. 12, 1998 |
| T. pallidum | NC_000919 | 1138011 bp | Mar. 6, 1998 |
| V. cholerae | NC_002505 | 2961149 bp | Jun. 14, 2000 |
| | NC_002506 | 1072315 bp | Jun. 14, 2000 |

| Genomes | Total number of proteins |
|---|---|
| B. burgdorferi | 850 |
| C. jejuni | 1634 |
| C. pneumoniae | 1052 |
| C. trachomatis | 894 |
| H. influenzae | 1709 |
| H. pylori | 1553 |
| L. major | 683 |
| M. genetalium | 467 |
| M. pneumoniae | 677 |
| M. tuberculosis | 3918 |
| N. meningitis | 2025 |
| P. aeruginosa | 5565 |
| P. falciparum | 422 |
| R. prowazekii | 834 |
| T. pallidum | 1031 |
| V. cholerae | 3828 |

Another embodiment of the invention is the use of the genes encoding the proteins identified by the methods of the invention.

The invention is further explained with the help of the following examples which are given by illustration and should not be construed to limit the scope of the present invention in any manner.

EXAMPLES

Example 1

Distance

The purpose of the program is to computationally calculate various sequence-based attributes of the protein sequences.

The program works as follows:

The internet downloaded FASTA format files obtained from NCBI (see, U.S. National Center for Biotechnology Information, U.S. National Institutes of Health, website) were saved by the name <organism name>.faa and passed as input to the PERL program which computes the different attributes of protein sequences.

Input/Output format:

Downloaded Files and their format:
<organism name>.faa: file which stores the annotation and the protein sequence.
<organism name> refers to
BB (*Borrelia burgdorferi*), BS (*Bacillus subtilis*), CJ (*Campylobacter jejuni*), CP (*Chlamydia pneumoniae*), CT (*Chlamydia trachomatis*), HI (*Haemophilus influenzae*), HP (*Helicobacter pylori*), LP (*Leishmania major*), MG (*Mycoplasma genetalium*), MP (*Mycoplasma pneumoniae*), MTUB (*Mycobacterium tuberculosis*), NM (*Neisseria meningitis*), PAER (*Pseudomonas aeruginosa*), PF (*Plasmodium falciparum*), RP (*Rickettsia prowazekii*), TP (*Treponema pallidum*), VCHO (*Vibrio cholerae*)
Format: FASTA
">gil"<annotation>
<<the entire protein sequence.................
For example,

```
>gi|2314605|gb|AAD08472|histidine and
glutamine-rich protein
                                    (SEQ ID NO:14)
MAHHEQQQQQQANSQHHHHHHAHHHHYYGGEHHHHNAQQHAEQQAEQQAQ

QQQQQQAHQQQQQKAQQQNQQY

>gi|3261822|gnl|PID|e328405 PE_PGRS
                                    (SEQ ID NO:18)
MIGDGANGGPGQPGGPGGLLYGNGGHGGAGAAGQDRGAGNSAGLIGNGGA

GGAGGNGGIGGAGAPGGLGGDGGKGGFADEFTGGFAQGGRGGFGGNGNTG

ASGGMGGAGGAGGAGGAGGLLIGDGGAGGAGGIGGAGGVGGGGGAGGTGG

GGVASAFGGGNAFGGRGGDGGDGGDGGTGGAGGARGAGGAGGAGGWLSGH

SGAHGAMGSGGEGGAGGGGGARGEAGAGGGTSTGTNPGKAGAPGTQGDSG

DPGPPG

>gil.................
```

The output file: <organism_name>.mdis

Format:

for example format of mtub.mdis:

are the hydrophobicity, charge, and different types of compositional characteristics of a protein. Each attribute was quantified using a measure and each measure uses a reference frame for computation defined later in this section.

The attributes were treated as variates in the statistical analysis. The variates were classified into two categories, namely, 'fixed' and 'variable.' In the case of 'fixed' variates, the reference frame for analysis of different organisms (genomes) is fixed. Thus the reference frame in these cases is not organism specific. For example, a particular scale of hydrophobicity is fixed for the analysis of protein sequences across all organisms. In the case of 'variable' variates, the reference frame for analysis of different organisms (genomes) varies from one to another. In these cases, the reference frame is organism specific.

In this work, we have included variates with reference frames that are not organism specific and that are organism specific because our objective was to analyze the different characteristics of the proteins in one module to enable us to draw inferences with significance and practical utility. Thus, proteins falling as outliers based on all these variates have very different characteristics in general and also from the rest members of the genome.

L is the length of the protein in number of amino acids.

The group of charged amino acids, hydrophobicity scale used, expected number of occurrences of different amino acids, expected number of different dipeptides in a protein, expected number of hydrophobic amino acids—based on a particular hydrophobicity scale—each constitute a reference frame for the different measures used in this work. These measures are described below.

Fixed Variates:

Variate 1: is the percent of charged amino acids in a given protein. The charged amino acids were Aspartic acid (D), Glutamic acid (E), Lysine (K) and Arginine (R). % of Charge is given by $$\frac{\text{Number of charged amino acids}}{L} \times 100 \qquad (1)$$

| Gene name | Length (L) | % Hydrophobicity | % charge | $D_{fixed}$ | $D_{var,high\ complexity}$ | Dipeptide | $D_{phobic}$ |
|---|---|---|---|---|---|---|---|
| >gi|2808711|gnl|PID|e1245984 | 507 | 49.9 | 25.44 | 63.06 | 53.38 | 90 | 53.18 |
| >gi|3261513|gnl|PID|e1299736 | 402 | 60.95 | 21.39 | 68.64 | 40.88 | 81 | 60.3 |
| >gi|1552556|gnl|PID|e266921 | 385 | 58.18 | 27.27 | 71.16 | 43.13 | 79 | 59.25 |
| >gi|1552557|gnl|PID|e266922 | 187 | 56.15 | 25.67 | 34.79 | 23.17 | 22 | 29.1 |
| >gi|1552558|gnl|PID|e266923 | 714 | 51.12 | 27.87 | 87.22 | 80.66 | 154 | 77.04 |
| >gi|1552559|gnl|PID|e266924 | 838 | 53.46 | 27.33 | 116.02 | 88.15 | 196 | 97.71 |
| >gi|1552560|gnl|PID|e266925 | 304 | 61.84 | 17.11 | 54.21 | 34.79 | 49 | 47.55 |
| >gil . . . | | | | | | | |

Example 2

Fixed Protein Attributes

We developed a framework for statistical analysis using the following attributes of proteins. The attributes used here Variate 2: is the percent hydrophobicity of the protein. We have used several hydrophobic scales given by Fauchere & Pliska scale (Fauchere and Pliska, 1983), Hopp & Woods (1981), Kyte & Doolittle (1982) and Rose scale (Rose et al. 1985) to classify the amino acids into hydrophobic and hydrophilic groups respectively.

Percent Hydrophobicity is given by $$\frac{\text{Number of hydrophobic amino acids}}{L} \times 100 \quad (2)$$

Variate 3: is a measure of distance of a protein sequence from a fixed reference frame. The distance is measured according to the formula:

$$D_{fixed} = \sqrt{\sum_{x=1}^{20} (O_x - E_x)^2} \quad (3)$$

$O_x$ is the observed number of xth amino acid in the protein and $E_x$ is the expected number of xth amino acid in the same protein. In this case, $E_x$ is L/20 considering all amino acids to be uniformly distributed in the fixed reference frame. $D_{fixed}/L$ is a normalized measure of distance for the protein.

Variate 4: is a measure of the dipeptide complexity of a protein. The reference frame here is the maximum number of dipeptides possible in the protein for its length. The measure is given by (i) for proteins of L<800 amino acids $$\frac{\text{No. of different peptides observed in the protein}}{(L/2)} \quad (4)$$

and (ii) for proteins of L>800 amino acids $$\frac{\text{No. of different peptides observed in the protein}}{400} \quad (5)$$

Variate 5: is a measure of hydrophobic distance of a protein in a genome from a fixed reference frame.

$$D_{phobic} = \sqrt{\sum_{x=1}^{20} (O_x - E_x)^2} . \quad (6)$$

$O_x$ is the observed number of xth hydrophobic amino acid in the protein and $E_x$ is the expected number of xth hydrophobic amino acid in the same protein. In this case, $$E_x = \frac{\text{total no. of hydrophobic amino acids in the protein}}{z}$$

The computation of $E_x$ assumes uniform distribution of the different hydrophobic amino acid types; z=the number of types of hydrophobic amino acids identified according to a particular hydrophobic scale. This is the fixed reference frame. z will vary according to the hydrophobic scale used. For example in the Kyte & Doolittle scale, z is 13; in the Hopp and Woods scale, z is 11; in the Fauchere & Pliska scale, z is 11; and in the Rose scale, z is 8. $D_{phobic}/L$ is a normalized measure of hydrophobic distance of a protein.

Example 3

Variable Protein Attributes

Variate 6: is the distance of a protein sequence in a genome from a variable reference frame. In this case the distance Dvar, high complexity has the same formula as that in Variate 3 but Ex is calculated according to the formula:

$$E_x = f_x XL \quad (7)$$

where $f_x$ is the frequency of occurrence of the xth amino acid in the set of proteins that are of 'high sequence complexity' within the same genome. For this purpose, we first run the protein sequences encoded in the genome through our sequence complexity analysis computer program (Ramachandran et al.) and classify the proteins into 2 sets, namely, 'high complexity' and 'low complexity' according to the fraction of the low complexity sequences present in each protein.

The frequency of each of the 20 amino acids from the high complexity set of proteins was computed by calculating the number of occurrences of the xth (x=1 to 20) amino acid in the proteins set divided by the total number of amino acids in the same set. The frequency of occurrences of different amino acids in this dataset is referred to as the variable reference frame because the frequency of the different amino acids appearing in the high complexity set of proteins are unequal to each other and varies from one genome to another. As in Variate 3, Dvar, high complexity/L is a normalized measure of distance with respect to the variable reference frame.

Example 4

Clustering by Principle Component Analysis

A representation of one of the bivariate relationship for *M. tuberculosis* is shown in FIG. 1. The ellipse of confidence limit at 80% is also shown. The relationship between the variate $D_{fixed}/L$ and % hydrophobicity shows that most of the proteins in different genomes cluster into a large dense group. A few proteins tend to fall outside the cluster in different organisms. Similar observations were made with all types of bivariate plots and with all organisms (data not shown). These observations indicate the clustering nature of the proteins from different organisms with respect to the protein attributes, and this feature could explain the nature of uniformity observed in the distribution patterns discussed in the previous section. The proteins that fall outside the clusters are termed as 'outliers' in this work. The number of outliers in different organisms vary from one organism to another.

In the present invention the most widely used hydrophobicity scales, charge composition, and various distance measures based on amino acid frequencies have been used. When one hydrophobicity scale is used instead of another, then the list of the outliers changes only very slightly. Most of the outlier proteins are common to all the 4 scales. We have included in our list all the outliers identified using all the 4 different scales of hydrophobicity each taken one at a time.

A comprehensive study has been done to identify the outliers in different genomes by principal components analysis at 0.8 of cumulative proportion of variance. The number of outliers identified in different genomes is given (Tables 1 & 2). It is evident that the number of outliers does not have a clear relationship with the total number of proteins encoded in the different genomes. This indicates that the properties of the outlier proteins do not follow a common trend with respect to the number of proteins encoded in a genome (or the genome size). The number of outliers in the case of *P. falciparum* and *L. major* is with respect to the partial genomic sequences. A clearer picture will emerge after the whole genome is sequenced and the protein coding regions are identified.

Example 5

Prediction of Anti-Infective Annotation in *M. tuberculosis*

Seven outlier sequences were identified in *M. tuberculosis* (Tables 1 & 2). Among these, three protein sequences correspond to glycine-rich protein PE_PGRS (Poly E rich proteins) of *M. tuberculosis*. The amino acid sequences of these can be retrieved from the NCBI database (see, U.S. National Center for Biotechnology Information, U.S. National Institutes of Health, website). The PE_PGRS proteins have been implicated in virulence in this pathogen (Ramakrishnan et al., 2000). These unique outlier protein sequences can therefore be predicted to be potential candidates for an anti-infective approach.

Example 6

Prediction of Anti-Infective Annotation in *H. pylori*

Eight outlier sequences were identified in *H. pylori* (Tables 1 & 2). Bacteria lacking one these outliers, i.e., a histidine rich protein, cultured in vivo, are more susceptible than is the wild type to bismuth and $Ni^{2+}$ (Mobley et al 1999). These unique outlier protein sequences can therefore be predicted to be potential candidates for an anti-infective approach.

Example 7

Prediction of Anti-Infective Annotation in *P. falciparum*

Five outlier sequences were identified in *P. falciparum* (Tables 1 & 2). The circumsporozite protein was evaluated as a vaccine candidate (Kester et al 2001). These unique outlier protein sequences can therefore be predicted to be potential candidates for an anti-infective approach.

The particulars of the organisms such as their name, strain, accession number in NCBI database and other details are given above in List 1.

TABLE 1

List of proteins with known functions

| Organism | GI Number | Protein function | SEQ ID NO: |
|---|---|---|---|
| Eubacteria | | | |
| CJ | 6967728 | highly acidic protein | SEQ ID NO:1 |
| | 6969129 | small hydrophobic protein | SEQ ID NO:2 |
| | 6968493 | putative coiled coil protein | SEQ ID NO:3 |
| | 6968611 | highly acidic protein | SEQ ID NO:4 |
| CP | 4376663 | histone like protein 2 | SEQ ID NO:5 |
| CT | 3522902 | hypothetical protein-possible | SEQ ID NO:6 |
| | 3328438 | frameshift with CT593 histone like protein 2 | SEQ ID NO:7 |

TABLE 1-continued

List of proteins with known functions

| Organism | GI Number | Protein function | SEQ ID NO: |
|---|---|---|---|
| HI | 1573353 | tol A | SEQ ID NO:8 |
| | 1574049 | thiamin ABC transporter | SEQ ID NO:9 |
| | 1574645 | heme exporter protein B | SEQ ID NO:10 |
| | 1573009 | recombination protein | SEQ ID NO:11 |
| HP | 2313421 | poly E-rich protein | SEQ ID NO:12 |
| | 2314604 | histidine rich, metal binding polypeptide | SEQ ID NO:13 |
| | 2314605 | histidine and glutamine rich protein | SEQ ID NO:14 |
| MG | 1046012 | cytaadherence accessory protein | SEQ ID NO:15 |
| | 1046097 | cytaadherence accessory protein | SEQ ID NO:16 |
| MP | 1674069 | adhesin related protein | SEQ ID NO:17 |
| MTUB | 3261822 | PE_PGRS | SEQ ID NO:18 |
| | 2894254 | PE_PGRS | SEQ ID NO:19 |
| | 2924449 | PE_PGRS | SEQ ID NO:20 |
| | 1781260 | PPE | SEQ ID NO:21 |
| PAER | 9947600 | KdpF | SEQ ID NO:22 |
| | 9951563 | alginate regulatory protein AlgP | SEQ ID NO:23 |
| | 9951352 | PhaF | SEQ ID NO:24 |
| TP | 3323280 | dicarboxylate transporter | SEQ ID NO:25 |
| VCHO | 9654609 | iron (III) ABC transporter, permease | SEQ ID NO:26 |
| | 9656364 | tol A | SEQ ID NO:27 |
| Eukaryotes | | | |
| LM | 1743289 | hydrophilic surface protein 2 | SEQ ID NO:28 |
| | 468328 | hydrophilic surface protein | SEQ ID NO:29 |
| PF | 3845179 | predicted integral membrane protein | SEQ ID NO:30 |
| | 4493889 | circumsporozite protein | SEQ ID NO:31 |

TABLE 2 list of hypothetical proteins

| Organism | GI Number | SEQ ID NO | GI Number | SEQ ID NO |
|---|---|---|---|---|
| Eubacteria | | | | |
| BB | 2688482 | SEQ ID NO:32 | 2688343 | SEQ ID NO:37 |
| | 2688046 | SEQ ID NO:33 | 2688447 | SEQ ID NO:38 |
| | 2688045 | SEQ ID NO:34 | 2688540 | SEQ ID NO:39 |
| | 2688103 | SEQ ID NO:35 | 2688768 | SEQ ID NO:40 |
| | 2688333 | SEQ ID NO:36 | 2688793 | SEQ ID NO:41 |
| CJ | 6967728 | SEQ ID NO:42 | 6968409 | SEQ ID NO:46 |
| | 6967819 | SEQ ID NO:43 | 6968423 | SEQ ID NO:47 |
| | 6968034 | SEQ ID NO:44 | 6968200 | SEQ ID NO:48 |
| | 6968265 | SEQ ID NO:45 | | |
| CP | 4377009 | SEQ ID NO:49 | 4377196 | SEQ ID NO:54 |
| | 4377120 | SEQ ID NO:50 | 4376483 | SEQ ID NO:55 |
| | 4377121 | SEQ ID NO:51 | 4376770 | SEQ ID NO:56 |
| | 4377216 | SEQ ID NO:52 | 4376779 | SEQ ID NO:57 |
| | 4376866 | SEQ ID NO:53 | 4376756 | SEQ ID NO:58 |
| CT | 3328515 | SEQ ID NO:59 | 3329121 | SEQ ID NO:61 |
| | 3329021 | SEQ ID NO:60 | | |
| HI | 1574537 | SEQ ID NO:62 | 1574799 | SEQ ID NO:65 |
| | 1574414 | SEQ ID NO:63 | 3212225 | SEQ ID NO:66 |
| | 1574625 | SEQ ID NO:64 | 1574607 | SEQ ID NO:67 |
| HP | 2313229 | SEQ ID NO:68 | 2313894 | SEQ ID NO:71 |
| | 2313552 | SEQ ID NO:69 | 2314686 | SEQ ID NO:72 |
| | 2313684 | SEQ ID NO:70 | | |
| MG | 1045905 | SEQ ID NO:73 | 1045811 | SEQ ID NO:74 |
| MP | 1674046 | SEQ ID NO:75 | 1674374 | SEQ ID NO:78 |
| | 1673719 | SEQ ID NO:76 | 1673775 | SEQ ID NO:79 |
| | 1673772 | SEQ ID NO:77 | | |
| MTUB | 2113965 | SEQ ID NO:80 | 2909499 | SEQ ID NO:82 |
| | 2117265 | SEQ ID NO:81 | | |

TABLE 2-continued list of hypothetical proteins

| Organism | GI Number | SEQ ID NO | GI Number | SEQ ID NO |
|---|---|---|---|---|
| NM | 7225315 | SEQ ID NO:83 | 7227030 | SEQ ID NO:86 |
|  | 7226708 | SEQ ID NO:84 | 7227104 | SEQ ID NO:87 |
|  | 7226768 | SEQ ID NO:85 | 7226645 | SEQ ID NO:88 |
| PAER | 9947556 | SEQ ID NO:89 | 9948900 | SEQ ID NO:91 |
|  | 9949353 | SEQ ID NO:90 | 9948180 | SEQ ID NO:92 |
| RP | 3860652 | SEQ ID NO:93 | 3860651 | SEQ ID NO:94 |
| TP | 3322751 | SEQ ID NO:95 | 3322546 | SEQ ID NO:96 |
| VCHO | 9654409 | SEQ ID NO:97 | 9657724 | SEQ ID NO:102 |
|  | 9654544 | SEQ ID NO:98 | 9657931 | SEQ ID NO:103 |
|  | 9654912 | SEQ ID NO:99 | 9658035 | SEQ ID NO:104 |
|  | 9656707 | SEQ ID NO:100 | 9658254 | SEQ ID NO:105 |
|  | 9657609 | SEQ ID NO:101 | 9656580 | SEQ ID NO:106 |
| Eukaryotes Pathogens |  |  |  |  |
| PF | 3845248 | SEQ ID NO:107 | 4493994 | SEQ ID NO:109 |
|  | 3845292 | SEQ ID NO:108 | 4494004 | SEQ ID NO:110 |
| LM | 6996498 | SEQ ID NO:111 | 6562665 | SEQ ID NO:115 |
|  | 6978417 | SEQ ID NO:112 | 6996509 | SEQ ID NO:116 |
|  | 6899670 | SEQ ID NO:113 | 6433946 | SEQ ID NO:117 |
|  | 6899664 | SEQ ID NO:114 | 5869911 | SEQ ID NO:118 |

Advantages

The method of the invention for identifying unique protein sequences useful as antiinfectives is ab initio. It does not need a teaching data set. These anti-infectives are useful as vaccine candidates, as diagnostics, and in studying drug responses. The method uses sequence attributes instead of sequence patterns. The invention is generally applicable to all genomes and is easy to implement in any setting. This approach results in reproducible results as the method does not depend on variable biochemical characterization of proteins. However, functional information from other systems is helpful in aiding testable predictions. The method of the invention can be used for newly sequenced pathogens to provide a set of candidates for rapid evaluation for the development of anti-infectives.

---

What is claimed is:

1. A method for identifying a candidate protein useful as an anti-infective, comprising:
   (a) calculating computationally protein sequence-based attributes from protein sequences of a pathogenic organism, wherein said protein sequences are predicted either from whole or partial genomic sequences, and wherein said protein sequence-based attributes comprise: percentage of charged amino acids, percentage hydrophobicity, distance of protein sequence from a fixed reference frame, measure of dipeptide complexity, and measure of hydrophobicity from a fixed reference frame, and wherein said pathogenic organism is selected from the group consisting of *B.burgdorfei, C.jejuni, C.pneumoniae, C.trachomatis, H.influenzae, H.pylori, L.major, M.genitalium, M.pneumoniae, M.tuberculosis, N.meningitidis, P.aeruginosa, P.falciparum, R.prowazekii, T.pallidum,* and *V.cholerae;*
   (b) clustering computationally said protein sequences based on said protein sequence-based attributes using Principle Component Analysis;
   (c) identifying computationally outlier protein sequences, wherein said outlier protein sequences appear outside a main cluster;
   (d) comparing said outlier protein sequences to protein sequences listed in public sequence databases of organisms including *B.burgdorfei, C.jejuni, C.pneumoniae, C.trachomatis, H.influenzae, H.pylori, L.major, M.genitalium, M.pneumoniae, M.tuberculosis, N.meningitidis, P.aeruginosa, P.falciparum, R.prowazekii, T.pallidum,* and *V.cholerae* to (1) identify outlier proteins that are unique to said pathogenic organism based on the sequences in the databases accessed for the comparing, and (2) identify outlier proteins that are identical to proteins known to be involved in virulence; and
   (e) displaying the results of said step (d).

2. The method of claim 1, wherein said protein sequence based attributes comprise fixed protein attributes and variable protein attributes.

3. The method of claim 2, wherein a variable protein attribute is a distance of protein sequence from a variable reference frame.

4. The method of claim 1, wherein said clustering is done by Principle Component Analysis using correlation coefficient between said protein sequence-based attributes.

5. The method of claim 1, wherein the outlier protein sequences identified in step (d) are non-homologous to known anti-infective proteins from a pathogen selected from the group consisting of *B.burgdorfei, C.jejuni, C.pneumoniae, C.trachomatis, H.influenzae, H.pylori, L.major,*

*M.genitalium, M.pneumoniae, M.tuberculosis, N.meningitidis, P.aeruginosa, P.falciparum, R.prowazekii, T.pallidum,* and *V.cholerae.*

6. The method of claim 1, wherein the outlier protein sequences identified in step (d) have amino acid sequences selected from the group consisting of SEQ ID Nos: 1-31.

7. The method of claim 1, wherein the outlier protein sequences identified in step (d) have an amino acid sequences selected from the group consisting of SEQ ID Nos: 32-118.

8. The method of claim 1, wherein steps (a)-(c) are performed by a computer system: that executes a program that calculates protein sequence-based attributes, wherein said protein sequence-based attributes comprise:

percentage of charged amino acids, percentage hydrophobicity, distance of protein sequence from a fixed reference frame, measure of dipeptide complexity, and measure of hydrophobicity from a fixed reference frame; and clusters protein sequences based on said protein sequence-based attributes using Principle Component Analysis, thereby producing results.

* * * * *

SEQUENCE LISTING

```
<160> NUMBER OF SEQ ID NOS: 118

<210> SEQ ID NO 1
<211> LENGTH: 51
<212> TYPE: PRT
<213> ORGANISM: C. jejuni
<220> FEATURE:
<221> NAME/KEY: misc_feature
<223> OTHER INFORMATION: highly acidic protein
<221> NAME/KEY: misc_feature
<223> OTHER INFORMATION: gi[69]67728

<400> SEQUENCE: 1

Met Ala Tyr Glu Asp Glu Glu Asp Leu Asn Tyr Asp Asp Tyr Glu Asn
1               5                   10                  15

Glu Asp Glu Glu Tyr Pro Gln Asn His His Lys Asn Tyr Asn Tyr Asp
                20                  25                  30

Asp Asp Asp Tyr Glu Tyr Asp Asp Asp Asn Asn Asp Asp Asp Phe Tyr
                35                  40                  45

Glu Met Asp
    50

<210> SEQ ID NO 2
<211> LENGTH: 32
<212> TYPE: PRT
<213> ORGANISM: C. jejuni
<220> FEATURE:
<221> NAME/KEY: misc_feature
<223> OTHER INFORMATION: small hydrophobic protein
<221> NAME/KEY: misc_feature
<223> OTHER INFORMATION: gi[69]69129
```

```
<400> SEQUENCE: 2

Met Thr Met Leu Asp Ile Phe Glu Ile Ile Phe Ile Thr Thr Val Val
1               5                   10                  15

Ile Ile Gly Phe Gly Gly Ile Val Phe Val Thr Lys Glu Lys Lys
            20                  25                  30

<210> SEQ ID NO 3
<211> LENGTH: 57
<212> TYPE: PRT
<213> ORGANISM: C. jejuni
<220> FEATURE:
<221> NAME/KEY: misc_feature
<223> OTHER INFORMATION: putative coiled coil protein
<221> NAME/KEY: misc_feature
<223> OTHER INFORMATION: gi[69]68493

<400> SEQUENCE: 3

Met Ser Phe Glu Glu Asn Leu Lys His Ala Asn Glu Ser Leu Glu Lys
1               5                   10                  15

Leu Asn Asn Gln Glu Leu Ala Leu Asp Glu Ser Val Lys Ile Tyr Lys
            20                  25                  30

Glu Gly Leu Glu Ser Ile Lys Lys Ala Arg Leu Glu Leu Glu Lys Ala
        35                  40                  45

Lys Leu Glu Val Glu Gln Ile Asp Glu
    50                  55

<210> SEQ ID NO 4
<211> LENGTH: 542
<212> TYPE: PRT
<213> ORGANISM: C. jejuni
<220> FEATURE:
<221> NAME/KEY: misc_feature
<223> OTHER INFORMATION: highly acidic protein
<221> NAME/KEY: misc_feature
<223> OTHER INFORMATION: gi[69]68611

<400> SEQUENCE: 4

Met Lys Ile Leu Leu Leu Asn Glu Asn Pro Val Val Ser Arg Leu Val
1               5                   10                  15

Ser Leu Ser Ala Lys Lys Met Ser Tyr Asp Phe Glu Glu Leu Asn Ala
            20                  25                  30

Tyr Ser Glu Asn Leu Gly Asn Tyr Asp Val Ile Val Val Asp Ser Asp
        35                  40                  45

Thr Pro Ala Pro Leu Lys Ile Leu Lys Glu Lys Cys Asp Arg Leu Ile
    50                  55                  60

Phe Leu Ala Pro Arg Asn Gln Asn Val Glu Asp Ile Asp Ala Gln Ile
65                  70                  75                  80

Leu Gln Lys Pro Phe Leu Pro Thr Asp Phe Leu Asn Leu Leu Asn Asn
                85                  90                  95

Lys Asp Ala Asn Lys His Thr Ser Ile Asp Leu Pro Met Leu Ser Asn
            100                 105                 110

Asp Glu Asn Pro Tyr Ala Asp Ile Ser Leu Asp Leu Asp Asn Leu Asn
        115                 120                 125

Leu Asp Asp Leu Pro Asp Glu Asn Ser Leu Asp Ile Asn Ser Glu Gly
    130                 135                 140

Met Glu Asp Leu Ser Phe Asp Asp Ala Gln Asp Asp Asn Ala Asn
145                 150                 155                 160

Lys Thr Leu Glu Thr Gln Asn Leu Glu His Glu Thr Ile Lys Glu Gln
                165                 170                 175
```

Thr Gln Glu Asp Thr Gln Ile Asp Leu Asp Leu Thr Leu Glu Asp Gly
            180                 185                 190

Glu Ser Glu Lys Glu Asp Leu Ser Gln Glu His Thr Ala Leu Asp Thr
        195                 200                 205

Glu Pro Ser Leu Asp Glu Leu Asp Asp Lys Asn Asp Glu Asp Leu Glu
        210                 215                 220

Ile Lys Glu Asp Lys Asn Glu Glu Ile Glu Lys Gln Glu Leu Leu
225                 230                 235                 240

Asp Asp Ser Lys Thr Asn Thr Leu Glu Met Gln Glu Glu Leu Ser Glu
            245                 250                 255

Ser Gln Asp Asp Asn Ser Asn Lys Thr Leu Glu Thr Gln Asn Leu Glu
            260                 265                 270

His Asp Asn Leu Glu Gln Glu Thr Ile Lys Glu Gln Thr Gln Glu Asp
            275                 280                 285

Thr Gln Ile Asp Leu Asp Leu Thr Leu Glu Asp Gly Glu Ser Glu Lys
        290                 295                 300

Glu Asp Leu Ser Gln Glu His Thr Ala Leu Asp Thr Glu Pro Ser Leu
305                 310                 315                 320

Asp Glu Leu Asp Asp Lys Asn Asp Glu Asp Leu Glu Asp Asn Lys Glu
            325                 330                 335

Leu Gln Ala Asn Ile Ser Asp Phe Asp Asp Leu Pro Glu Val Glu Glu
            340                 345                 350

Gln Glu Lys Glu Met Asp Phe Asp Leu Pro Glu Asp Ala Glu Phe
            355                 360                 365

Leu Gly Gln Ala Lys Tyr Asn Glu Glu Ser Glu Glu Asn Leu Glu Glu
        370                 375                 380

Phe Ala Pro Val Val Glu Asp Ile Gln Asp Ile Asp Asp Phe
385                 390                 395                 400

Ala Ser Asn Leu Ser Thr Gln Asp Gln Ile Lys Glu Glu Leu Ala Gln
            405                 410                 415

Leu Asp Glu Leu Asp Tyr Gly Ile Asp Ser Asp Asn Ser Ser Lys Val
            420                 425                 430

Leu Glu Asp Phe Lys Asp Glu Pro Ile Leu Asp Asp Lys Glu Leu Gly
            435                 440                 445

Thr Asn Glu Glu Glu Val Val Val Pro Asn Leu Asn Ile Ser Asp Phe
        450                 455                 460

Asp Thr Leu Lys Glu Ser Asp Ile Gln Glu Ala Leu Gly Glu Glu Ile
465                 470                 475                 480

Leu Glu Lys Asn Glu Glu Pro Ile Val Ser Asp Val Thr Lys Asp Asp
            485                 490                 495

Asn Ser Glu Glu Ile Val Asn Glu Leu Ser Gln Ser Ile Ala Gly Ala
            500                 505                 510

Ile Thr Ser Ser Ile Lys Asp Asp Thr Leu Lys Ala Ala Leu Lys Gly
        515                 520                 525

Met Asn Met Asn Ile Asn Ile Asn Ile Ser Phe Lys Glu Asp
        530                 535                 540

<210> SEQ ID NO 5
<211> LENGTH: 172
<212> TYPE: PRT
<213> ORGANISM: C. pneumoniaeCWL029
<220> FEATURE:
<221> NAME/KEY: misc_feature
<223> OTHER INFORMATION: histone like protein 2
<221> NAME/KEY: misc_feature
<223> OTHER INFORMATION: gi[43]76663

<400> SEQUENCE: 5

```
Met Ile Gly Ala Gln Lys Lys Gln Ser Gly Lys Lys Thr Ala Ser Arg
1               5                   10                  15

Ala Val Arg Lys Pro Ala Lys Lys Val Ala Ala Lys Arg Thr Val Lys
            20                  25                  30

Lys Ala Thr Val Arg Lys Thr Ala Val Lys Lys Pro Ala Val Arg Lys
        35                  40                  45

Thr Ala Ala Lys Lys Thr Val Ala Lys Lys Thr Ala Lys Arg Thr
    50                  55                  60

Val Arg Lys Thr Val Ala Lys Lys Pro Ala Val Lys Lys Val Ala Ala
65                  70                  75                  80

Lys Arg Val Val Lys Thr Val Ala Lys Lys Thr Thr Ala Lys Arg
                85                  90                  95

Ala Val Arg Lys Thr Val Ala Lys Lys Pro Val Ala Arg Lys Thr Thr
            100                 105                 110

Val Ala Lys Gly Ser Pro Lys Lys Ala Ala Cys Ala Leu Ala Cys
        115                 120                 125

His Lys Asn His Lys His Thr Ser Ser Cys Lys Arg Val Cys Ser Ser
    130                 135                 140

Thr Ala Thr Arg Lys His Gly Ser Lys Ser Arg Val Arg Thr Ala His
145                 150                 155                 160

Gly Trp Arg His Gln Leu Ile Lys Met Met Ser Arg
                165                 170
```

<210> SEQ ID NO 6
<211> LENGTH: 63
<212> TYPE: PRT
<213> ORGANISM: C. trachomatis
<220> FEATURE:
<221> NAME/KEY: misc_feature
<223> OTHER INFORMATION: hypothetical protein-possible frameshift with CT593
<221> NAME/KEY: misc_feature
<223> OTHER INFORMATION: gi[35]22902

<400> SEQUENCE: 6

```
Met Phe Thr Leu Phe Leu Cys Glu His Leu Leu Thr Asn Ile Leu Ala
1               5                   10                  15

Ser Ser Phe Leu Ala Lys Ser Gln Gly Phe Ile Thr Leu Val Asn Leu
            20                  25                  30

Phe His Lys Ile Pro Gly Leu Lys Val Ile Glu Ile Thr Cys Leu Ala
        35                  40                  45

Leu Pro Leu Gly Ile His Ser Ile Ile Gly Phe Ser Tyr Leu Leu
    50                  55                  60
```

<210> SEQ ID NO 7
<211> LENGTH: 203
<212> TYPE: PRT
<213> ORGANISM: C. trachomatis
<220> FEATURE:
<221> NAME/KEY: misc_feature
<223> OTHER INFORMATION: histone like protein 2
<221> NAME/KEY: misc_feature
<223> OTHER INFORMATION: gi[33]28438

<400> SEQUENCE: 7

```
Met Asn Met Leu Gly Val Gln Lys Lys Cys Ser Thr Arg Lys Thr Ala
1               5                   10                  15
```

Ala Arg Lys Thr Val Val Arg Lys Pro Ala Ala Lys Lys Thr Ala Ala
            20                  25                  30

Lys Lys Ala Pro Val Arg Lys Val Ala Ala Lys Lys Thr Val Ala Arg
            35                  40                  45

Lys Thr Val Ala Lys Thr Val Ala Ala Arg Lys Pro Val Ala Lys
    50                  55                  60

Lys Ala Thr Ala Lys Lys Ala Pro Val Arg Lys Val Ala Ala Lys Lys
65                  70                  75                  80

Thr Val Ala Arg Lys Thr Val Ala Lys Lys Thr Val Ala Ala Arg Lys
                85                  90                  95

Pro Val Ala Lys Lys Ala Thr Ala Lys Lys Ala Pro Val Arg Lys Ala
                100                 105                 110

Val Ala Lys Lys Thr Val Ala Arg Lys Thr Val Ala Lys Lys Thr Val
            115                 120                 125

Ala Ala Arg Lys Pro Val Ala Lys Arg Val Ala Ser Thr Lys Lys Ser
        130                 135                 140

Ser Ile Ala Val Lys Ala Gly Val Cys Met Lys Lys His Lys His Thr
145                 150                 155                 160

Ala Ala Cys Gly Arg Val Ala Ala Ser Gly Val Lys Val Cys Ala Ser
                165                 170                 175

Ala Ala Lys Arg Lys Thr Asn Pro Asn Arg Ser Arg Thr Ala His Ser
            180                 185                 190

Trp Arg Gln Gln Leu Met Lys Leu Val Ala Arg
        195                 200

<210> SEQ ID NO 8
<211> LENGTH: 372
<212> TYPE: PRT
<213> ORGANISM: H. influenzae
<220> FEATURE:
<221> NAME/KEY: misc_feature
<223> OTHER INFORMATION: outer membrane integrity protein (tolA)
<221> NAME/KEY: misc_feature
<223> OTHER INFORMATION: gi[15]73353

<400> SEQUENCE: 8

Met Gln Asn Asn Arg Gln Lys Lys Gly Ile Asn Ala Phe Ala Ile Ser
1               5                   10                  15

Ile Leu Leu His Phe Ile Leu Phe Gly Leu Leu Ile Leu Ser Ser Leu
            20                  25                  30

Tyr His Thr Val Glu Ile Met Gly Gly Glu Gly Glu Gly Asp Val
            35                  40                  45

Ile Gly Ala Val Ile Val Asp Thr Gly Thr Ala Ala Gln Glu Trp Gly
    50                  55                  60

Arg Ile Gln Gln Gln Lys Gly Gln Ala Asp Lys Gln Lys Arg Pro
65                  70                  75                  80

Glu Pro Val Val Glu Glu Lys Pro Pro Glu Pro Asn Gln Glu Glu Ile
                85                  90                  95

Lys His Gln Gln Glu Val Gln Arg Gln Glu Leu Lys Arg Gln Gln
            100                 105                 110

Glu Gln Gln Arg Gln Gln Glu Ile Lys Lys Gln Gln Glu Gln Ala Arg
        115                 120                 125

Gln Glu Ala Leu Glu Lys Lys Gln Ala Glu Ala Lys Ala Lys
        130                 135                 140

Gln Ala Ala Glu Ala Ala Lys Leu Lys Ala Asp Ala Glu Ala Lys Arg
145                 150                 155                 160

-continued

```
Leu Ala Ala Ala Ala Lys Gln Ala Glu Glu Ala Lys Ala Lys Ala
                165                 170                 175

Ala Glu Ile Ala Ala Gln Lys Ala Lys Gln Glu Ala Glu Ala Lys Ala
            180                 185                 190

Lys Leu Glu Ala Glu Ala Lys Ala Lys Ala Val Ala Glu Ala Lys Ala
                195                 200                 205

Lys Ala Glu Ala Glu Ala Lys Ala Lys Ala Ala Glu Ala Lys Ala
210                 215                 220

Lys Ala Asp Ala Glu Ala Lys Ala Ala Thr Glu Ala Lys Arg Lys Ala
225                 230                 235                 240

Asp Gln Ala Ser Leu Asp Asp Phe Leu Asn Gly Gly Asp Ile Gly Gly
                245                 250                 255

Gly Ser Ala Ser Lys Gly Gly Asn Thr Asn Lys Gly Gly Thr Gln Gly
            260                 265                 270

Ser Gly Ala Ala Leu Gly Ser Gly Asp Gly Gly Lys Val Gly Asp Gln
        275                 280                 285

Tyr Ala Gly Val Ile Lys Lys Glu Ile Gln Arg Arg Phe Leu Lys Asp
    290                 295                 300

Pro Asn Phe Ala Gly Lys Val Cys Arg Ile Lys Ile Gln Leu Gly Arg
305                 310                 315                 320

Asp Gly Thr Ile Leu Gly Tyr Gln Lys Ile Ser Gly Ser Asp Ile
                325                 330                 335

Cys Ser Ala Ala Leu Ser Ala Val Ala Arg Thr Lys Lys Val Pro Ala
                340                 345                 350

Ala Pro Ser Asp Glu Ile Tyr Glu Lys Tyr Lys Ser Pro Ile Ile Asp
            355                 360                 365

Phe Asp Ile Arg
    370

<210> SEQ ID NO 9
<211> LENGTH: 538
<212> TYPE: PRT
<213> ORGANISM: H. influenzae
<220> FEATURE:
<221> NAME/KEY: misc_feature
<223> OTHER INFORMATION: thiamin ABC transporter, permease protein,
      putative
<221> NAME/KEY: misc_feature
<223> OTHER INFORMATION: gi[15]74049

<400> SEQUENCE: 9

Met Phe Ser Leu Phe His His Pro Gln Leu Arg Pro Arg His Tyr Ala
1               5                   10                  15

Gly Gly Val Val Val Ile Ser Phe Ile Ile Leu Phe Tyr Gly Gly Ala
            20                  25                  30

Leu Ser Ser Ile Phe Ala Leu Gly Gly Glu Leu Gln Trp Arg Ala Trp
        35                  40                  45

Phe Thr Asp Asp Tyr Leu Gln His Leu Ile Leu Phe Ser Phe Gly Gln
    50                  55                  60

Ala Leu Leu Ser Thr Val Leu Ser Ile Phe Phe Gly Leu Leu Leu Ala
65                  70                  75                  80

Arg Ala Leu Phe Tyr Lys Pro Phe Leu Gly Lys Lys Trp Leu Leu Lys
                85                  90                  95

Leu Met Ser Leu Thr Phe Val Leu Pro Ala Leu Val Val Ile Phe Gly
            100                 105                 110

Leu Ile Gly Ile Tyr Gly Ser Ser Gly Trp Leu Ala Trp Leu Ala Asn
        115                 120                 125
```

```
Leu Phe Gly Met Ser Trp Gln Gly His Ile Tyr Gly Leu Ser Gly Ile
            130                 135                 140

Leu Ile Ala His Leu Phe Phe Asn Ile Pro Leu Ala Ala Gln Leu Phe
145                 150                 155                 160

Leu Gln Ser Leu Gln Ser Ile Pro Tyr Gln Arg Gln Leu Ala Ala
                165                 170                 175

Gln Leu Asn Leu Gln Gly Trp Gln Phe Val Lys Leu Val Glu Trp Pro
            180                 185                 190

Val Phe Arg Gln Gln Cys Leu Pro Thr Phe Ser Leu Ile Phe Met Leu
        195                 200                 205

Cys Phe Thr Ser Phe Thr Val Val Leu Thr Leu Gly Gly Pro Gln
        210                 215                 220

Tyr Thr Thr Leu Glu Thr Ala Ile Tyr Gln Ala Ile Leu Phe Glu Phe
225                 230                 235                 240

Asp Leu Pro Lys Ala Ala Leu Phe Ala Met Leu Gln Phe Val Phe Cys
                245                 250                 255

Leu Ile Leu Phe Ser Leu Thr Ser Arg Phe Ser Leu Ser Asn Gln Asn
            260                 265                 270

Gly Leu Ser Asn Ser Asn Ile Trp Phe Glu Lys Pro Lys Ser Ala Val
            275                 280                 285

Lys Ile Phe His Ile Leu Val Leu Leu Val Phe Phe Leu Phe
290                 295                 300

Ser Pro Val Leu Asn Ile Leu Ile Ser Ala Leu Ser Ser Ser Asn Leu
305                 310                 315                 320

Leu Thr Val Trp His Asn Ser Gln Leu Trp Arg Ala Leu Gly Tyr Ser
                325                 330                 335

Leu Ser Ile Ala Pro Leu Ser Ala Leu Leu Ala Leu Thr Met Ala Ile
                340                 345                 350

Ala Leu Leu Leu Ser Arg Arg Leu Glu Trp Leu His Tyr Gln Lys
            355                 360                 365

Ile Ser Gln Phe Ile Ile Asn Ala Gly Met Val Ile Leu Ala Ile Pro
370                 375                 380

Ile Leu Val Leu Ala Met Gly Leu Phe Leu Leu Leu Gln Asp Arg Asp
385                 390                 395                 400

Phe Ser Asn Ile Asp Leu Phe Ile Ile Val Val Phe Cys Asn Ala Leu
                405                 410                 415

Ser Ala Met Pro Phe Val Leu Arg Ile Leu Ser Ala Pro Phe His Asn
            420                 425                 430

Asn Met Arg Tyr Tyr Glu Asn Leu Cys Asn Ser Leu Gly Ile Val Gly
            435                 440                 445

Trp Gln Arg Phe Tyr Leu Ile Glu Trp Lys Thr Leu Arg Ala Pro Leu
        450                 455                 460

Arg Tyr Ala Phe Ala Leu Gly Leu Ala Leu Ser Leu Gly Asp Phe Thr
465                 470                 475                 480

Ala Ile Ala Leu Phe Gly Asn Gln Glu Phe Thr Ser Leu Pro His Leu
                485                 490                 495

Leu Tyr Gln Gln Leu Gly Asn Tyr Arg Asn Gln Asp Ala Ala Val Thr
            500                 505                 510

Ala Gly Ile Leu Leu Leu Leu Cys Gly Ile Leu Phe Ala Phe Ile His
            515                 520                 525

Thr Tyr Arg Asp Ala Asp Asp Leu Ser Lys
530                 535
```

<210> SEQ ID NO 10
<211> LENGTH: 221
<212> TYPE: PRT
<213> ORGANISM: H. influenzae
<220> FEATURE:
<221> NAME/KEY: misc_feature
<223> OTHER INFORMATION: heme exporter protein B (ccmB)
<221> NAME/KEY: misc_feature
<223> OTHER INFORMATION: gi[15]74645

<400> SEQUENCE: 10

Met Ile Phe Leu Glu Ile Ile Lys Arg Glu Leu Gln Ile Ala Met Arg
1               5                   10                  15

Lys Asn Ala Glu Ile Leu Asn Pro Leu Trp Phe Phe Leu Leu Val Ile
            20                  25                  30

Thr Leu Phe Pro Leu Val Ile Gly Pro Asp Pro Lys Leu Leu Ser Arg
        35                  40                  45

Ile Ala Pro Gly Ile Ala Trp Val Ala Ala Leu Leu Ser Ala Leu Leu
    50                  55                  60

Ser Phe Glu Arg Leu Phe Arg Asp Asp Phe Ile Asp Gly Ser Leu Glu
65                  70                  75                  80

Gln Leu Met Leu Thr Ala Gln Pro Leu Pro Met Thr Ala Leu Ala Lys
                85                  90                  95

Val Val Ala His Trp Leu Leu Thr Gly Leu Pro Leu Ile Leu Leu Ser
            100                 105                 110

Pro Ile Ala Ala Leu Leu Leu Ser Leu Glu Val Asn Ile Trp Trp Ala
        115                 120                 125

Leu Val Leu Thr Leu Leu Leu Gly Thr Pro Val Leu Ser Cys Ile Gly
    130                 135                 140

Ala Ile Gly Val Ala Leu Thr Val Gly Leu Arg Lys Gly Gly Val Leu
145                 150                 155                 160

Leu Ser Leu Leu Val Pro Leu Phe Ile Pro Val Leu Ile Phe Ala
                165                 170                 175

Ser Ser Val Leu Glu Ala Ala Gly Leu Asn Val Pro Tyr Gly Gly Gln
            180                 185                 190

Leu Ala Ile Leu Gly Ala Met Met Val Gly Ala Val Thr Leu Ser Pro
        195                 200                 205

Phe Ala Ile Ala Ala Ala Leu Arg Ile Ser Leu Asp Asn
    210                 215                 220

<210> SEQ ID NO 11
<211> LENGTH: 788
<212> TYPE: PRT
<213> ORGANISM: H. influenzae
<220> FEATURE:
<221> NAME/KEY: misc_feature
<223> OTHER INFORMATION: recombination protein (rec2)
<221> NAME/KEY: misc_feature
<223> OTHER INFORMATION: gi[15]73009

<400> SEQUENCE: 11

Met Lys Leu Asn Leu Ile Thr Leu Val Val Leu Leu Ile Val Ala Asp
1               5                   10                  15

Leu Thr Leu Leu Phe Leu Pro Gln Pro Leu Leu Leu Pro Trp Gln Val
            20                  25                  30

Ala Leu Val Ile Ala Leu Val Leu Ile Phe Leu Phe Ile Phe Leu Arg
        35                  40                  45

Arg Asn Phe Leu Val Ser Leu Ala Phe Phe Val Ala Ser Leu Gly Tyr
    50                  55                  60

```
Phe His Tyr Ser Ala Leu Ser Leu Ser Gln Gln Ala Gln Asn Ile Thr
 65                  70                  75                  80

Ala Gln Lys Gln Val Val Thr Phe Lys Ile Gln Glu Ile Leu His Gln
                 85                  90                  95

Gln Asp Tyr Gln Thr Leu Ile Ala Thr Ala Thr Leu Glu Asn Asn Leu
            100                 105                 110

Gln Glu Gln Arg Ile Phe Leu Asn Trp Lys Ala Lys Glu Val Pro Gln
            115                 120                 125

Leu Ser Glu Ile Trp Gln Ala Glu Ile Ser Leu Arg Ser Leu Ser Ala
130                 135                 140

Arg Leu Asn Phe Gly Gly Phe Asp Arg Gln Gln Trp Tyr Phe Ser Lys
145                 150                 155                 160

Gly Ile Thr Ala Val Gly Thr Val Lys Ser Ala Val Lys Ile Ala Asp
                165                 170                 175

Val Ser Ser Leu Arg Ala Glu Lys Leu Gln Gln Val Lys Lys Gln Thr
            180                 185                 190

Glu Gly Leu Ser Leu Gln Gly Leu Leu Ile Ala Leu Ala Phe Gly Glu
            195                 200                 205

Arg Ala Trp Leu Asp Lys Thr Thr Trp Ser Ile Tyr Gln Gln Thr Asn
210                 215                 220

Thr Ala His Leu Ile Ala Ile Ser Gly Leu His Ile Gly Leu Ala Met
225                 230                 235                 240

Gly Ile Gly Phe Cys Leu Ala Arg Val Val Gln Val Phe Phe Pro Thr
                245                 250                 255

Arg Phe Ile His Pro Tyr Phe Pro Leu Val Phe Gly Val Leu Phe Ala
            260                 265                 270

Leu Ile Tyr Ala Tyr Leu Ala Gly Phe Ser Val Pro Thr Phe Arg Ala
            275                 280                 285

Ile Ser Ala Leu Val Phe Val Leu Phe Ile Gln Ile Met Arg Arg His
290                 295                 300

Tyr Ser Pro Ile Gln Phe Phe Thr Leu Val Val Gly Phe Leu Leu Phe
305                 310                 315                 320

Cys Asp Pro Leu Met Pro Leu Ser Val Ser Phe Trp Leu Ser Cys Gly
                325                 330                 335

Ala Val Gly Cys Leu Leu Leu Trp Tyr Arg Tyr Val Pro Phe Ser Leu
            340                 345                 350

Phe Gln Trp Lys Asn Arg Pro Phe Ser Pro Lys Val Arg Trp Ile Phe
            355                 360                 365

Ser Leu Phe His Leu Gln Phe Gly Leu Leu Phe Phe Thr Pro Leu
370                 375                 380

Gln Leu Phe Leu Phe Asn Gly Leu Ser Leu Ser Gly Phe Leu Ala Asn
385                 390                 395                 400

Phe Met Ala Val Pro Ile Tyr Ser Phe Leu Leu Val Pro Leu Ile Leu
                405                 410                 415

Phe Ala Val Phe Thr Asn Gly Thr Met Phe Ser Trp Gln Leu Ala Asn
            420                 425                 430

Lys Leu Ala Glu Gly Ile Thr Gly Leu Ile Ser Val Phe Gln Gly Asn
            435                 440                 445

Trp Leu Thr Val Ser Phe Asn Leu Ala Leu Gly Leu Thr Ala Leu Cys
450                 455                 460

Ala Gly Ile Phe Met Leu Ile Ile Trp Asn Ile Tyr Arg Glu Pro Glu
465                 470                 475                 480
```

-continued

```
Ile Ser Ser Ser Asn Trp Gln Ile Lys Arg Ala Lys Phe Phe Thr Leu
            485                 490                 495
Asn Leu Ser Lys Pro Leu Leu Lys Asn Glu Arg Ile Asn Val Leu Arg
            500                 505                 510
Cys Ser Phe Gly Ile Ile Leu Leu Cys Phe Thr Ile Leu Leu Phe Lys
            515                 520                 525
Gln Leu Ser Lys Pro Thr Trp Gln Val Asp Thr Leu Asp Val Gly Gln
            530                 535                 540
Gly Leu Ala Thr Leu Ile Val Lys Asn Gly Lys Gly Ile Leu Tyr Asp
545                 550                 555                 560
Thr Gly Ser Ser Trp Arg Gly Gly Ser Met Ala Glu Leu Glu Ile Leu
            565                 570                 575
Pro Tyr Leu Gln Arg Glu Gly Ile Val Leu Glu Lys Leu Ile Leu Ser
            580                 585                 590
His Asp Asn Asp His Ala Gly Gly Ala Ser Thr Ile Leu Lys Ala
            595                 600                 605
Tyr Pro Asn Val Glu Leu Ile Thr Pro Ser Arg Lys Asn Tyr Gly Glu
            610                 615                 620
Asn Tyr Arg Thr Phe Cys Thr Ala Gly Arg Asp Trp His Trp Gln Gly
625                 630                 635                 640
Leu His Phe Gln Ile Leu Ser Pro His Asn Val Val Thr Arg Ala Asp
            645                 650                 655
Asn Ser His Ser Cys Val Ile Leu Val Asp Asp Gly Lys Asn Ser Val
            660                 665                 670
Leu Leu Thr Gly Asp Ala Glu Ala Lys Asn Glu Gln Ile Phe Ala Arg
            675                 680                 685
Thr Leu Gly Lys Ile Asp Val Leu Gln Val Gly His His Gly Ser Lys
            690                 695                 700
Thr Ser Thr Ser Glu Tyr Leu Leu Ser Gln Val Arg Pro Asp Val Ala
705                 710                 715                 720
Ile Ile Ser Ser Gly Arg Trp Asn Pro Trp Lys Phe Pro His Tyr Ser
            725                 730                 735
Val Met Glu Arg Leu His Arg Tyr Lys Ser Ala Val Glu Asn Thr Ala
            740                 745                 750
Val Ser Gly Gln Val Arg Val Asn Phe Phe Gln Asp Arg Leu Glu Ile
            755                 760                 765
Gln Gln Ala Arg Thr Lys Phe Ser Pro Trp Tyr Ala Arg Val Ile Gly
            770                 775                 780
Leu Ser Lys Glu
785

<210> SEQ ID NO 12
<211> LENGTH: 505
<212> TYPE: PRT
<213> ORGANISM: H. pylori
<220> FEATURE:
<221> NAME/KEY: misc_feature
<223> OTHER INFORMATION: poly E-rich protein
<221> NAME/KEY: misc_feature
<223> OTHER INFORMATION: gi[23]13421

<400> SEQUENCE: 12

Met Lys Met Ile Leu Phe Asn Gln Asn Pro Met Ile Thr Lys Leu Leu
1               5                   10                  15
Glu Ser Val Ser Lys Lys Leu Glu Leu Pro Ile Glu Asn Phe Asn His
            20                  25                  30
```

-continued

```
Tyr Gln Glu Leu Ser Ala Arg Leu Lys Glu Asn Gln Glu Trp Leu Leu
         35                  40                  45
Ile Ala Asp Asp Glu Cys Leu Glu Lys Leu Asp Gln Val Asp Trp Leu
 50                  55                  60
Glu Leu Lys Glu Thr Ile Ser Gln Asn Lys Asn Ser Val Cys Met Tyr
 65                  70                  75                  80
Lys Lys Gly Asn Glu Ala Gln Pro Phe Leu Glu Gly Phe Glu Val Lys
                 85                  90                  95
Ile Lys Lys Pro Phe Leu Pro Thr Glu Met Leu Lys Val Leu Gln Lys
            100                 105                 110
Lys Leu Gly Ser Asn Ala Ser Glu Leu Glu Pro Ser Gln Asn Leu Asp
            115                 120                 125
Pro Thr Gln Glu Val Leu Glu Thr Asn Trp Asp Glu Leu Glu Asn Leu
130                 135                 140
Gly Asp Leu Glu Ala Leu Val Gln Glu Pro Asn Asn Glu Glu Gln Gln
145                 150                 155                 160
Leu Leu Pro Thr Leu Asn Asp Gln Glu Glu Lys Glu Glu Val Lys Glu
                165                 170                 175
Glu Glu Lys Glu Glu Val Lys Glu Glu Lys Glu Glu Val Lys Glu
            180                 185                 190
Glu Glu Lys Glu Glu Val Lys Glu Thr Pro Gln Glu Glu Lys Lys Pro
            195                 200                 205
Lys Asp Asp Glu Thr Gln Glu Gly Glu Thr Leu Lys Asp Lys Glu Val
            210                 215                 220
Ser Lys Glu Leu Glu Ala Pro Gln Glu Leu Glu Ile Pro Lys Glu Glu
225                 230                 235                 240
Thr Gln Glu Gln Asp Pro Ile Lys Glu Thr Gln Glu Asn Lys Glu
                245                 250                 255
Glu Lys Gln Glu Lys Thr Gln Asp Ser Pro Ser Ala Gln Glu Leu Glu
            260                 265                 270
Ala Met Gln Glu Leu Val Lys Glu Ile Gln Glu Asn Ser Asn Gly Gln
            275                 280                 285
Glu Asn Lys Glu Lys Thr Gln Glu Ser Ala Glu Ile Pro Gln Asp Lys
            290                 295                 300
Glu Ile Gln Glu Val Val Thr Glu Lys Thr Gln Ala Gln Glu Leu Glu
305                 310                 315                 320
Val Pro Lys Glu Lys Thr Gln Glu Ser Ala Glu Ala Leu Gln Glu Thr
                325                 330                 335
Gln Ala His Glu Leu Glu Lys Gln Glu Ile Ala Glu Thr Pro Gln Asp
            340                 345                 350
Val Glu Ile Pro Gln Ser Gln Asp Lys Glu Val Gln Glu Leu Glu Ile
            355                 360                 365
Pro Lys Glu Glu Thr Gln Glu Asn Thr Glu Thr Pro Gln Asp Val Glu
370                 375                 380
Thr Pro Gln Glu Lys Glu Thr Gln Glu Asp His Tyr Glu Ser Ile Glu
385                 390                 395                 400
Asp Ile Pro Glu Pro Val Met Ala Lys Ala Met Gly Glu Glu Leu Pro
                405                 410                 415
Phe Leu Asn Glu Ala Val Ala Lys Ile Pro Asn Asn Glu Asn Asp Thr
            420                 425                 430
Glu Thr Pro Lys Glu Ser Val Thr Glu Thr Ser Lys Asn Glu Asn Asn
            435                 440                 445
Thr Glu Thr Pro Gln Glu Lys Glu Glu Ser Asp Lys Thr Ser Ser Pro
```

-continued

```
                450                 455                 460
Leu Glu Leu Arg Leu Asn Leu Gln Asp Leu Leu Lys Ser Leu Asn Gln
465                 470                 475                 480

Glu Ser Leu Lys Ser Leu Leu Glu Asn Lys Thr Leu Ser Ile Lys Ile
                485                 490                 495

Thr Leu Glu Asp Lys Lys Pro Asn Ala
            500                 505

<210> SEQ ID NO 13
<211> LENGTH: 60
<212> TYPE: PRT
<213> ORGANISM: H. pylori
<220> FEATURE:
<221> NAME/KEY: misc_feature
<223> OTHER INFORMATION: histidine-rich, metal binding polypeptide (hpn)
<221> NAME/KEY: misc_feature
<223> OTHER INFORMATION: gi[23]14604

<400> SEQUENCE: 13

Met Ala His His Glu Glu Gln His Gly Gly His His His His His His
1               5                   10                  15

His Thr His His His His Tyr His Gly Gly Glu His His His His
            20                  25                  30

His Ser Ser His His Glu Glu Gly Cys Cys Ser Thr Ser Asp Ser His
        35                  40                  45

His Gln Glu Glu Gly Cys Cys His Gly His His Glu
    50                  55                  60

<210> SEQ ID NO 14
<211> LENGTH: 72
<212> TYPE: PRT
<213> ORGANISM: H. pylori
<220> FEATURE:
<221> NAME/KEY: misc_feature
<223> OTHER INFORMATION: histidine and glutamine-rich protein
<221> NAME/KEY: misc_feature
<223> OTHER INFORMATION: gi[23]14605

<400> SEQUENCE: 14

Met Ala His His Glu Gln Gln Gln Gln Gln Gln Ala Asn Ser Gln His
1               5                   10                  15

His His His His His Ala His His His Tyr Tyr Gly Gly Glu His
            20                  25                  30

His His His Asn Ala Gln Gln His Ala Glu Gln Ala Glu Gln Gln
        35                  40                  45

Ala Gln Gln Gln Gln Gln Gln Ala His Gln Gln Gln Gln Lys
    50                  55                  60

Ala Gln Gln Gln Asn Gln Gln Tyr
65                  70

<210> SEQ ID NO 15
<211> LENGTH: 1139
<212> TYPE: PRT
<213> ORGANISM: M. genitalium
<220> FEATURE:
<221> NAME/KEY: misc_feature
<223> OTHER INFORMATION: cytadherence-accessory protein
<221> NAME/KEY: misc_feature
<223> OTHER INFORMATION: gi[10]46012

<400> SEQUENCE: 15

Met Ala Lys Asn Lys Gln Ser Val Phe Glu Glu Lys Asn Tyr Thr Gln
1               5                   10                  15
```

-continued

```
Thr Glu Pro Glu Asn Ile Phe Gly Asp Leu Tyr Asp Gly Lys Ser Thr
             20                  25                  30
Val Glu Glu Asp Pro Asn Ile Lys Val Ala Tyr Asp Ala Asp Gly Asn
             35                  40                  45
Gly Tyr Tyr Ile Ala Phe Asn Lys Glu Thr Gly Val Tyr Tyr Asp Pro
 50                  55                  60
Tyr Gly Asp Thr Glu Tyr Asp Ile Ser Gln Leu Phe Asp Glu Asn Gly
 65                  70                  75                  80
Asn Pro Phe Val Phe Asp Glu Lys Gln Glu Asn Asp Tyr Leu Lys
                 85                  90                  95
Tyr Val Gly Asn Pro Asp Tyr Gly Ser Tyr Asp Glu Asn Gly Glu Trp
                100                 105                 110
Val Trp Ser Gly Tyr Phe Glu Asn Asp Gln Trp Ile Ser Thr Lys Glu
            115                 120                 125
Ser Gln Pro Thr Asp Glu Asn Tyr Gly Phe Asp Ser Asp Leu Pro Pro
        130                 135                 140
Glu Val Lys Gln Pro Glu Ser Val Glu Asp Asn Tyr Gly Phe Asp Asn
145                 150                 155                 160
Asp Leu Pro Pro Glu Val Lys Gln Pro Glu Ser Val Glu Asp Asn Tyr
                165                 170                 175
Gly Phe Asp Asn Asp Leu Pro Pro Glu Val Lys Gln Pro Glu Ser Val
            180                 185                 190
Val Asp Gln Pro Ser Ser Asp Asp Tyr Phe Ala Lys Gln Pro Thr Asp
        195                 200                 205
Glu Asn Tyr Gly Phe Asp Asn Asp Leu Pro Pro Glu Val Lys Gln Pro
    210                 215                 220
Glu Ser Val Val Asp Gln Pro Ser Ser Asp Asp His Phe Ala Lys Gln
225                 230                 235                 240
Pro Glu Ser Thr Thr Asp Ser Tyr Ser Phe Asp Ser Asp Leu Pro Gln
                245                 250                 255
Pro Thr Leu Asp Gln Pro Ser Leu Asp Asp His Val Gln Tyr Asn Phe
            260                 265                 270
Asp His His Glu Glu Leu Lys Pro Val Ala Glu Gln Asn Asn Tyr
        275                 280                 285
Gln Val Gly Phe Asp Gln Val Gln Ala Asn Leu Asp Asn Asn Glu Glu
    290                 295                 300
Ile Gln Pro Thr Ala Glu Lys Lys Val Thr Thr Asp Phe Glu Ser Lys
305                 310                 315                 320
Gln Ala Gln Val Val Asp Ser Tyr Gln Leu Pro Ile Asp Thr Asp Gln
                325                 330                 335
Gln Asp Gln Thr Thr Phe Ser Ser Phe Glu Thr Gln Pro Thr Val
            340                 345                 350
Glu Gln Phe Asp Gln Val Asn Ser Glu Val Asn Asp Gln Phe Lys Pro
        355                 360                 365
Glu Ile Thr Lys Glu Pro Val Leu Glu Ser Ser Phe Asn Lys Gln Asp
    370                 375                 380
Val Val Glu Thr Ser Asp Leu Asn Ser Glu Ser Asn Leu Tyr Ser Glu
385                 390                 395                 400
Asn Asn Lys Asp Ala Thr Asn Asn Asp Ser Leu Asn Ser Glu Phe Ile
                405                 410                 415
Gln Leu Asn Ser Asn Ser Glu Thr Ala Ser Asp Asp Val His Tyr Glu
            420                 425                 430
```

```
Ser Lys Ser Glu Pro Ile His Asp Tyr Lys Phe Gly Ser Asp Leu Ser
        435                 440                 445

Gln Ser Asn Ser Asn Asn Ser Leu Glu Ser Glu Pro Val Lys Phe Asn
        450                 455                 460

Ser Glu Thr Ala Pro Asp Ala His Phe Glu Ser Gln Ser Glu Pro Val
465                 470                 475                 480

Asp Gln Val Gln Tyr Asp Ile Tyr Gln Asn Glu Glu Leu Lys Pro Thr
                485                 490                 495

Leu Asp Gln Pro Ser Ser Asp Asp Tyr Phe Ala Lys Gln Pro Thr Asp
            500                 505                 510

Glu Asn Tyr Gly Phe Asp Asn Asp Leu Pro Pro Glu Val Lys Gln Pro
            515                 520                 525

Glu Ser Val Val Asp Gln Pro Ser Ser Asp His Phe Ala Lys Gln
545             550                 555                 560

Pro Glu Ser Thr Thr Asp Ser Tyr Ser Phe Asp Ser Asp Leu Pro Gln
545                 550                 555                 560

Pro Thr Leu Asp Gln Pro Ser Leu Asp Asp His Val Gln Tyr Asn Phe
                565                 570                 575

Asp His His Glu Glu Leu Lys Pro Val Ala Glu Glu Asn Asn Tyr
            580                 585                 590

Gln Val Gly Phe Asp Gln Val Gln Ala Asn Leu Asp Asn Asn Glu Glu
        595                 600                 605

Ile Gln Pro Thr Ala Glu Lys Glu Val Thr Thr Asp Phe Glu Ser Lys
        610                 615                 620

Gln Ala Gln Val Val Asp Ser Tyr Gln Leu Pro Ile Asp Thr Asp Gln
625                 630                 635                 640

Gln Asp Gln Thr Thr Phe Ser Ser Ser Phe Glu Thr Gln Pro Thr Val
                645                 650                 655

Glu Gln Phe Asp Gln Val Asn Ser Glu Val Asn Asp Gln Phe Lys Pro
            660                 665                 670

Glu Ile Thr Lys Glu Pro Val Leu Glu Ser Ser Phe Asn Lys Gln Asp
        675                 680                 685

Val Val Glu Thr Ser Asn Tyr Thr Asn Asn Leu Gln Lys Phe Asp Ile
        690                 695                 700

Gln Ser Asp Asn Lys Ile Thr Ile Thr Thr Lys Lys Ser Ser Pro Gln
705                 710                 715                 720

Ile Pro Thr Thr Leu Pro Ile Ser Phe Val Ser Asn Arg Ile Glu Tyr
                725                 730                 735

Lys Pro Val Glu Thr Leu Ala Leu Asp Asn Lys Glu Ser Gln Gln Glu
            740                 745                 750

Gln Ile Thr Ile Asn Ser Ile Thr Glu Asp Ser Lys Thr Leu Ala Lys
        755                 760                 765

Thr Leu Ser Val Gln Leu Gln Gln Ile Asn Ser Leu Asn Asn Gln Ser
770                 775                 780

Ile Val Thr Ser Glu Ser Val Arg Leu Asp Lys Lys Asp Gln Leu
785                 790                 795                 800

Thr Ile Asn Thr Val Asn Ser Glu Asp Gln Gln Pro Lys Ile Glu Val
                805                 810                 815

Phe Val Lys Ala Lys Glu Pro Val Glu Glu His Ser Ile Thr Gln Asn
            820                 825                 830

Lys Gln Ser Val Glu Asp Lys Ser Glu Leu Asp Asn Phe Asn Lys Lys
        835                 840                 845

Ser Asp Leu Tyr Lys Ile Ile Ser Glu Leu Lys Arg Gly Glu Leu Asn
```

-continued

```
                850                 855                 860
Pro Thr Ile Asn Phe Asp Ala Ile Phe Gln Met Asn Asp Tyr Gln Met
865                 870                 875                 880

Ser Val Lys Gln Ser Phe Ile His Leu Asn Asp Phe Val Thr Asn Tyr
                    885                 890                 895

Lys Asn Gln Ile Ser Glu Arg Tyr Leu Ile Lys Lys Glu Leu Gln
                900                 905                 910

Ser Glu Leu Ser Arg Leu Ile Asp Gln Asn Glu Asn Leu Asn Val Gln
                915                 920                 925

Phe Asn Asn Ala Lys Asn Leu Thr Thr Leu Gln Lys Glu Glu Met Ile
930                 935                 940

Arg Ser Leu Ala Ser Asp Phe Ala Ile Ala Tyr Lys Pro Ser Asn Ser
945                 950                 955                 960

Tyr Glu Gln Leu Gln Lys Ser Gly Glu Ile Met Arg His Val Gln Arg
                965                 970                 975

Ala Ile Thr Glu Asn Glu Lys Lys Ile Glu Ser Ile Gln Gly Ser Leu
                980                 985                 990

Lys Gln Leu Lys Thr Val Tyr Asn  Ser Cys Cys Glu Thr  Ile Met Asn
                995                 1000                1005

Asn Ile  Asn Lys Leu Asp Asn  Thr Leu Arg Phe Ala  Lys Lys Glu
        1010                1015                1020

Lys Asp  Pro Leu Leu Leu Ser  Asn Phe Asp Ser Val  Thr Asp Asn
        1025                1030                1035

Gly Leu  Val Glu Pro Asn Gln  Leu Met Asp Asp Leu  Ile Asp Phe
        1040                1045                1050

Ser Asn  Thr Phe Asp Asn Ile  Ser Asn Glu Gln Leu  Asp Asp Phe
        1055                1060                1065

Ile Tyr  Glu Asn Met Asp Arg  Asn Ile Asp Phe Glu  Phe Glu Gly
        1070                1075                1080

Phe Asn  Asn Asp Phe Val Asp  Ile Asp Ala Lys Val  Met Asp Ser
        1085                1090                1095

Met Ser  Ala Phe Ser Val Asn  Asp Leu Asp Ile Glu  Thr Leu Val
        1100                1105                1110

Pro Asp  Arg Thr Ser Asn Phe  Ser Ser Leu Leu Asp  Glu Asp Leu
        1115                1120                1125

Phe Glu  Ser Ser Gly Asp Phe  Ser Leu Asp Tyr
        1130                1135
```

<210> SEQ ID NO 16
<211> LENGTH: 1616
<212> TYPE: PRT
<213> ORGANISM: M. genitalium
<220> FEATURE:
<221> NAME/KEY: misc_feature
<223> OTHER INFORMATION: cytadherence-accessory protein
<221> NAME/KEY: misc_feature
<223> OTHER INFORMATION: gi[10]46097

<400> SEQUENCE: 16

```
Met Pro Lys Thr Thr Lys Asn Lys Asn Lys Asn Thr Thr Pro Lys Ser
1               5                   10                  15

Lys Thr Lys Lys Tyr Leu Glu Ser Ala Asn Lys Ser Val Thr Lys
                20                  25                  30

Pro Lys Lys Glu Gln Asp Lys Val Glu Asn Leu Phe Asp Gln Pro Phe
            35                  40                  45

Leu Gly Glu Ile Lys Lys Asn Ile Leu Lys Lys Thr Lys Ser Phe Asn
```

```
                50                  55                  60
Ser Lys Lys Lys Glu Thr Val Lys Ser Lys Ser Lys Ser Pro Ile Asp
 65                  70                  75                  80

Phe Phe Asp Glu Thr Lys Arg Gly Val Phe Ile Val Pro Pro Glu Thr
                 85                  90                  95

Asp Ile Leu Ser Arg Arg Glu Leu Asn Gln Lys Thr Val Val Asn Thr
                100                 105                 110

Val Pro Asn Gln Thr Ser Ser Tyr Pro Thr Ile Asn Glu Asn Lys Leu
                115                 120                 125

Val Glu Leu Asn Asn Gln Pro Glu Thr Lys Val Leu Glu Thr Lys Lys
130                 135                 140

Asp Ser Phe Thr Thr Thr Ile Arg Glu Lys Lys Leu Asn Pro Glu Asp
145                 150                 155                 160

Ser Gln Ala Phe Trp Tyr Ile Phe Val Gly Asp Arg Lys Tyr Gly Phe
                165                 170                 175

Trp Lys Asn His Thr Trp Val Trp Leu Gly Tyr Phe Asp Gln Leu Gln
                180                 185                 190

Arg Trp Asn Tyr Phe Lys Val Ile Glu Thr Val Glu Val Pro Gln Glu
                195                 200                 205

His Ala Ala Phe Ile Lys Gln Arg Pro Ala Asp Ile Asp Phe Trp Arg
                210                 215                 220

Pro Leu Val Gly Asn Pro Asn Tyr Gly Phe Val Gln Asn Asn Thr Trp
225                 230                 235                 240

Ile Trp Lys Gly Phe Phe Asp Lys Lys Leu Asn Trp Ile Pro Asp Pro
                245                 250                 255

Val Arg Phe Thr Glu Glu Ala Leu Gly His Thr Asp Ser Leu Val Asp
                260                 265                 270

Glu Ile Glu Lys Lys Thr Ile Ser Glu Gln Pro Tyr Trp Glu Gln Glu
                275                 280                 285

Asn Asp Ile Val Val Thr Val Phe Asn Thr Lys Ser Leu Ala Ser Ser
290                 295                 300

Leu Glu Asn Glu Leu Leu Leu Glu Asn Ser Ser Glu Glu Gln Pro Val
305                 310                 315                 320

Ile Glu Glu Val Lys Pro Arg Arg Asn Glu Val Ile Phe Arg Asn Pro
                325                 330                 335

Val Thr Lys Leu His Phe Glu Lys Glu Lys Phe Glu Phe Leu Asn Pro
                340                 345                 350

Val Lys Glu Thr Asn Glu Thr Ile Pro Leu Ile Glu Ile Val Lys Glu
                355                 360                 365

Glu Val Lys Val Glu Ser Glu Val Glu Ala Pro Val Glu Ile Glu Pro
370                 375                 380

Glu Ala Ala Cys Glu Pro Glu Thr Thr Ile Pro Glu Val Glu Thr Val
385                 390                 395                 400

Phe Val Tyr Glu Asp Asp Leu Lys Gly Leu Asp Ser Asn Gln Thr Gln
                405                 410                 415

Ala Gly Asn Val Pro Glu Val Thr Val Phe Val Tyr Glu Asp Asp
                420                 425                 430

Leu Lys Gly Leu Asp Ser Ile Ile Lys Asp Asp Gln Gln His Asp Glu
                435                 440                 445

Ile Ala Lys His Val Glu His Leu Ser Gln Asp Tyr Ser Lys Glu Ile
                450                 455                 460

Lys Asp Ser Ala Lys Ala Asp Leu Ser Asn Ile Ser Asp Asp Ile Asp
465                 470                 475                 480
```

-continued

Ser Val Trp Lys Glu Phe Gly Ser Phe Thr Asp Glu Thr Gln Lys Ser
            485                 490                 495

Val Glu Glu Lys Ser Gln Val Asp Glu Ile Ile Leu Asp Ala Asn Asn
        500                 505                 510

Asp Phe Ile Asn Glu Ser Leu Phe Arg Asp Glu Val Asn Asn Ile
        515                 520                 525

Asp Ser Gln Ile Asn Glu Thr Val Ser Glu Gln Phe Glu Pro Thr
        530                 535                 540

Tyr Ser Val Asn Glu Phe Gln Gln Phe Ser Glu Pro Val Val Ser
545                 550                 555                 560

Asp Glu Lys Ile Lys Glu Thr Asn Ser Asp Glu Ser Val Asn Thr Asp
            565                 570                 575

Leu Thr Ala Leu Phe Ser Glu Lys Leu Val Asn Glu Val Leu Leu Thr
            580                 585                 590

Asn Glu Tyr Val Asp Val Asn Ala Pro Phe Ser Thr Glu Thr Glu Val
            595                 600                 605

Lys Val Ser Ser Glu Leu Pro Lys Ser Glu Leu Val Asp Glu Ile Thr
            610                 615                 620

Phe Ile Asn Asn Asp Pro Lys Pro Gln Glu Gly Leu Glu Tyr Lys Val
625                 630                 635                 640

Asp Phe Leu Glu Thr Glu Pro Lys Ser Leu Phe Asp Glu Lys Thr Thr
            645                 650                 655

Ile Val Val Glu Ser Glu Pro Pro Phe Ile Gln Pro Asp Leu Ser Leu
            660                 665                 670

Glu Leu Asp Ser Val Asn Asp Val Asp Lys Ser Leu Glu Thr Lys Thr
            675                 680                 685

Thr Ser Val Glu Leu Asn His Glu Glu Ile Gly Asn Glu Phe Ile Asn
            690                 695                 700

Leu Asp Val Ser Glu Lys Glu Val Gln Glu Gln Pro Thr Thr Gln Leu
705                 710                 715                 720

Glu Thr Asp Ser Glu Phe Val Leu Pro Thr Tyr Gln Ile Val Glu Asp
            725                 730                 735

Ser Phe Thr Glu Ser Ala Glu Thr Pro Asn Glu Phe Ser Ser Glu Gln
            740                 745                 750

Lys Asp Thr Leu Glu Phe Ile Ser Gln Thr Gln Glu Val Glu Thr Ser
            755                 760                 765

Glu Ser Asn Val Pro Thr Val Glu Gln Glu Thr Lys Leu Phe Glu His
            770                 775                 780

Gln Asp Glu Asn Asn Leu Phe Thr Pro Leu Pro Leu Asp Leu Thr Glu
785                 790                 795                 800

Ile Ile Glu Ser Asn Ala Leu Phe Asp Ser Lys Pro Asp Glu Lys Glu
            805                 810                 815

Ser Ser Asp Ser Glu Leu Gln Pro Thr Phe Lys Glu Ile Lys Leu Asp
            820                 825                 830

Ser Thr Val Glu Val Pro Gln Glu Ser Ser Gln Val Glu Ala Thr Phe
            835                 840                 845

Asp Thr Val Gln Pro Glu Ala Val Phe Asp Glu Ile Lys Thr Gln Glu
        850                 855                 860

Leu Gln Pro Glu Ala Thr Thr Glu Val Val Phe Asp Asp His Phe Gln
865                 870                 875                 880

Pro Asp Val Gln Pro Glu Gln Thr Pro Gln Glu Ala Lys Phe Asp Ser
            885                 890                 895

```
Pro Val Glu Ile Pro Gln Glu Ser Ser Gln Ala Glu Phe His Ala Glu
            900                 905                 910
Gln Ile Ser Asp Glu Ile Lys Leu Glu Glu Lys Thr Glu Ala Val Phe
            915                 920                 925
Asp His Gln Gln Leu Glu Asn Gln Ser Glu Glu Thr Val Val Thr Pro
            930                 935                 940
Thr Glu Val Thr Ala Phe Glu Pro Glu Thr Ile Glu Thr Gln Leu Glu
945                 950                 955                 960
Pro Ser Ser Glu Asp Gln Pro Ser Glu Pro Ala Leu Asp Gln Asn His
            965                 970                 975
Pro Glu Ile Val Thr Ala Glu Val Glu Gln Ile Phe Asp Gly Thr Lys
            980                 985                 990
Leu Glu Asp Leu Lys Leu Glu Glu Ala Asn Phe Asp Asn Val Glu Asn
            995                 1000                1005
Asn Glu Val Gln Pro Lys Glu Thr Glu Ala Glu Ile Thr Phe Asp
            1010                1015                1020
Glu Thr Lys Glu Leu Gln Gln Glu Thr Ser Ser Glu Pro Leu Ser
            1025                1030                1035
Thr Glu Glu Leu Lys Ser Glu Ala Thr Phe Asp Asn Val Ser Glu
            1040                1045                1050
Ala Glu Ser Glu Ala Val Phe Glu Lys Pro Gln Leu Glu Thr Gln
            1055                1060                1065
Thr Glu Lys Ile Leu Glu Glu Pro Lys Ser Glu Pro Val Asp
            1070                1075                1080
Gln Leu Ile Thr Glu Ala Ser Phe Asp Thr Val Lys His Glu Ala
            1085                1090                1095
Val Phe Asp Lys Asn Gln Thr Gln Thr Glu Gly Leu Glu Glu Pro
            1100                1105                1110
Gln Val Ser Ser Glu Ala Glu Val Val Asp Gln Thr Thr Thr Asp
            1115                1120                1125
Thr Val Gly Glu Pro Glu Ala Val Phe Asp Val Gln Pro Glu Lys
            1130                1135                1140
Thr Thr Glu Val Lys Phe Asp Asp Val Glu Asn Gln Gln Lys Val
            1145                1150                1155
Ile Ser Glu Pro Gln Val Glu Gln Gln Pro Gly Glu Ala Val Phe
            1160                1165                1170
Glu Pro Ser Ala Glu Ala Lys Phe Asp Ser Pro Val Glu Ser Val
            1175                1180                1185
Gln Asp Ser Gln Pro Glu Pro Val Leu Glu Glu Val Gln Thr Gln
            1190                1195                1200
Pro Glu Ile Gln Pro Val Glu Ser Gln Pro Glu Ala Thr Phe Asp
            1205                1210                1215
Thr Val Gln Pro Glu Gln Thr Pro Gln Glu Ala Lys Phe Asp Ser
            1220                1225                1230
Pro Val Glu Thr Val Glu Gln Pro Glu Phe Ser Ser Glu Pro Thr
            1235                1240                1245
Gln Gln His Val Glu Ser Glu Ala Ser Phe Asp Glu Pro Asn Tyr
            1250                1255                1260
Asp Phe Asp Glu Pro Asn Tyr Asp Phe Asp Gln Pro Ser Tyr Asp
            1265                1270                1275
Ser Asp Leu Gln Pro Ser Glu Pro Gln Tyr Asp Val Asp Glu Pro
            1280                1285                1290
Asn Tyr Asp Phe Asp Glu Pro Asn Tyr Glu Ile Glu Ser Lys Pro
```

-continued

```
                1295                1300                1305

Ser Glu Pro Gln Phe Glu Pro Gln Val Glu Gln Gln Pro Gly Glu
    1310                1315                1320

Ala Val Phe Glu Pro Ser Ala Glu Ala Lys Phe Asp Ser Pro Val
    1325                1330                1335

Glu Ser Val Gln Asp Ser Gln Pro Glu Pro Leu Leu Glu Glu Val
    1340                1345                1350

Gln Thr Gln Pro Glu Ile Gln Pro Val Glu Ser Gln Pro Glu Ala
    1355                1360                1365

Thr Phe Asp Thr Val Gln Pro Glu Gln Thr Pro Gln Glu Ala Lys
    1370                1375                1380

Phe Asp Ser Pro Val Glu Thr Ile Gln Glu Pro Gln Val Ser Ser
    1385                1390                1395

Glu Pro Glu Val Val Val Gln Pro Asn Phe Glu Glu Arg Lys Pro
    1400                1405                1410

Glu Thr Val Leu Glu Glu Pro Gln Ala Asp Glu Ile Gln Pro Glu
    1415                1420                1425

Ala Ser Glu Glu Glu Ser Leu Asp Trp Glu Leu Leu Val Gly Asn
    1430                1435                1440

Asn Ser Tyr Gly His Tyr Glu Pro Asp Gly Glu Trp Val Trp Ala
    1445                1450                1455

Gly Phe Phe Gly Asp Asp Gln Lys Trp Asn Lys Asp Ala Thr Val
    1460                1465                1470

Lys Trp Ala Arg Glu Arg Asp Tyr Leu Pro Leu Ile Gly Asp Glu
    1475                1480                1485

Val Tyr Gly Arg Tyr Asn Asn Lys Gly Glu Trp Ile Trp Tyr Gly
    1490                1495                1500

Phe Tyr Asp Glu Ser Gly Asp Trp Val Leu Val Asp Glu Gln Trp
    1505                1510                1515

Lys Asn Arg Gln Pro Arg Ile Asn Glu Ala Pro Lys Phe Trp Glu
    1520                1525                1530

Lys Leu Ile Gly Asn Glu Glu Tyr Gly Tyr Tyr Glu Asp Asn Glu
    1535                1540                1545

Trp Asn Trp Tyr Asp Gly Glu Phe Asp Ser Gly Asn Trp Leu
    1550                1555                1560

Val Phe Gln Ser Glu Glu Thr Glu Asn Leu Asn Glu Asp Ile Thr
    1565                1570                1575

Lys Asp Ile Pro Ala Leu Glu Gly Tyr Asp Ile Asp Ser Ile Asp
    1580                1585                1590

Ala Asp Glu Trp Leu Ser Gln Phe Ser Ala Asp Ala Lys Asp
    1595                1600                1605

Val Phe Gly Ser Asn Asp Lys Lys
    1610                1615

<210> SEQ ID NO 17
<211> LENGTH: 274
<212> TYPE: PRT
<213> ORGANISM: M. pneumoniae
<220> FEATURE:
<221> NAME/KEY: misc_feature
<223> OTHER INFORMATION: 30K adhesin-related protein
<221> NAME/KEY: misc_feature
<223> OTHER INFORMATION: gi[16]74069

<400> SEQUENCE: 17

Met Lys Leu Pro Pro Arg Arg Lys Leu Lys Leu Phe Leu Leu Ala Trp
```

```
              1               5                  10                 15
Met Leu Val Leu Phe Ser Ala Leu Ile Val Leu Ala Thr Leu Ile Leu
                20                  25                 30

Val Gln His Asn Asn Thr Glu Leu Thr Glu Val Lys Ser Glu Leu Ser
                35                  40                 45

Pro Leu Asn Val Val Leu His Ala Glu Glu Asp Thr Val Gln Ile Gln
                50                  55                 60

Gly Lys Pro Ile Thr Glu Gln Ala Trp Phe Ile Pro Thr Val Ala Gly
65                  70                  75                 80

Cys Phe Gly Phe Ser Ala Leu Ala Ile Ile Leu Gly Leu Ala Ile Gly
                85                  90                 95

Leu Pro Ile Val Lys Arg Lys Glu Lys Arg Leu Leu Glu Glu Lys Glu
                100                 105                110

Arg Gln Glu Gln Leu Ala Glu Gln Leu Gln Arg Ile Ser Ala Gln Gln
                115                 120                125

Glu Glu Gln Gln Ala Leu Gln Gln Ala Ala Glu Ala His Ala
                130                 135                140

Glu Ala Glu Val Glu Pro Ala Pro Gln Pro Val Pro Val Pro Pro Gln
145                 150                 155                160

Pro Gln Val Gln Ile Asn Phe Gly Pro Arg Thr Gly Phe Pro Pro Gln
                165                 170                175

Pro Gly Met Ala Pro Arg Pro Gly Met Pro Pro His Pro Gly Met Ala
                180                 185                190

Pro Arg Pro Gly Phe Pro Pro Gln Pro Gly Met Ala Pro Arg Pro Gly
                195                 200                205

Met Pro Pro His Pro Gly Met Ala Pro Arg Pro Gly Phe Pro Pro Gln
                210                 215                220

Pro Gly Met Ala Pro Arg Pro Gly Met Pro Pro His Pro Gly Met Ala
225                 230                 235                240

Pro Arg Pro Gly Phe Pro Pro Gln Pro Gly Met Ala Pro Arg Pro Gly
                245                 250                255

Met Gln Pro Pro Arg Pro Gly Met Pro Pro Gln Pro Gly Phe Pro Pro
                260                 265                270

Lys Arg

<210> SEQ ID NO 18
<211> LENGTH: 256
<212> TYPE: PRT
<213> ORGANISM: M. tuberculosis
<220> FEATURE:
<221> NAME/KEY: misc_feature
<223> OTHER INFORMATION: PE_PGRS
<221> NAME/KEY: misc_feature
<223> OTHER INFORMATION: gi[32]61822

<400> SEQUENCE: 18

Met Ile Gly Asp Gly Ala Asn Gly Gly Pro Gly Gln Pro Gly Gly Pro
1               5                   10                 15

Gly Gly Leu Leu Tyr Gly Asn Gly Gly His Gly Ala Gly Ala Ala
                20                  25                 30

Gly Gln Asp Arg Gly Ala Gly Asn Ser Ala Gly Leu Ile Gly Asn Gly
                35                  40                 45

Gly Ala Gly Gly Ala Gly Gly Asn Gly Ile Gly Gly Ala Gly Ala
                50                  55                 60

Pro Gly Gly Leu Gly Gly Asp Gly Gly Lys Gly Gly Phe Ala Asp Glu
65                  70                  75                 80
```

Phe Thr Gly Gly Phe Ala Gln Gly Gly Arg Gly Gly Phe Gly Gly Asn
                85                  90                  95

Gly Asn Thr Gly Ala Ser Gly Gly Met Gly Gly Ala Gly Gly Ala Gly
            100                 105                 110

Gly Ala Gly Gly Ala Gly Gly Leu Leu Ile Gly Asp Gly Gly Ala Gly
        115                 120                 125

Gly Ala Gly Gly Ile Gly Gly Ala Gly Gly Val Gly Gly Gly Gly
    130                 135                 140

Ala Gly Gly Thr Gly Gly Gly Val Ala Ser Ala Phe Gly Gly
145                 150                 155                 160

Asn Ala Phe Gly Gly Arg Gly Gly Asp Gly Gly Asp Gly Gly Asp Gly
                165                 170                 175

Gly Thr Gly Gly Ala Gly Gly Ala Arg Gly Ala Gly Gly Ala Gly Gly
            180                 185                 190

Ala Gly Gly Trp Leu Ser Gly His Ser Gly Ala His Gly Ala Met Gly
        195                 200                 205

Ser Gly Gly Glu Gly Gly Ala Gly Gly Gly Gly Ala Arg Gly Glu
    210                 215                 220

Ala Gly Ala Gly Gly Gly Thr Ser Thr Gly Thr Asn Pro Gly Lys Ala
225                 230                 235                 240

Gly Ala Pro Gly Thr Gln Gly Asp Ser Gly Asp Pro Gly Pro Gly
                245                 250                 255

<210> SEQ ID NO 19
<211> LENGTH: 484
<212> TYPE: PRT
<213> ORGANISM: M. tuberculosis
<220> FEATURE:
<221> NAME/KEY: misc_feature
<223> OTHER INFORMATION: PE_PGRS
<221> NAME/KEY: misc_feature
<223> OTHER INFORMATION: gi[28]94254

<400> SEQUENCE: 19

Ala Gln Ala Ser Pro Ala Ala His Gly Gly Ser Gly Gly Ala Gly Gly
1               5                   10                  15

Asn Gly Gly Ala Gly Ser Ala Gly Asn Gly Gly Ala Gly Gly Ala Gly
            20                  25                  30

Gly Asn Gly Gly Ala Gly Gly Asn Gly Gly Gly Asp Ala Gly Asn
        35                  40                  45

Ala Gly Ser Gly Gly Asn Gly Gly Lys Gly Gly Asp Gly Val Gly Pro
    50                  55                  60

Gly Ser Thr Gly Gly Ala Gly Gly Lys Gly Gly Ala Gly Ala Asn Gly
65                  70                  75                  80

Gly Ser Ser Asn Gly Asn Ala Arg Gly Gly Asn Ala Gly Asn Gly Gly
                85                  90                  95

His Gly Gly Ala Gly Gly Ser Gly Asp Thr Gly Gly Ala Gly Gly Ala
            100                 105                 110

Gly Gly Gln Gly Gly Phe Gly Gly Thr Gly Gly Ser Gly Ser Gly Ile
        115                 120                 125

Gly Gly Gly Ala Gly Gly Asn Gly Gly Asn Gly Gly Ala Gly Gly Thr
    130                 135                 140

Gly Val Val Leu Gly Gly Lys Gly Gly Asp Gly Gly Asn Gly Asp His
145                 150                 155                 160

Gly Gly Pro Ala Thr Asn Pro Gly Ser Gly Ser Arg Gly Gly Ala Gly
                165                 170                 175

```
Gly Ser Gly Gly Asn Gly Gly Ala Gly Gly Asn Ala Thr Gly Ser Gly
            180                 185                 190

Gly Lys Gly Gly Ala Gly Gly Asn Gly Gly Asp Gly Ser Phe Gly Ala
            195                 200                 205

Thr Ser Gly Pro Ala Ser Ile Gly Val Thr Gly Ala Pro Gly Gly Asn
    210                 215                 220

Gly Gly Lys Gly Gly Ala Gly Gly Ser Asn Pro Asn Gly Ser Gly Gly
225                 230                 235                 240

Asp Gly Gly Lys Gly Gly Asn Gly Gly Ala Gly Gly Asn Gly Gly Ser
                245                 250                 255

Ile Gly Ala Asn Ser Gly Ile Val Gly Gly Ser Gly Gly Ala Gly Gly
            260                 265                 270

Ala Gly Ala Gly Gly Asn Gly Ser Leu Ser Ser Gly Glu Gly Gly
            275                 280                 285

Lys Gly Gly Asp Gly Gly His Gly Gly Asp Gly Val Gly Gly Asn Ser
            290                 295                 300

Ser Val Thr Gln Gly Gly Ser Gly Gly Gly Gly Ala Gly Gly Ala
305                 310                 315                 320

Gly Gly Ser Gly Phe Phe Gly Gly Lys Gly Gly Phe Gly Gly Asp Gly
            325                 330                 335

Gly Gln Gly Gly Pro Asn Gly Gly Thr Val Gly Thr Val Ala Gly
            340                 345                 350

Gly Gly Gly Asn Gly Gly Val Gly Gly Arg Gly Gly Asp Gly Val Phe
            355                 360                 365

Ala Gly Ala Gly Gly Gln Gly Gly Leu Gly Gly Gln Gly Gly Asn Gly
            370                 375                 380

Gly Gly Ser Thr Gly Gly Asn Gly Gly Leu Gly Ala Gly Gly Gly
385                 390                 395                 400

Gly Gly Asn Ala Pro Asp Gly Gly Phe Gly Gly Asn Gly Gly Lys Gly
            405                 410                 415

Gly Gln Gly Gly Ile Gly Gly Gly Thr Gln Ser Ala Thr Gly Leu Gly
            420                 425                 430

Gly Asp Gly Gly Asp Gly Gly Asp Gly Gly Asn Gly Asn Ser Gly
            435                 440                 445

Ala Lys Ala Gly Gly Ala Gly Lys Gly Gln Ala Gly Gln Pro Asn
    450                 455                 460

Ser Gly Thr Glu Pro Gly Phe Gly Gly Asp Gly Gly Leu Gly Gly Ala
465                 470                 475                 480

Gly Ala Thr Pro

<210> SEQ ID NO 20
<211> LENGTH: 1079
<212> TYPE: PRT
<213> ORGANISM: M. tuberculosis
<220> FEATURE:
<221> NAME/KEY: misc_feature
<223> OTHER INFORMATION: PE_PGRS
<221> NAME/KEY: misc_feature
<223> OTHER INFORMATION: gi[29]24449

<400> SEQUENCE: 20

Pro Gln Gly Ala Asp Gly Asn Ala Gly Asn Gly Gly Asp Gly Gly Val
1               5                   10                  15

Gly Gly Asn Gly Gly Asn Gly Ala Asp Asn Thr Thr Ala Ala Ala
            20                  25                  30
```

-continued

```
Gly Thr Thr Gly Gly Ala Gly Ala Gly Ala Gly Gly Thr Gly
         35                  40                  45
Gly Thr Gly Gly Ala Ala Gly Thr Gly Thr Gly Gln Gln Gly Asn
 50                  55                  60
Gly Gly Asn Gly Gly Asn Gly Gly Thr Gly Gly Lys Gly Gly Thr Gly
 65                  70                  75                  80
Gly Asp Gly Ala Leu Ala Gly Ser Ser Gly Ala Gly Gly Lys Gly
                 85                  90                  95
Gly Asn Gly Gly Asp Ala Gly Lys Ala Gly Thr Gly Ser Ala Pro Gly
                100                 105                 110
Thr Ala Gly Thr Gly Gly Asp Gly Gly Lys Gly Gly Asn Gly Gly Ile
             115                 120                 125
Gly Ala Ala Gly Thr Thr Gly Pro Val Gly Thr Gly Ala Ser Gly Gly
     130                 135                 140
Thr Gly Gly Ser Gly Gly Ala Gly Gly Thr Gly Gly Asp Gly Gly Ala
145                 150                 155                 160
Ala Asn Gly Gly Thr Ala Gly Ala Gly Gly Ala Gly Asn Gly Gly
                 165                 170                 175
Lys Gly Gly Asp Gly Gly Ala Gly Val Thr Ser Ser Thr Ala Gly Asn
             180                 185                 190
Ser Gly Gly Ala Gly Gly Ser Gly Gly Lys Gly Gly Asp Ala Gly Ala
     195                 200                 205
Gly Gly Ala Gly Ala Thr Pro Gly Ala Asn Gly Ile Ala Gly Asn Gly
     210                 215                 220
Gly Asp Gly Gly Asp Gly Ala Ala Gly Ala Val Gly Ile Ser Gly Ala
225                 230                 235                 240
Thr Gly Ala Gly Asp Gly Gly His Gly Gly Thr Gly Ala Ala Gly Gly
                 245                 250                 255
Asn Gly Gly Thr Gly Gly Ala Gly Gly Ser Gly Ile Asp Gly Val Gly
             260                 265                 270
Gly Gly Thr Gly Gly Thr Gly Gly Asn Gly Gly Asn Gly Ala Ile Gly
     275                 280                 285
Gly Ala Gly Gly Asp Ala Gly Gly Ser Gly Asn Ser Gly Gly Asn Gly
290                 295                 300
Gly Ile Gly Gly Lys Gly Gly Asn Ala Gly Ala Gly Gly Ala Ala Gly
305                 310                 315                 320
Ser Asn Gly Gly Thr Val Gly Ala Asn Gly Thr Gly Gly Asp Gly Gly
                 325                 330                 335
Asn Gly Gly Ala Ala Gly Ala Ala Thr Ala Gly Ser Asn Gly Gly Ala
             340                 345                 350
Gly Thr Gly Ser Ala Gly Gly Asn Gly Gly Thr Gly Gly Arg Gly Gly
     355                 360                 365
Ser Gly Gly Ala Gly Gly Asp Gly Ile Gly Gly Val Gly Gly Gly Lys
     370                 375                 380
Gly Gly Asn Gly Ala Asp Gly Glu Val Gly Gly Ala Gly Gly Ala Gly
385                 390                 395                 400
Gly Ser Gly Pro Asn Thr Ser Pro Gly Gly Asn Gly Gly Gln Gly Gly
                 405                 410                 415
Gln Gly Gly Ser Gly Gly Ala Gly Gly Ala Ala Gly Ala Gly Gly Ala
             420                 425                 430
Gly Gly Gly Ala Asn Gly Thr Ala Gly Asn Gly Gly Gln Gly Gly Ala
     435                 440                 445
Gly Gly Thr Gly Gly Ala Gly Ala Ala Ser Ser Ala Thr Asn Gly Gly
```

-continued

```
            450                 455                 460
Ser Gly Gly Ala Gly Gly Thr Gly Gly Asp Gly Ser Gly Gly Ala
465                 470                 475                 480
Gly Gly Thr Gly Gly Ala Gly Gly Thr Gly Gly Ala Ala Gly Asp Gly
                485                 490                 495
Gly Gln Gly Gly Gln Gly Gly Ala Gly Gly Ala Gly Gly Gln Gly
                500                 505                 510
Gly Ala Gly Gly Ala Gly Gly Thr Gly Gly Asn Gly Gly Asn Ile Thr
                515                 520                 525
Gly Gly Thr Ala Gly Thr Ala Gly Ala Ala Gly Asn Gly Gly Ala Ala
            530                 535                 540
Gly Lys Gly Gly Ala Gly Gly Gln Gly Gly Thr Gly Gly Gly Thr Gly
545                 550                 555                 560
Gly Gln Gly Gly Ala Gly Gly Asp Gly Gly Ala Gly Gly Thr Gly Gly
                565                 570                 575
Asp Arg Thr Val Gly Gly Gly Thr Val Pro Ala Gly Ser Gly Gly Gln
                580                 585                 590
Gly Gly Asn Ala Gly Gly Gly Ala Gly Gly Gln Gly Gly Ala Asp
                595                 600                 605
Gly Gly Ser Gly Gly Asp Gly Gly Asp Ala Gly Thr Gly Gly Asn Gly
                610                 615                 620
Gly Asn Gly Gly Asn Arg Asn Ser Gly Asn Gly Thr Gly Gly Ala Gly
625                 630                 635                 640
Gly Asn Gly Gly Gly Ala Asn Gly Gly Ala Gly Gly Ala Gly Gly
                645                 650                 655
Ser Gly Gly Gly Thr Gly Gly Asn Gly Gly Ala Gly Gly Asp Ala Gly
                660                 665                 670
Asp Ala Gly Asn Gly Gly Asn Gly Asn Gly Thr Gly Asn Gly Gly Asn
                675                 680                 685
Gly Gly Asn Gly Gly Ile Ala Gly Met Gly Gly Asn Gly Gly Ala Gly
                690                 695                 700
Thr Gly Ser Gly Asn Gly Gly Asn Gly Gly Ser Gly Gly Asn Gly Gly
705                 710                 715                 720
Asn Ala Gly Met Gly Gly Asn Ser Gly Thr Gly Ser Gly Asp Gly Gly
                725                 730                 735
Ala Gly Gly Asn Gly Gly Ala Ala Gly Thr Gly Gly Thr Gly Gly Asp
                740                 745                 750
Gly Gly Leu Thr Gly Thr Gly Gly Thr Gly Gly Ser Gly Gly Thr Gly
                755                 760                 765
Gly Asp Gly Gly Asn Gly Gly Asn Gly Ala Asp Asn Thr Ala Asn Met
                770                 775                 780
Thr Ala Gln Ala Gly Gly Asp Gly Gly Asn Gly Gly Asp Gly Gly Phe
785                 790                 795                 800
Gly Gly Gly Ala Gly Ala Gly Gly Gly Leu Thr Ala Gly Ala Asn
                805                 810                 815
Gly Thr Gly Gly Gln Gly Gly Ala Gly Gly Asp Gly Gly Asn Gly Ala
                820                 825                 830
Ile Gly Gly His Gly Pro Leu Thr Asp Asp Pro Gly Gly Asn Gly Gly
                835                 840                 845
Thr Gly Gly Asn Gly Gly Thr Gly Gly Thr Gly Gly Ala Gly Ile Gly
                850                 855                 860
Ser Leu Gly Gly Gly Thr Gly Gly Asp Gly Gly Asn Gly Gly Asn Gly
865                 870                 875                 880
```

```
Gly Thr Gly Gly Glu Gly Gly Glu Val Gly Gly Ala Gly Gly Thr Gly
                885                 890                 895

Gly Ala Ala Gly Asn Gly Gly Asp Gly Gly Thr Gly Gly Thr Gly Gly
            900                 905                 910

Gly Asp Gly Gly Ala Gly Gly Thr Gly Gly Thr Gly Gly Thr Gly Gly
        915                 920                 925

Leu Gly Asp Pro Arg Val Gly Gly Ser Gly Gly Asp Gly Gly Thr Gly
    930                 935                 940

Gly Ser Gly Gly Ala Ala Gly Asn Gly Gly Asn Gly Gly Asn Ala Gly
945                 950                 955                 960

Ala Gly Gly Asn Gly Asn Gly Gly Thr Gly Gly Ala Gly Gly Ile Gly
                965                 970                 975

Gly Thr Gly Gly Asn Gly Gly Asp Ala Glu Pro Gly Val Pro Pro Gly
            980                 985                 990

Ala Gly Gly Ala Gly Gly Ala Gly Thr Thr Gly Gly Lys Gly Gly Thr
        995                 1000                1005

Gly Gly Asn Gly Ser Gly Thr Gly Ser Gly Gly Thr Gly Gly Asp
    1010                1015                1020

Gly Gly Thr Gly Gly Gly Gly Asn Gly Gly Thr Gly Trp Asn
        1025                1030                1035

Gly Gly Lys Gly Asp Thr Gly Ser Gly Gly Ala Gly Asp Gly
        1040                1045                1050

Gly Lys Ala Pro Ala Gly Gly Thr Gly Gly Ala Gly Gly Asp Gly
    1055                1060                1065

Gly Ala Gly Gly Lys Gly Gly Ser Gly Gly Val
    1070                1075

<210> SEQ ID NO 21
<211> LENGTH: 354
<212> TYPE: PRT
<213> ORGANISM: M. tuberculosis
<220> FEATURE:
<221> NAME/KEY: misc_feature
<223> OTHER INFORMATION: PPE
<221> NAME/KEY: misc_feature
<223> OTHER INFORMATION: gi[17]81260

<400> SEQUENCE: 21

Met Pro Gly Arg Phe Arg Asn Phe Gly Ser Gln Asn Leu Gly Ser Gly
1               5                   10                  15

Asn Ile Gly Ser Thr Asn Val Gly Ser Gly Asn Ile Gly Ser Thr Asn
            20                  25                  30

Val Gly Ser Gly Asn Ile Gly Asp Thr Asn Phe Gly Asn Gly Asn Asn
        35                  40                  45

Gly Asn Phe Asn Phe Gly Ser Gly Asn Thr Gly Ser Asn Asn Ile Gly
    50                  55                  60

Phe Gly Asn Thr Gly Ser Gly Asn Phe Gly Phe Gly Asn Thr Gly Asn
65                  70                  75                  80

Asn Asn Ile Gly Ile Gly Leu Thr Gly Asp Gly Gln Ile Gly Ile Gly
                85                  90                  95

Gly Leu Asn Ser Gly Ser Gly Asn Ile Gly Phe Gly Asn Ser Gly Thr
            100                 105                 110

Gly Asn Val Gly Leu Phe Asn Ser Gly Thr Gly Asn Val Gly Phe Gly
        115                 120                 125

Asn Ser Gly Thr Ala Asn Thr Gly Phe Gly Asn Ala Gly Asn Val Asn
    130                 135                 140
```

-continued

```
Thr Gly Phe Trp Asn Gly Gly Ser Thr Asn Thr Gly Leu Ala Asn Ala
145                 150                 155                 160

Gly Ala Gly Asn Thr Gly Phe Phe Asp Ala Gly Asn Tyr Asn Phe Gly
                165                 170                 175

Ser Leu Asn Ala Gly Asn Ile Asn Ser Ser Phe Gly Asn Ser Gly Asp
            180                 185                 190

Gly Asn Ser Gly Phe Leu Asn Ala Gly Asp Val Asn Ser Gly Val Gly
        195                 200                 205

Asn Ala Gly Asp Val Asn Thr Gly Leu Gly Asn Ser Gly Asn Ile Asn
    210                 215                 220

Thr Gly Gly Phe Asn Pro Gly Thr Leu Asn Thr Gly Phe Phe Ser Ala
225                 230                 235                 240

Met Thr Gln Ala Gly Pro Asn Ser Gly Phe Phe Asn Ala Gly Thr Gly
                245                 250                 255

Asn Ser Gly Phe Gly His Asn Asp Pro Ala Gly Ser Gly Asn Ser Gly
            260                 265                 270

Ile Gln Asn Ser Gly Phe Gly Asn Ser Gly Tyr Val Asn Thr Ser Thr
        275                 280                 285

Thr Ser Met Phe Gly Gly Asn Ser Gly Val Leu Asn Thr Gly Tyr Gly
    290                 295                 300

Asn Ser Gly Phe Tyr Asn Ala Ala Val Asn Asn Thr Gly Ile Phe Val
305                 310                 315                 320

Thr Gly Val Met Ser Ser Gly Phe Phe Asn Phe Gly Thr Gly Asn Ser
                325                 330                 335

Gly Leu Leu Val Ser Gly Asn Gly Leu Ser Gly Phe Phe Lys Asn Leu
            340                 345                 350

Phe Gly

<210> SEQ ID NO 22
<211> LENGTH: 29
<212> TYPE: PRT
<213> ORGANISM: Pseudomonas aeruginosa
<220> FEATURE:
<221> NAME/KEY: misc_feature
<223> OTHER INFORMATION: KdpF protein
<221> NAME/KEY: misc_feature
<223> OTHER INFORMATION: gi[99]47600

<400> SEQUENCE: 22

Met Thr Val Leu Asp Trp Leu Ser Leu Ala Leu Ala Thr Gly Leu Phe
1               5                   10                  15

Val Tyr Leu Leu Val Ala Leu Leu Arg Ala Asp Arg Ala
            20                  25

<210> SEQ ID NO 23
<211> LENGTH: 352
<212> TYPE: PRT
<213> ORGANISM: Pseudomonas aeruginosa
<220> FEATURE:
<221> NAME/KEY: misc_feature
<223> OTHER INFORMATION: alginate regulatory protein AlgP
<221> NAME/KEY: misc_feature
<223> OTHER INFORMATION: gi[99]51563

<400> SEQUENCE: 23

Met Ser Ala Asn Lys Lys Pro Val Thr Thr Pro Leu His Leu Leu Gln
1               5                   10                  15

Gln Leu Ser His Ser Leu Val Glu His Leu Glu Gly Ala Cys Lys Gln
            20                  25                  30
```

Ala Leu Val Asp Ser Glu Lys Leu Leu Ala Lys Leu Glu Lys Gln Arg
         35                  40                  45

Gly Lys Ala Gln Glu Lys Leu His Lys Ala Arg Thr Lys Leu Gln Asp
     50                  55                  60

Ala Ala Lys Ala Gly Lys Thr Lys Ala Gln Ala Lys Ala Arg Glu Thr
65                  70                  75                  80

Ile Ser Asp Leu Glu Glu Ala Leu Asp Thr Leu Lys Ala Arg Gln Ala
                 85                  90                  95

Asp Thr Arg Thr Tyr Ile Val Gly Leu Lys Arg Asp Val Gln Glu Ser
             100                 105                 110

Leu Lys Leu Ala Gln Gly Val Gly Lys Val Lys Glu Ala Ala Gly Lys
         115                 120                 125

Ala Leu Glu Ser Arg Lys Ala Lys Pro Ala Thr Pro Ala Ala Lys
     130                 135                 140

Ala Ala Ala Lys Pro Ala Val Lys Thr Val Ala Ala Lys Pro Ala Ala
145                 150                 155                 160

Lys Pro Ala Ala Lys Pro Ala Ala Lys Pro Ala Ala Lys Pro Ala Ala
                 165                 170                 175

Lys Thr Ala Ala Ala Lys Pro Ala Ala Lys Pro Thr Ala Lys Pro Ala
             180                 185                 190

Ala Lys Pro Ala Ala Lys Pro Ala Ala Lys Thr Ala Ala Ala Lys Pro
         195                 200                 205

Ala Ala Lys Pro Ala Ala Lys Pro Val Ala Lys Pro Ala Ala Lys Pro
210                 215                 220

Ala Ala Lys Thr Ala Ala Lys Pro Ala Ala Lys Pro Ala Ala Lys
225                 230                 235                 240

Pro Val Ala Lys Pro Thr Ala Lys Pro Ala Ala Lys Thr Ala Ala Ala
                 245                 250                 255

Lys Pro Ala Ala Lys Pro Ala Ala Lys Pro Ala Ala Lys Pro Ala Ala
             260                 265                 270

Lys Pro Val Ala Lys Ser Ala Ala Lys Pro Ala Ala Lys Pro Ala
         275                 280                 285

Ala Lys Pro Ala Ala Lys Pro Ala Lys Pro Ala Ala Lys Pro Val
290                 295                 300

Ala Ala Lys Pro Ala Ala Thr Lys Pro Ala Thr Ala Pro Ala Ala Lys
305                 310                 315                 320

Pro Ala Ala Thr Pro Ser Ala Pro Ala Ala Ser Ser Ala Ala Ser
                 325                 330                 335

Ala Thr Pro Ala Ala Gly Ser Asn Gly Ala Pro Thr Ser Ala Ser
             340                 345                 350

<210> SEQ ID NO 24
<211> LENGTH: 309
<212> TYPE: PRT
<213> ORGANISM: Pseudomonas aeruginosa
<220> FEATURE:
<221> NAME/KEY: misc_feature
<223> OTHER INFORMATION: polyhydroxyalkanoate synthesis protein PhaF
<221> NAME/KEY: misc_feature
<223> OTHER INFORMATION: gi[99]51352

<400> SEQUENCE: 24

Met Ala Gly Lys Lys Ser Glu Lys Glu Ser Ser Trp Ile Gly Glu
1               5                   10                  15

Ile Glu Lys Tyr Ser Arg Gln Ile Trp Leu Ala Gly Leu Gly Ala Tyr
             20                  25                  30

```
Ser Lys Val Ser Lys Asp Gly Ser Lys Leu Phe Glu Thr Leu Val Lys
            35                  40                  45

Asp Gly Glu Lys Ala Glu Lys Glu Ala Lys Ser Asp Val Asp Ala Gln
 50                  55                  60

Val Gly Ala Ala Lys Ala Ser Ala Arg Ser Ala Lys Ser Lys Val Asp
 65                  70                  75                  80

Glu Val Arg Asp Arg Ala Leu Gly Lys Trp Ser Glu Leu Glu Glu Ala
                85                  90                  95

Phe Asp Lys Arg Leu Asn Ser Ala Ile Ser Arg Leu Gly Val Pro Ser
                100                 105                 110

Arg Asn Glu Val Lys Glu Leu His Ser Lys Val Asp Thr Leu Thr Lys
            115                 120                 125

Gln Ile Glu Lys Leu Thr Gly Val Ser Val Lys Pro Ala Ala Lys Ala
130                 135                 140

Ala Ala Lys Pro Ala Ala Lys Pro Ala Ala Lys Pro Ala Ala Lys Thr
145                 150                 155                 160

Ala Ala Ala Lys Pro Ala Ala Lys Pro Ala Lys Ala Ala Ala Lys
            165                 170                 175

Pro Ala Ala Lys Pro Ala Ala Lys Lys Thr Ala Ala Lys Thr Ala Ala
                180                 185                 190

Ala Lys Pro Ala Ala Lys Pro Ala Ala Lys Pro Thr Ala Lys Ala Ala
            195                 200                 205

Ala Lys Pro Ala Thr Lys Pro Ala Ala Lys Ala Ala Lys Pro Ala
            210                 215                 220

Ala Lys Pro Ala Ala Lys Pro Ala Ala Lys Pro Ala Ala Lys Pro
225                 230                 235                 240

Ala Ala Ala Thr Ala Ala Lys Pro Ala Ala Lys Pro Ala Ala Lys Pro
                245                 250                 255

Ala Ala Lys Lys Pro Ala Ala Lys Lys Pro Ala Ala Lys Pro Ala Ala
            260                 265                 270

Ala Lys Pro Ala Ala Pro Ala Ala Ser Ser Ser Ala Pro Ala Ala Pro
            275                 280                 285

Ala Ala Thr Pro Ala Ala Ser Ala Pro Ala Ala Asn Ala Pro Ala Thr
 290                 295                 300

Pro Ser Ser Gln Gly
305

<210> SEQ ID NO 25
<211> LENGTH: 632
<212> TYPE: PRT
<213> ORGANISM: T. pallidum
<220> FEATURE:
<221> NAME/KEY: misc_feature
<223> OTHER INFORMATION: dicarboxylate transporter (dctM)
<221> NAME/KEY: misc_feature
<223> OTHER INFORMATION: gi[33]23280

<400> SEQUENCE: 25

Met Lys Gly Thr Arg Gly Gln Leu Val Leu Arg Ser Ile Ala Leu Leu
 1                5                  10                  15

Leu Ile Gly Thr Leu Met Leu Leu Pro Leu Val Leu Phe Leu Ile Glu
            20                  25                  30

Arg Ile Phe Gly Phe Leu Thr Arg Gly Val Gly Ser Glu Val Phe Ser
            35                  40                  45

Ala His Glu Asp Phe Ile Phe Leu Phe Ser Ser Ser Asp Ala Ala
 50                  55                  60
```

-continued

```
Val Ala Gln Leu Ala Phe Val Phe Ser Cys Val Ala Gly Ile Tyr Ala
 65                  70                  75                  80

Ala Arg Glu Arg Lys His Leu Ser Val Thr Leu Phe Ser Cys Asp Val
                 85                  90                  95

Asp Arg Pro Met His Arg Val Leu Ser Phe Leu Ser Ala Ile Cys Thr
            100                 105                 110

Val Ala Val Leu Ser Ala Cys Phe Phe Ala Ser Gly Pro Asn Ile Val
        115                 120                 125

Ala Val Phe Arg Lys Glu Glu Ala Val Trp Gly Val Pro Leu Arg Trp
130                 135                 140

Ile Phe Thr Ala Leu Pro Cys Met Tyr Gly Ala Leu Leu Phe His Tyr
145                 150                 155                 160

Ala Arg Glu Val Lys Cys Arg Thr Cys Val Ile Val Gly Leu Leu Val
                165                 170                 175

Gly Val Leu Ile Ser Thr Gly Ser Ile Ala Ser Val Leu Phe His Leu
            180                 185                 190

Phe Asp Leu Thr Val Pro Leu Leu Asp Ser Val Phe His Gly Trp Val
        195                 200                 205

Ala Val Gly Thr Arg Leu Phe Trp Pro Phe Val Leu Leu Leu Leu Leu
210                 215                 220

Leu Ala Ala Gln Gly Leu Pro Leu Phe Ile Thr Leu Leu Ala Ile Ala
225                 230                 235                 240

Tyr Leu Ala Leu Ser Val Asp Gly Gly Tyr Val Asp Thr Leu Pro Leu
                245                 250                 255

Glu Gly Tyr Lys Ile Leu Thr Asp Thr Gly Ile Val Ala Val Pro
            260                 265                 270

Leu Phe Ala Thr Ala Ser Leu Leu Leu Ala Arg Gly Ser Thr Gly Thr
        275                 280                 285

Arg Leu Leu Arg Leu Val Lys Glu Ala Val Gly Trp Leu Arg Gly Gly
290                 295                 300

Ala Ala Val Ala Cys Val Ala Val Ala Ala Leu Phe Thr Ser Leu Thr
305                 310                 315                 320

Gly Val Ser Gly Val Thr Ile Leu Ala Leu Gly Ser Leu Phe Lys Leu
                325                 330                 335

Ile Leu Thr Gly Asn Lys Tyr Pro Glu His Asp Ala Glu Ala Leu Ile
            340                 345                 350

Thr Ser Ser Gly Ala Ile Gly Leu Leu Phe Pro Pro Ser Ala Ala Ile
        355                 360                 365

Ile Ile Phe Gly Ala Thr Asn Ile Leu Thr Val His Ile Val Asp Leu
370                 375                 380

Phe Lys Gly Ala Leu Leu Pro Gly Thr Leu Leu Val Leu Ser Ala Met
385                 390                 395                 400

Cys Leu Gly Val Ala Lys Asp Arg Thr Gln Val Arg Pro Ser Phe Ser
                405                 410                 415

Trp Gln Leu Leu Val His Ala Val Arg Gly Ser Val Phe Asp Leu Ala
            420                 425                 430

Leu Pro Val Cys Ile Ser Leu Gly Tyr Phe Ser Gly Thr Leu Asn Leu
        435                 440                 445

Leu Gln Cys Ala Ser Leu Thr Thr Leu Leu Ala Phe Val Leu Gly Thr
450                 455                 460

Trp Val Arg Arg Asp Phe Thr Val Lys Glu Ala Cys Ala Thr Ala Leu
465                 470                 475                 480
```

```
Glu Ser Leu Pro Ile Val Gly Ile Leu Ile Ile Val Ala Ala Ala
                485                 490                 495

Lys Gly Leu Ser Phe Tyr Leu Val Asp Ala Asn Val Pro Asp Thr Leu
                500                 505                 510

Ile Ala Phe Leu Gln His Ala Ile Ser Ser Lys Tyr Ala Phe Leu Leu
                515                 520                 525

Leu Leu Asn Val Leu Leu Gly Val Gly Cys Ile Met Asp Leu Tyr
        530                 535                 540

Ser Ala Ile Leu Val Ile Ser Pro Leu Val Leu Pro Leu Ala Val His
545                 550                 555                 560

Phe Gly Val His Pro Val His Ala Ser Val Val Phe Leu Met Asn Leu
                565                 570                 575

Glu Leu Gly Ala Leu Thr Pro Pro Ile Gly Met Asn Leu Phe Ile Ala
                580                 585                 590

Ser Phe Ala Phe Glu Lys Pro Ile Val Tyr Leu Thr Arg Ala Ile Ala
                595                 600                 605

Pro Phe Leu Leu Ala Gln Leu Gly Val Leu Leu Leu Thr Thr Tyr Ile
                610                 615                 620

Pro Trp Leu Ser Thr Ala Phe Leu
625                 630

<210> SEQ ID NO 26
<211> LENGTH: 653
<212> TYPE: PRT
<213> ORGANISM: Vibrio cholerae
<220> FEATURE:
<221> NAME/KEY: misc_feature
<223> OTHER INFORMATION: iron(III) ABC transporter, permease protein
<221> NAME/KEY: misc_feature
<223> OTHER INFORMATION: gi[96]54609

<400> SEQUENCE: 26

Met Ser Val Leu Arg Leu Thr Gly Leu Gly Ala Leu Thr Leu Leu Leu
1               5                   10                  15

Ala Leu Val Ser Leu Gln Trp Gly His Asn Leu Thr Leu Asn Glu Gln
                20                  25                  30

Trp Gln Leu Val Leu Gly His Gln Ala Ala Gln Ser Phe Ala Gln Val
            35                  40                  45

Asn Phe Ile Tyr Ala Gln Leu Pro Arg Ala Val Met Ala Ile Val Val
        50                  55                  60

Gly Ala Val Leu Gly Leu Val Gly Ser Leu Met Gln Gln Leu Thr Gln
65                  70                  75                  80

Asn Arg Leu Thr Ser Pro Leu Thr Leu Gly Thr Ser Ser Gly Ala Trp
                85                  90                  95

Leu Gly Leu Ile Ile Val Asn Ile Trp Phe Ser Asp Trp Val Ala Asp
                100                 105                 110

Tyr Ser Ala Leu Ala Ala Met Ala Gly Ala Leu Leu Ala Phe Ala Leu
                115                 120                 125

Ile Ile Ser Ile Ala Gly Leu Arg Asn Leu Thr Gly Leu Pro Leu Val
        130                 135                 140

Val Ser Gly Met Val Val Asn Ile Leu Leu Gly Ser Ile Ala Thr Ala
145                 150                 155                 160

Leu Val Leu Leu Asn Glu Glu Phe Ala Gln Asn Val Phe Met Trp Gly
                165                 170                 175

Ala Gly Asp Leu Ala Gln Asn Gly Trp Glu Trp Leu Thr Trp Leu Leu
                180                 185                 190
```

```
Pro Arg Leu Ala Leu Val Phe Pro Leu Leu Phe Ala Pro Arg Val
        195                 200                 205

Leu Thr Leu Leu Arg Leu Gly His Glu Gly Ala Ala Arg Gly Leu
        210                 215                 220

Ala Val Leu Pro Ala Phe Leu Phe Leu Met Ala Gly Gly Ile Trp Leu
225                 230                 235                 240

Val Ser Ala Ser Ile Thr Ala Val Gly Val Ile Gly Phe Ile Gly Leu
                245                 250                 255

Leu Thr Pro Asn Ile Ala Arg Ser Leu Gly Ala Arg Thr Thr Lys Met
            260                 265                 270

Glu Leu Tyr Ser Ser Ala Leu Leu Gly Ala Leu Leu Leu Leu Ala Thr
        275                 280                 285

Asp Met Leu Ala Met Gly Leu Ser Val Trp Ala Glu Glu Val Val Pro
290                 295                 300

Ser Gly Ile Thr Ala Ala Val Ile Gly Ala Pro Ala Leu Ile Trp Phe
305                 310                 315                 320

Ser Arg Arg Gln Leu Gln Ala Gln Asp Ser Leu Ser Ile Ser Leu Ser
                325                 330                 335

Ser His Arg Arg Ser Pro Ser Arg Trp Ala Val Met Leu Ile Ala Ala
            340                 345                 350

Ala Leu Leu Leu Ala Leu Ser Leu His Ile Gly Trp Gln Met Glu Ser
        355                 360                 365

Ala Ser Trp Ala Leu Pro Ser Glu Phe Gln Trp Pro Leu Arg Trp Pro
        370                 375                 380

Arg Met Leu Thr Ala Leu Phe Ala Gly Val Gly Leu Ala Ile Ala Gly
385                 390                 395                 400

Thr Leu Leu Gln Arg Leu Ile Tyr Asn Pro Leu Ala Ser Pro Asp Ile
                405                 410                 415

Leu Gly Val Ser Ser Gly Ala Thr Phe Ala Leu Val Phe Ala Ser Leu
            420                 425                 430

Phe Leu Gly Gln Ser Leu Gln Ser Thr His Trp Met Thr Ala Leu Leu
        435                 440                 445

Gly Ser Ala Ala Val Leu Val Ala Leu Leu Leu Gly Arg Arg His
        450                 455                 460

His Tyr Ala Pro Ser Ser Leu Ile Leu Thr Gly Ile Ala Ile Thr Ala
465                 470                 475                 480

Leu Leu Glu Ala Leu Val Gln Phe Thr Leu Ala Lys Gly Thr Gly Asp
                485                 490                 495

Ser Tyr Gln Ile Leu Leu Trp Leu Ser Gly Ser Thr Tyr Arg Ala Thr
            500                 505                 510

Gly Glu Gln Ala Leu Leu Ser Val Gly Val Gly Leu Thr Leu
        515                 520                 525

Leu Ala Leu Gly Leu Ser Arg Trp Leu Thr Leu Ile Ser Ile Gly Arg
        530                 535                 540

Gly Phe Ala Ser Ala Arg Gly Leu Ser Ala Ser Arg Ala Ser Leu Val
545                 550                 555                 560

Leu Leu Ile Leu Val Ala Leu Leu Cys Ala Leu Val Thr Ala Thr Met
                565                 570                 575

Gly Pro Val Ser Phe Val Gly Leu Ile Ala Pro His Met Ala Met Met
            580                 585                 590

Leu Gly Ala Gln Arg Ala Pro Ser Gln Leu Leu Ala Ala Leu Val
        595                 600                 605

Gly Gly Thr Leu Met Leu Trp Ala Asp Trp Leu Gly Gln Ala Leu Leu
```

-continued

```
        610                 615                 620
Phe Pro Ala Gln Ile Ala Ala Gly Thr Leu Val Ala Ile Ile Gly Gly
625                 630                 635                 640

Ser Tyr Phe Leu Leu Leu Leu Ser Gln Arg Ala Arg
                645                 650
```

<210> SEQ ID NO 27
<211> LENGTH: 356
<212> TYPE: PRT
<213> ORGANISM: Vibrio cholerae
<220> FEATURE:
<221> NAME/KEY: misc_feature
<223> OTHER INFORMATION: tolA protein
<221> NAME/KEY: misc_feature
<223> OTHER INFORMATION: gi[96]56364

<400> SEQUENCE: 27

```
Met Lys Glu Asn Lys Ser Arg Lys Ser Asn Asp Ala Lys Ser Ile Thr
1               5                  10                  15

Ile Ser Leu Ala Met His Gly Ala Leu Val Ala Ile Leu Leu Trp Gly
                20                  25                  30

Ala Asp Phe Thr Met Ser Asp Pro Glu Pro Thr Gly Gln Met Ile Glu
            35                  40                  45

Ala Val Val Ile Asp Pro Gln Leu Val Arg Gln Gln Ala Gln Gln Ile
        50                  55                  60

Arg Ser Gln Arg Glu Glu Ala Ala Lys Lys Glu Gln Glu Arg Leu Asp
65                  70                  75                  80

Lys Leu Arg Arg Glu Ser Glu Gln Leu Glu Lys Asn Arg Gln Ala Glu
                85                  90                  95

Glu Glu Arg Ile Arg Gln Leu Lys Glu Gln Ala Lys Glu Ala Lys
                100                 105                 110

Ala Ala Arg Glu Ala Glu Lys Leu Arg Glu Gln Lys Glu Gln Glu Arg
            115                 120                 125

Leu Ala Ala Glu Gln Lys Ala Arg Glu Glu Lys Glu Arg Ala Ala Lys
        130                 135                 140

Ala Glu Ala Glu Arg Lys Val Lys Glu Glu Ala Ala Lys Lys Ala Glu
145                 150                 155                 160

Gln Glu Arg Val Ala Lys Glu Ala Ala Ala Lys Ala Glu Gln Gln
                165                 170                 175

Arg Ile Glu Arg Glu Lys Glu Ala Lys Leu Ala Glu Glu Lys Ala Lys
            180                 185                 190

Arg Glu Lys Glu Val Ala Ala Lys Ala Glu Gln Glu Arg Leu Ala Lys
        195                 200                 205

Glu Lys Ala Ala Lys Glu Ala Asp Lys Ala Lys Lys Glu Lys Glu
        210                 215                 220

Arg Ala Ala Lys Ala Glu Ala Glu Arg Lys Ala Gln Glu Ala Ala Leu
225                 230                 235                 240

Asn Asp Ile Phe Gly Ser Leu Ser Glu Glu Ser Gln Gln Asn Asn Ala
                245                 250                 255

Ala Arg Gln Gln Phe Val Thr Ser Glu Val Gly Arg Tyr Gly Ala Ile
            260                 265                 270

Tyr Thr Gln Leu Ile Arg Gln Asn Leu Leu Val Glu Asp Ser Phe Arg
        275                 280                 285

Gly Lys Gln Cys Arg Val Asn Leu Lys Leu Ile Pro Thr Gly Thr Gly
        290                 295                 300

Ala Leu Leu Gly Ser Leu Thr Val Leu Asp Gly Asp Ser Arg Leu Cys
```

```
                305                 310                 315                 320
Ala Ala Thr Lys Arg Ala Val Ala Gln Val Asn Ser Phe Pro Leu Pro
                325                 330                 335

Lys Asp Gln Pro Asp Val Val Glu Lys Leu Lys Asn Ile Asn Leu Thr
                340                 345                 350

Val Ala Pro Glu
        355

<210> SEQ ID NO 28
<211> LENGTH: 73
<212> TYPE: PRT
<213> ORGANISM: L. major
<220> FEATURE:
<221> NAME/KEY: misc_feature
<223> OTHER INFORMATION: hydrophilic surface protein 2
<221> NAME/KEY: misc_feature
<223> OTHER INFORMATION: gi[17]43289

<400> SEQUENCE: 28

Met Gly Ser Ser Cys Thr Lys Asp Ser Ala Lys Glu Pro Gln Lys Ser
1               5                   10                  15

Ala Gly Asn Ile Asp Thr Thr Thr Arg Ser Glu Lys Asp Gly Val
                20                  25                  30

Leu Val Gln Gln Asn Asp Gly Asp Val Gln Lys Lys Ser Glu Asp Gly
            35                  40                  45

Asp Asn Val Gly Glu Gly Gly Lys Gly Asn Glu Asp Gly Asn Asp Asp
        50                  55                  60

Gln Pro Lys Glu His Ala Ala Gly Asn
65                  70

<210> SEQ ID NO 29
<211> LENGTH: 177
<212> TYPE: PRT
<213> ORGANISM: L. major
<220> FEATURE:
<221> NAME/KEY: misc_feature
<223> OTHER INFORMATION: hydrophilic surface protein
<221> NAME/KEY: misc_feature
<223> OTHER INFORMATION: gi[46]8328

<400> SEQUENCE: 29

Met Gly Ser Ser Cys Thr Lys Asp Ser Ala Lys Glu Pro Gln Lys Ser
1               5                   10                  15

Ala Asp Lys Ile Lys Ser Thr Asn Glu Thr Asn Gln Gly Gly Asn Ala
                20                  25                  30

Ser Gly Ser Arg Lys Ser Ala Gly Gly Arg Ala Asn Glu Tyr Asp Pro
            35                  40                  45

Lys Asp Gly Phe Thr Pro Asn Asn Glu Asp Arg Cys Pro Lys Glu
        50                  55                  60

Asp Gly His Ala Pro Lys Asn Asp Asp His Ala Pro Lys Glu Asp Gly
65                  70                  75                  80

His Ala Pro Lys Asn Asp Asp His Ala Pro Lys Glu Asp Gly His Ala
            85                  90                  95

Pro Lys Asn Asp Asp His Ala Pro Lys Glu Asp Gly His Ala Pro Lys
                100                 105                 110

Asn Asp Asp His Ala Pro Lys Glu Asp Gly His Ala Pro Lys Asn Asp
            115                 120                 125

Asp His Ala Pro Lys Glu Asp Gly His Ala Pro Lys Asn Asp Gly Asp
        130                 135                 140
```

```
Val Gln Lys Lys Ser Glu Asp Gly Asp Asn Val Gly Glu Gly Gly Lys
145                 150                 155                 160

Gly Asn Glu Asp Gly Asn Asp Asp Gln Pro Lys Glu His Ala Ala Gly
                165                 170                 175

Asn
```

<210> SEQ ID NO 30
<211> LENGTH: 106
<212> TYPE: PRT
<213> ORGANISM: Plasmodium falciparum
<220> FEATURE:
<221> NAME/KEY: misc_feature
<223> OTHER INFORMATION: predicted integral membrane protein
<221> NAME/KEY: misc_feature
<223> OTHER INFORMATION: gi[38]45179

<400> SEQUENCE: 30

```
Met Tyr Ile Cys Phe Phe Phe Phe Phe Phe Leu Val Ile Lys Leu
1               5                   10                  15

Gly Glu Asp Glu Asn Phe Gly Ser Ser Cys Phe Tyr Ser Leu Gly Asn
                20                  25                  30

Thr Lys Ile Leu Thr Thr Val Tyr Gly Pro Asn Pro Asp Ser Lys Tyr
            35                  40                  45

Ala Thr Tyr Ser Lys Gly Lys Val Phe Leu Asp Val Lys Ser Leu Asn
        50                  55                  60

Ile Asn Thr Ile Gly Ala Ser Asp Arg Val Leu Tyr Ile Tyr Gly Phe
65                  70                  75                  80

Phe Phe Phe Phe Phe Phe Phe Phe Phe Ile Leu Asn Arg Ser Tyr
                85                  90                  95

Phe Phe Leu Val Leu Phe Ile Ile Phe Ile
                100                 105
```

<210> SEQ ID NO 31
<211> LENGTH: 396
<212> TYPE: PRT
<213> ORGANISM: Plasmodium falciparum
<220> FEATURE:
<221> NAME/KEY: misc_feature
<223> OTHER INFORMATION: Circumsporozoite (CS) protein
<221> NAME/KEY: misc_feature
<223> OTHER INFORMATION: gi[44]93889

<400> SEQUENCE: 31

```
Met Arg Lys Leu Ala Ile Leu Ser Val Ser Ser Phe Leu Phe Val Glu
1               5                   10                  15

Ala Leu Phe Gln Glu Tyr Gln Cys Tyr Gly Ser Ser Ser Asn Thr Arg
                20                  25                  30

Val Leu Asn Glu Leu Asn Tyr Asp Asn Ala Gly Thr Asn Leu Tyr Asn
            35                  40                  45

Glu Leu Glu Met Asn Tyr Tyr Gly Lys Gln Glu Asn Trp Tyr Ser Leu
        50                  55                  60

Lys Lys Asn Ser Arg Ser Leu Gly Glu Asn Asp Asp Gly Asn Asn Glu
65                  70                  75                  80

Asp Asn Glu Lys Leu Arg Lys Pro Lys His Lys Lys Leu Lys Gln Pro
                85                  90                  95

Ala Asp Gly Asn Pro Asp Pro Asn Ala Asn Pro Asn Val Asp Pro Asn
            100                 105                 110

Ala Asn Pro Asn Val Asp Pro Asn Ala Asn Pro Asn Val Asp Pro Asn
            115                 120                 125
```

-continued

Ala Asn Pro Asn Ala Asn Pro Asn Ala Asn Pro Asn Ala Asn Pro Asn
        130                 135                 140

Ala Asn Pro Asn Ala Asn Pro Asn Ala Asn Pro Asn Ala Asn Pro Asn
145                 150                 155                 160

Ala Asn Pro Asn Ala Asn Pro Asn Ala Asn Pro Asn Ala Asn Pro Asn
            165                 170                 175

Ala Asn Pro Asn Ala Asn Pro Asn Ala Asn Pro Asn Ala Asn Pro Asn
        180                 185                 190

Ala Asn Pro Asn Val Asp Pro Asn Ala Asn Pro Asn Ala Asn Pro Asn
    195                 200                 205

Ala Asn Pro Asn Ala Asn Pro Asn Ala Asn Pro Asn Ala Asn Pro Asn
        210                 215                 220

Ala Asn Pro Asn Ala Asn Pro Asn Ala Asn Pro Asn Ala Asn Pro Asn
225                 230                 235                 240

Ala Asn Pro Asn Ala Asn Pro Asn Ala Asn Pro Asn Ala Asn Pro Asn
            245                 250                 255

Ala Asn Pro Asn Ala Asn Pro Asn Ala Asn Pro Asn Ala Asn Pro Asn
        260                 265                 270

Lys Asn Asn Gln Gly Asn Gly Gln Gly His Asn Met Pro Asn Asp Pro
    275                 280                 285

Asn Arg Asn Val Asp Glu Asn Ala Asn Ala Asn Ser Ala Val Lys Asn
290                 295                 300

Asn Asn Asn Glu Glu Pro Ser Asp Lys His Ile Lys Glu Tyr Leu Asn
305                 310                 315                 320

Lys Ile Gln Asn Ser Leu Ser Thr Glu Trp Ser Pro Cys Ser Val Thr
            325                 330                 335

Cys Gly Asn Gly Ile Gln Val Arg Ile Lys Pro Gly Ser Ala Asn Lys
        340                 345                 350

Pro Lys Asp Glu Leu Asp Tyr Ala Asn Asp Ile Glu Lys Lys Ile Cys
    355                 360                 365

Lys Met Glu Lys Cys Ser Ser Val Phe Asn Val Val Asn Ser Ser Ile
370                 375                 380

Gly Leu Ile Met Val Leu Ser Phe Leu Phe Leu Asn
385                 390                 395

<210> SEQ ID NO 32
<211> LENGTH: 497
<212> TYPE: PRT
<213> ORGANISM: B. burgdorferi
<220> FEATURE:
<221> NAME/KEY: misc_feature
<223> OTHER INFORMATION: predicted coding region BB0553
<221> NAME/KEY: misc_feature
<223> OTHER INFORMATION: "Xaa" may be any amino acid
<221> NAME/KEY: misc_feature
<223> OTHER INFORMATION: gi[26]88482

<400> SEQUENCE: 32

Met Asn Lys Thr Lys Asn Arg Ser Leu Thr Tyr Phe Ile Ile Leu Ser
1               5                   10                  15

Cys Ile Ser Leu Phe Gly Ala Asn Asn Thr Ile Ser Tyr Ser Ser
            20                  25                  30

Ile Glu Ile Pro Leu Glu Asp Leu Ser Glu Glu Phe Lys Ser Ser Gly
        35                  40                  45

Asn Lys Ser Asp Gln Ile Asn Thr Ser Lys His Leu Asn Lys Asn Ile
    50                  55                  60

Val Ser Tyr Glu Asp Pro Lys Lys Gly Lys Asp Leu Lys Leu Pro Glu

```
                65                  70                  75                  80
Asn Ile Arg Asp Lys Lys Leu Pro Gln Lys Arg Met Asp Glu Asn Asp
                    85                  90                  95

Leu Lys Ser Val Ile Glu Asn Tyr Glu Asn Lys Ile Lys Asn Ile Glu
                100                 105                 110

Lys Leu Leu Lys Thr Lys Asn Gln Lys Thr Ser Glu Asn Glu Asn Lys
                115                 120                 125

Lys Ile Glu Ser Ile Glu Lys Lys Ala Lys Lys Tyr Glu Ile Leu Thr
            130                 135                 140

Asn Lys Leu Lys Asn Glu Ile Val Glu Ile Lys Lys Leu Leu Asn Lys
145                 150                 155                 160

Lys Ile Lys Pro Lys Glu Asp Glu Asn Tyr Glu Lys Ile Asn Ile Glu
                165                 170                 175

Asn Ile Glu Glu Glu Thr Asp Asp Phe Glu Asp Asn Tyr Glu Tyr
                180                 185                 190

Asn Asp Glu Ile Glu Xaa Thr Asn Glu Asp Asn Tyr Pro Ser Asn Glu
            195                 200                 205

Gly Ile Ile Asn Asn Leu Lys Glu Asn Leu Asn Glu Asn Gly Lys Tyr
            210                 215                 220

Tyr Ala Ile Asn Glu Lys Lys Ile Asp Glu Leu Glu Asp Arg Ile Asn
225                 230                 235                 240

Glu Asn Glu Asn Thr Ile Leu Asp Leu Gln Arg Glu Leu Arg Asn Phe
                245                 250                 255

Lys Lys Lys Asp Asn Ser Asp Lys Asn Leu Glu Glu Ile Glu Glu Asn
            260                 265                 270

Leu Ser Ser Ile Gly Arg Ile Ile Asn Asp Leu Lys Arg Lys Ile Ser
            275                 280                 285

Ala Asn Glu Ala Ile Asn Lys Glu Asn Gln Lys Lys Ile Arg Thr Asp
            290                 295                 300

Lys His Lys Leu Lys Glu Leu Glu Asp Lys Ile Lys Glu Asn Glu Glu
305                 310                 315                 320

Thr Ile Leu Lys Leu Gln Lys Glu Leu Asn Asn Phe Lys Lys Lys Glu
                325                 330                 335

Ile Tyr Gln Lys Pro Leu Asn Glu Glu Thr Phe Thr Pro Ser Ile Thr
            340                 345                 350

Ser Lys Asn Asp Asp Leu Glu Glu Asn Lys Lys Leu Lys Lys Glu Tyr
            355                 360                 365

Leu Lys Pro Ile Glu Lys Lys Glu Ser Arg Asp Leu Glu Glu Asn Thr
            370                 375                 380

Lys Ser Thr Pro Lys Thr Thr Met Ile Lys Thr Ala Asp Phe Gln Ile
385                 390                 395                 400

Tyr Pro Asp Ile Tyr Leu Asn Asn Tyr Lys Phe Lys Glu Lys Gly Asp
                405                 410                 415

Gln Phe Ala Phe Lys Lys Glu Asn Thr Tyr Tyr Ile Glu Ile Asp Pro
            420                 425                 430

Thr Asn Asn Leu Asn Glu Ala Leu Lys Asn His Glu Ile Ile Ser Lys
            435                 440                 445

Tyr Lys Phe Glu Lys Tyr Phe Ile Asn Pro Ile Leu Lys Asn Lys Glu
            450                 455                 460

Glu Phe Phe Arg Asn Leu Ile Glu Val Lys Asn Ile His Glu Leu Gly
465                 470                 475                 480

Ile Met Tyr Lys Asn Leu Lys Pro Glu Phe Lys Gln Ile Lys Ile Ile
                485                 490                 495
```

Lys

<210> SEQ ID NO 33
<211> LENGTH: 31
<212> TYPE: PRT
<213> ORGANISM: B. burgdorferi
<220> FEATURE:
<221> NAME/KEY: misc_feature
<223> OTHER INFORMATION: predicted coding region BB0148
<221> NAME/KEY: misc_feature
<223> OTHER INFORMATION: gi[26]88046

<400> SEQUENCE: 33

Met Pro Val Lys Lys Asn Ser Thr Lys Ile Lys Lys Glu Thr Gln
1               5                   10                  15

Ile Ala Ile Ala Leu Lys Ile Ile Ile Ile Tyr Phe Phe Asp
            20                  25                  30

<210> SEQ ID NO 34
<211> LENGTH: 30
<212> TYPE: PRT
<213> ORGANISM: B. burgdorferi
<220> FEATURE:
<221> NAME/KEY: misc_feature
<223> OTHER INFORMATION: predicted coding region BB0150
<221> NAME/KEY: misc_feature
<223> OTHER INFORMATION: gi[26]88045

<400> SEQUENCE: 34

Met Phe Gly Cys Leu Arg Ile His Val Phe Lys Ile Tyr Phe Ile Phe
1               5                   10                  15

Leu Ile Ile His Tyr Ile Leu Phe Ser Ile Leu Leu Met Ile
            20                  25                  30

<210> SEQ ID NO 35
<211> LENGTH: 344
<212> TYPE: PRT
<213> ORGANISM: B. burgdorferi
<220> FEATURE:
<221> NAME/KEY: misc_feature
<223> OTHER INFORMATION: predicted coding region BB0212
<221> NAME/KEY: misc_feature
<223> OTHER INFORMATION: gi[26]88103

<400> SEQUENCE: 35

Met Met Lys Lys Ile Lys Ser Glu Ile Asn Leu Leu Lys Ile Glu Lys
1               5                   10                  15

Asp Lys Asn Leu Ile Glu Leu Gly Lys Ile Leu Lys Asn Asn Asn Ile
            20                  25                  30

Val Glu Leu Lys Asn Leu Asn His Tyr Pro Asn Leu Lys Leu Val Glu
        35                  40                  45

Lys Glu Leu Tyr Gln Met Lys Ser Asn Leu Ser Lys Ser Glu Glu Asn
    50                  55                  60

Glu Asn Ile Leu Lys Asn Leu Asn Lys Lys Ile Tyr Ile Leu Lys Lys
65                  70                  75                  80

Glu Tyr Lys Ser Thr Ser Lys Ser Tyr Lys Lys Asn Leu Lys Glu Ile
                85                  90                  95

Ala Lys Thr Ile Ile Glu Ile Tyr Pro Gln Asn Leu Glu Leu Ile Ser
            100                 105                 110

Lys Tyr Asn Met Asn Phe Ser Lys Leu Lys Leu Glu Lys Tyr Lys Lys
        115                 120                 125

Ile Glu Leu Ala Ser Asp His Lys Thr Lys Asn Tyr Leu Gln Arg Ile

```
            130                 135                 140
Met Leu Glu Val Ser Ser Thr Ile Asn Asn Ile Asn Met Ile Asn
145                 150                 155                 160

Val Tyr Lys Ile Ser Lys Glu Phe Glu Lys Gln Val Phe Thr Lys Tyr
                165                 170                 175

Tyr Pro Ser Glu Asn Phe Glu Ser Ile Met Asn Glu Phe Ser Leu Asn
                180                 185                 190

Lys Lys Leu Asn Asn Val Ile Val Lys Glu Phe Lys Ile Ile Asn Glu
            195                 200                 205

Ile Lys Thr Asn Ile Lys Asn Ile Lys Glu Glu Ile Lys Glu Ile Ile
        210                 215                 220

Ser Thr Ser Lys Lys Glu Lys Ile Tyr Lys Lys Asn Thr Ile Lys Asn
225                 230                 235                 240

Glu Ile Asn Val Ile Thr Lys Asn Lys Glu Asn Ile Leu Lys Lys Ile
                245                 250                 255

Ala Glu Glu Phe Ile Glu Ile Thr Lys Lys Asp Lys Met Thr Ala Lys
                260                 265                 270

Thr Asn Ala Ile Ser Ser Ile Ile Gln Lys Ile Glu Lys Ile Asn Gln
            275                 280                 285

Lys Ile Leu Asn Leu Asn Asn Asp Leu Ile Lys Ile Thr Lys Gln Glu
        290                 295                 300

Glu Ile Lys Asn Ile Gln Gln Lys Ile Gln Ala Leu Thr Lys Glu Lys
305                 310                 315                 320

Asn Lys Ile Asn Asn Lys Leu Asp Ala Leu Thr Ser Lys Ile Glu Val
                325                 330                 335

Ile Gln Asn Glu Leu Asp Asn Glu
            340

<210> SEQ ID NO 36
<211> LENGTH: 30
<212> TYPE: PRT
<213> ORGANISM: B. burgdorferi
<220> FEATURE:
<221> NAME/KEY: misc_feature
<223> OTHER INFORMATION: predicted coding region BB0425
<221> NAME/KEY: misc_feature
<223> OTHER INFORMATION: gi[26]88333

<400> SEQUENCE: 36

Met Glu Asp Glu Arg Arg Glu Glu Leu Ser Lys Val Lys Ser Gln Lys
1               5                   10                  15

Asn Lys Gln Asn Leu Leu Ile Phe Leu Asn Lys Lys Ile Lys
            20                  25                  30

<210> SEQ ID NO 37
<211> LENGTH: 32
<212> TYPE: PRT
<213> ORGANISM: B. burgdorferi
<220> FEATURE:
<221> NAME/KEY: misc_feature
<223> OTHER INFORMATION: predicted coding region BB0433
<221> NAME/KEY: misc_feature
<223> OTHER INFORMATION: gi[26]88343

<400> SEQUENCE: 37

Met His Lys Phe Phe Lys Leu Ile Leu Lys Leu Phe Ser Phe Tyr Lys
1               5                   10                  15

Glu Ile Leu Gly Phe Lys Arg Arg Ala Lys Phe Ile Phe Cys Tyr Leu
            20                  25                  30
```

```
<210> SEQ ID NO 38
<211> LENGTH: 38
<212> TYPE: PRT
<213> ORGANISM: B. burgdorferi
<220> FEATURE:
<221> NAME/KEY: misc_feature
<223> OTHER INFORMATION: predicted coding region BB0520
<221> NAME/KEY: misc_feature
<223> OTHER INFORMATION: gi[26]88447

<400> SEQUENCE: 38

Met Ser Lys Ser Thr Lys Asn Thr Thr Lys Ser Lys Asn Asp Thr Lys
1               5                   10                  15

Asn Ile Leu Ile Asn Lys Lys Ile Lys Phe Phe Ile Leu Thr Lys Lys
            20                  25                  30

Tyr Thr Arg Thr Phe Tyr
        35

<210> SEQ ID NO 39
<211> LENGTH: 36
<212> TYPE: PRT
<213> ORGANISM: B. burgdorferi
<220> FEATURE:
<221> NAME/KEY: misc_feature
<223> OTHER INFORMATION: predicted coding region BB0609
<221> NAME/KEY: misc_feature
<223> OTHER INFORMATION: gi[26]88540

<400> SEQUENCE: 39

Met Thr Met Ile Ile Ile Ile Phe Tyr Lys Tyr Leu Ile Pro Lys Ser
1               5                   10                  15

Ile Lys Asp Lys Asn Asn Lys Ser His Lys Thr Phe Ile Lys Lys Phe
            20                  25                  30

Ile Ile Lys Tyr
        35

<210> SEQ ID NO 40
<211> LENGTH: 31
<212> TYPE: PRT
<213> ORGANISM: B. burgdorferi
<220> FEATURE:
<221> NAME/KEY: misc_feature
<223> OTHER INFORMATION: predicted coding region BB0822
<221> NAME/KEY: misc_feature
<223> OTHER INFORMATION: gi[26]88768

<400> SEQUENCE: 40

Met Pro Cys Gly Arg Lys Arg Lys Leu Lys Lys Ile Ser Thr His Lys
1               5                   10                  15

Arg Lys Lys Lys Arg Arg Lys Asn Arg His Lys Lys Lys Asn Lys
            20                  25                  30

<210> SEQ ID NO 41
<211> LENGTH: 34
<212> TYPE: PRT
<213> ORGANISM: B. burgdorferi
<220> FEATURE:
<221> NAME/KEY: misc_feature
<223> OTHER INFORMATION: predicted coding region BB0848
<221> NAME/KEY: misc_feature
<223> OTHER INFORMATION: gi[26]88793

<400> SEQUENCE: 41

Met Tyr Phe Cys Ile Ile Asp Leu Glu Phe Val Gly Val Leu Pro Tyr
1               5                   10                  15
```

```
Phe Phe Ile Tyr Lys Phe Gly Glu Phe Tyr Phe Ser Phe Phe Gly Lys
             20                  25                  30

Trp Arg
```

<210> SEQ ID NO 42
<211> LENGTH: 51
<212> TYPE: PRT
<213> ORGANISM: C. jejuni
<220> FEATURE:
<221> NAME/KEY: misc_feature
<223> OTHER INFORMATION: highly acidic protein
<221> NAME/KEY: misc_feature
<223> OTHER INFORMATION: gi[69]67728

<400> SEQUENCE: 42

```
Met Ala Tyr Glu Asp Glu Glu Asp Leu Asn Tyr Asp Asp Tyr Glu Asn
1               5                   10                  15

Glu Asp Glu Glu Tyr Pro Gln Asn His His Lys Asn Tyr Asn Tyr Asp
             20                  25                  30

Asp Asp Asp Tyr Glu Tyr Asp Asp Asp Asn Asn Asp Asp Asp Phe Tyr
         35                  40                  45

Glu Met Asp
     50
```

<210> SEQ ID NO 43
<211> LENGTH: 41
<212> TYPE: PRT
<213> ORGANISM: C. jejuni
<220> FEATURE:
<221> NAME/KEY: misc_feature
<223> OTHER INFORMATION: hypothetical protein Cj0344
<221> NAME/KEY: misc_feature
<223> OTHER INFORMATION: gi[69]67819

<400> SEQUENCE: 43

```
Met Phe Gln Asn Ile Ile Lys Tyr Lys Asp Phe Ile Ile Phe Ile Leu
1               5                   10                  15

Asn Leu Lys Gln Asn Leu Tyr Leu Leu Ile Lys Ile Asn Leu Asp Phe
             20                  25                  30

Lys Asn Phe His Lys Ser Leu Asn Phe
         35                  40
```

<210> SEQ ID NO 44
<211> LENGTH: 37
<212> TYPE: PRT
<213> ORGANISM: C. jejuni
<220> FEATURE:
<221> NAME/KEY: misc_feature
<223> OTHER INFORMATION: hypothetical protein Cj0567
<221> NAME/KEY: misc_feature
<223> OTHER INFORMATION: gi[69]68034

<400> SEQUENCE: 44

```
Met Asp Lys Ile Gln Glu Asn Thr Lys Ile Glu Lys Ala Ile Leu Ala
1               5                   10                  15

Glu Lys Gln Gln Ile Phe Leu Ile Gln Asn Lys Leu Ser Glu Ile Glu
             20                  25                  30

Lys Asn Ile Lys Glu
         35
```

<210> SEQ ID NO 45
<211> LENGTH: 74
<212> TYPE: PRT
<213> ORGANISM: C. jejuni

```
<220> FEATURE:
<221> NAME/KEY: misc_feature
<223> OTHER INFORMATION: small hydrophobic protein
<221> NAME/KEY: misc_feature
<223> OTHER INFORMATION: gi[69]68265

<400> SEQUENCE: 45

Met Leu Glu Phe Ile Phe Thr Leu Ile Leu Asp Phe Thr Phe Tyr Ser
1               5                   10                  15

Ile Lys Thr Leu Glu Lys Val Phe Leu Gly Arg Thr Ala Leu Val Ile
                20                  25                  30

Leu Phe Val Val Phe Ile Ala Leu Phe Cys Val Lys Gly Leu Phe Leu
            35                  40                  45

Tyr Ile Leu Leu Ala Leu Glu Leu Phe Leu Leu Tyr Leu Phe Leu
    50                  55                  60

Gly Ile Leu Phe Leu Arg Phe Tyr Lys Ser
65                  70

<210> SEQ ID NO 46
<211> LENGTH: 46
<212> TYPE: PRT
<213> ORGANISM: C. jejuni
<220> FEATURE:
<221> NAME/KEY: misc_feature
<223> OTHER INFORMATION: very hypothetical protein Cj0974
<221> NAME/KEY: misc_feature
<223> OTHER INFORMATION: gi[69]68409

<400> SEQUENCE: 46

Met Leu Lys Met Ile Lys Ile Gln Lys Val Lys Ser Leu Leu Asp Leu
1               5                   10                  15

Val Lys Lys Leu Lys Asn Lys Gln Ser Leu Lys Ile Lys Asn Gln Thr
                20                  25                  30

Asn Thr Lys Glu Asn Leu Asn Lys Thr His Tyr Leu Thr Ile
            35                  40                  45

<210> SEQ ID NO 47
<211> LENGTH: 78
<212> TYPE: PRT
<213> ORGANISM: C. jejuni
<220> FEATURE:
<221> NAME/KEY: misc_feature
<223> OTHER INFORMATION: very hypothetical protein
<221> NAME/KEY: misc_feature
<223> OTHER INFORMATION: gi[69]68423

<400> SEQUENCE: 47

Met Leu Lys Ile Pro Tyr Phe Ser Phe Leu Lys Leu Asp Phe Glu Ile
1               5                   10                  15

Tyr His Leu Asn Thr Ser Lys Asn Phe Tyr Gly Phe Phe Ile Leu Tyr
                20                  25                  30

Phe Ser Phe Phe Ile Phe Lys Leu Ile Tyr Lys Phe Ser Lys Ser Asn
            35                  40                  45

Lys Lys Ile Tyr Lys Lys Ile Ile Leu Lys Ile Ile Lys Asp
    50                  55                  60

Asn Lys Tyr Leu Ile Phe Leu Cys Tyr Ile Leu Ile Asn Ile
65                  70                  75

<210> SEQ ID NO 48
<211> LENGTH: 30
<212> TYPE: PRT
<213> ORGANISM: C. jejuni
<220> FEATURE:
```

-continued

```
<221> NAME/KEY: misc_feature
<223> OTHER INFORMATION: hypothetical protein Cj0748
<221> NAME/KEY: misc_feature
<223> OTHER INFORMATION: gi[69]68200

<400> SEQUENCE: 48

Met Leu Glu Thr Leu Lys Lys Tyr Ala Glu Asn Gln Gly Ile Glu Asp
1               5                   10                  15

Asn Tyr Pro Lys Lys Ile Tyr Asn Gln Lys Gly Lys Lys Pro
            20                  25                  30

<210> SEQ ID NO 49
<211> LENGTH: 168
<212> TYPE: PRT
<213> ORGANISM: C. pneumoniae CWL029
<220> FEATURE:
<221> NAME/KEY: misc_feature
<223> OTHER INFORMATION: CT670 hypothetical protein
<221> NAME/KEY: misc_feature
<223> OTHER INFORMATION: gi[43]77009

<400> SEQUENCE: 49

Met Ala Lys Tyr Pro Leu Glu Pro Val Leu Ala Ile Lys Lys Asp Arg
1               5                   10                  15

Val Asp Arg Ala Glu Lys Val Val Lys Glu Lys Arg Leu Leu Glu
            20                  25                  30

Ile Glu Gln Glu Lys Leu Arg Glu Lys Ala Glu Arg Asp Lys Val
            35                  40                  45

Lys Asn His Tyr Met Gln Lys Ile Gln Gln Leu Arg Asp Leu Leu Asp
50                  55                  60

Glu Gly Thr Thr Ser Asp Ala Val Leu Gln Ile Lys Ser Tyr Ile Lys
65                  70                  75                  80

Val Val Ala Val Gln Leu Ser Glu Glu Glu Lys Val Asn Lys Gln
            85                  90                  95

Lys Glu Val Val Leu Ala Ala Ser Glu Leu Glu Lys Ala Glu Val
            100                 105                 110

Asn Leu Ala Lys Arg Arg Lys Glu Glu Glu Lys Thr Arg Leu His Lys
            115                 120                 125

Glu Glu Trp Met Lys Glu Ala Leu Lys Glu Glu Ala Arg Ala Glu Glu
130                 135                 140

Lys Glu Gln Asp Glu Met Gly Gln Leu Leu Phe Gln Leu Arg Gln Lys
145                 150                 155                 160

Lys Lys Arg Glu Ser Gly Gly Ser
            165

<210> SEQ ID NO 50
<211> LENGTH: 444
<212> TYPE: PRT
<213> ORGANISM: C. pneumoniae CWL029
<220> FEATURE:
<221> NAME/KEY: misc_feature
<223> OTHER INFORMATION: CT579 hypothetical protein
<221> NAME/KEY: misc_feature
<223> OTHER INFORMATION: gi[43]77120

<400> SEQUENCE: 50

Met Thr Ser Gly Val Ser Gly Ser Ser Gln Asp Pro Thr Leu Ala
1               5                   10                  15

Ala Gln Leu Ala Gln Ser Ser Gln Lys Ala Gly Asn Ala Gln Ser Gly
            20                  25                  30

His Asp Thr Lys Asn Val Thr Lys Gln Gly Ala Gln Ala Glu Val Ala
```

-continued

```
                35                  40                  45
Ala Gly Gly Phe Glu Asp Leu Ile Gln Asp Ala Ser Ala Gln Ser Thr
 50                  55                  60
Gly Lys Lys Glu Ala Thr Ser Ser Thr Thr Lys Ser Ser Lys Gly Glu
 65                  70                  75                  80
Lys Ser Glu Lys Ser Gly Lys Ser Lys Ser Ser Thr Ser Val Ala Ser
                 85                  90                  95
Ala Ser Glu Thr Ala Thr Ala Gln Ala Val Gln Gly Pro Lys Gly Leu
                100                 105                 110
Arg Gln Asn Asn Tyr Asp Ser Pro Ser Leu Pro Thr Pro Glu Ala Gln
                115                 120                 125
Thr Ile Asn Gly Ile Val Leu Lys Lys Gly Met Gly Thr Leu Ala Leu
                130                 135                 140
Leu Gly Leu Val Met Thr Leu Met Ala Asn Ala Ala Gly Glu Ser Trp
145                 150                 155                 160
Lys Ala Ser Phe Gln Ser Gln Asn Gln Ala Ile Arg Ser Gln Val Glu
                165                 170                 175
Ser Ala Pro Ala Ile Gly Glu Ala Ile Lys Arg Gln Ala Asn His Gln
                180                 185                 190
Ala Ser Ala Thr Glu Ala Gln Ala Lys Gln Ser Leu Ile Ser Gly Ile
                195                 200                 205
Val Asn Ile Val Gly Phe Thr Val Ser Val Gly Ala Gly Ile Phe Ser
                210                 215                 220
Ala Ala Lys Gly Ala Thr Ser Ala Leu Lys Ser Ala Ser Phe Ala Lys
225                 230                 235                 240
Glu Thr Gly Ala Ser Ala Ala Gly Gly Ala Ala Ser Lys Ala Leu Thr
                245                 250                 255
Ser Ala Ser Ser Ser Val Gln Gln Thr Met Ala Ser Thr Ala Lys Ala
                260                 265                 270
Ala Thr Thr Ala Ala Ser Ser Ala Gly Ser Ala Ala Thr Lys Ala Ala
                275                 280                 285
Ala Asn Leu Thr Asp Asp Met Ala Ala Ala Ser Lys Met Ala Ser
                290                 295                 300
Asp Gly Ala Ser Lys Ala Ser Gly Gly Leu Phe Gly Glu Val Leu Asn
305                 310                 315                 320
Lys Pro Asn Trp Ser Glu Lys Val Ser Arg Gly Met Asn Val Lys
                325                 330                 335
Thr Gln Gly Ala Arg Val Ala Ser Phe Ala Gly Asn Ala Leu Ser Ser
                340                 345                 350
Ser Met Gln Met Ser Gln Leu Met His Gly Leu Thr Ala Ala Val Glu
                355                 360                 365
Gly Leu Ser Ala Gly Gln Thr Gly Ile Glu Val Ala His His Gln Arg
370                 375                 380
Leu Ala Gly Gln Ala Glu Ala Gln Ala Glu Val Leu Lys Gln Met Ser
385                 390                 395                 400
Ser Val Tyr Gly Gln Gln Ala Gly Gln Ala Gly Gln Leu Gln Glu Gln
                405                 410                 415
Ala Met Gln Ser Phe Asn Thr Ala Leu Gln Thr Leu Gln Asn Ile Ala
                420                 425                 430
Asp Ser Gln Thr Gln Thr Thr Ser Ala Ile Phe Asn
                435                 440
```

<210> SEQ ID NO 51

```
<211> LENGTH: 493
<212> TYPE: PRT
<213> ORGANISM: C. pneumoniae CWL029
<220> FEATURE:
<221> NAME/KEY: misc_feature
<223> OTHER INFORMATION: CT578 hypothetical protein
<221> NAME/KEY: misc_feature
<223> OTHER INFORMATION: gi[43]77121

<400> SEQUENCE: 51
```

| Met | Ser | Ile | Ser | Ser | Ser | Gly | Pro | Asp | Asn | Gln | Lys | Asn | Ile | Met |
|---|---|---|---|---|---|---|---|---|---|---|---|---|---|---|
| 1 | | | | 5 | | | | | 10 | | | | | 15 |

Ser Gln Val Leu Thr Ser Thr Pro Gln Gly Val Pro Gln Gln Asp Lys
            20                  25                  30

Leu Ser Gly Asn Glu Thr Lys Gln Ile Gln Gln Thr Arg Gln Gly Lys
            35                  40                  45

Asn Thr Glu Met Glu Ser Asp Ala Thr Ile Ala Gly Ala Ser Gly Lys
    50                  55                  60

Asp Lys Thr Ser Ser Thr Thr Lys Thr Glu Thr Ala Pro Gln Gln Gly
65                  70                  75                  80

Val Ala Ala Gly Lys Glu Ser Ser Glu Ser Gln Lys Ala Gly Ala Asp
                85                  90                  95

Thr Gly Val Ser Gly Ala Ala Ala Thr Thr Ala Ser Asn Thr Ala Thr
            100                 105                 110

Lys Ile Ala Met Gln Thr Ser Ile Glu Glu Ala Ser Lys Ser Met Glu
            115                 120                 125

Ser Thr Leu Glu Ser Leu Gln Ser Leu Ser Ala Ala Gln Met Lys Glu
    130                 135                 140

Val Glu Ala Val Val Val Ala Ala Leu Ser Gly Lys Ser Ser Gly Ser
145                 150                 155                 160

Ala Lys Leu Glu Thr Pro Glu Leu Pro Lys Pro Gly Val Thr Pro Arg
                165                 170                 175

Ser Glu Val Ile Glu Ile Gly Leu Ala Leu Lys Ala Ile Gln Thr
            180                 185                 190

Leu Gly Glu Ala Thr Lys Ser Ala Leu Ser Asn Tyr Ala Ser Thr Gln
            195                 200                 205

Ala Gln Ala Asp Gln Thr Asn Lys Leu Gly Leu Glu Lys Gln Ala Ile
    210                 215                 220

Lys Ile Asp Lys Glu Arg Glu Glu Tyr Gln Glu Met Lys Ala Ala Glu
225                 230                 235                 240

Gln Lys Ser Lys Asp Leu Glu Gly Thr Met Asp Thr Val Asn Thr Val
                245                 250                 255

Met Ile Ala Val Ser Val Ala Ile Thr Val Ile Ser Ile Val Ala Ala
            260                 265                 270

Ile Phe Thr Cys Gly Ala Gly Leu Ala Gly Leu Ala Ala Gly Ala Ala
            275                 280                 285

Val Gly Ala Ala Ala Gly Ala Ala Gly Ala Ala Ala Ala Thr
    290                 295                 300

Thr Val Ala Thr Gln Ile Thr Val Gln Ala Val Val Gln Ala Val Lys
305                 310                 315                 320

Gln Ala Val Ile Thr Ala Val Arg Gln Ala Ile Thr Ala Ala Ile Lys
                325                 330                 335

Ala Ala Val Lys Ser Gly Ile Lys Ala Phe Ile Lys Thr Leu Val Lys
            340                 345                 350

Ala Ile Ala Lys Ala Ile Ser Lys Gly Ile Ser Lys Val Phe Ala Lys
            355                 360                 365

```
Gly Thr Gln Met Ile Ala Lys Asn Phe Pro Lys Leu Ser Lys Val Ile
    370                 375                 380

Ser Ser Leu Thr Ser Lys Trp Val Thr Val Gly Val Gly Val Val
385                 390                 395                 400

Ala Ala Pro Ala Leu Gly Lys Gly Ile Met Gln Met Gln Leu Ser Glu
                405                 410                 415

Met Gln Gln Asn Val Ala Gln Phe Gln Lys Glu Val Gly Lys Leu Gln
            420                 425                 430

Ala Ala Ala Asp Met Ile Ser Met Phe Thr Gln Phe Trp Gln Gln Ala
            435                 440                 445

Ser Lys Ile Ala Ser Lys Gln Thr Gly Glu Ser Asn Glu Met Thr Gln
    450                 455                 460

Lys Ala Thr Lys Leu Gly Ala Gln Ile Leu Lys Ala Tyr Ala Ala Ile
465                 470                 475                 480

Ser Gly Ala Ile Ala Gly Ala His Lys Thr Asn Asn Phe
                485                 490

<210> SEQ ID NO 52
<211> LENGTH: 76
<212> TYPE: PRT
<213> ORGANISM: C. pneumoniae CWL029
<220> FEATURE:
<221> NAME/KEY: misc_feature
<223> OTHER INFORMATION: CT753 hypothetical protein
<221> NAME/KEY: misc_feature
<223> OTHER INFORMATION: gi[43]77216

<400> SEQUENCE: 52

Met Arg Asn Met Glu Ala Lys Lys Ile Lys Glu Leu Ser Lys Glu Ala
1               5                   10                  15

Gln Leu Leu Lys Lys Leu Arg Glu Lys Ser Arg Val Leu Asp Glu Lys
            20                  25                  30

Asn Lys Arg Lys Ala Trp Val Ala Lys Leu Val Ala Met Pro Glu Ser
        35                  40                  45

Ile Arg Glu Ile Glu Lys Glu Glu Arg Val Glu Thr Pro Gln Leu Phe
    50                  55                  60

Gln Ala Ile Ala Glu Lys Ile Leu Glu Glu Gly Val
65                  70                  75

<210> SEQ ID NO 53
<211> LENGTH: 755
<212> TYPE: PRT
<213> ORGANISM: C. pneumoniae CWL029
<220> FEATURE:
<221> NAME/KEY: misc_feature
<223> OTHER INFORMATION: CT456 hypothetical protein
<221> NAME/KEY: misc_feature
<223> OTHER INFORMATION: gi[43]76866

<400> SEQUENCE: 53

Met Ala Ala Pro Ile Asn Gln Pro Ser Thr Thr Gln Ile Thr Gln
1               5                   10                  15

Thr Gly Gln Thr Thr Thr Thr Thr Val Gly Ser Leu Gly Glu His
            20                  25                  30

Ser Val Thr Thr Thr Gly Ser Gly Ala Ala Gln Thr Ser Gln Thr
        35                  40                  45

Val Thr Leu Ile Ala Asp His Glu Met Gln Glu Ile Ala Ser Gln Asp
    50                  55                  60

Gly Ser Ala Val Ser Phe Ser Ala Glu His Ser Phe Ser Thr Leu Pro
```

-continued

```
            65                  70                  75                  80
Pro Glu Thr Gly Ser Val Gly Ala Thr Ala Gln Ser Ala Gln Ser Ala
                    85                  90                  95
Gly Leu Phe Ser Leu Ser Gly Arg Thr Gln Arg Arg Asp Ser Glu Ile
                100                 105                 110
Ser Ser Ser Ser Asp Gly Ser Ser Ile Ser Arg Thr Ser Ser Asn Ala
                115                 120                 125
Ser Ser Gly Glu Thr Ser Arg Ala Glu Ser Ser Pro Asp Leu Gly Asp
            130                 135                 140
Leu Asp Ser Leu Ser Gly Ser Glu Arg Ala Glu Gly Ala Glu Gly Pro
145                 150                 155                 160
Glu Gly Pro Gly Gly Leu Pro Glu Ser Thr Ile Pro His Tyr Asp Pro
                165                 170                 175
Thr Asp Lys Ala Ser Ile Leu Asn Phe Leu Lys Asn Pro Ala Val Gln
                180                 185                 190
Gln Lys Met Gln Thr Lys Gly Gly His Phe Val Tyr Val Asp Glu Ala
                195                 200                 205
Arg Ser Ser Phe Ile Phe Val Arg Asn Gly Asp Trp Ser Thr Ala Glu
            210                 215                 220
Ser Ile Lys Val Ser Asn Ala Lys Thr Lys Glu Asn Ile Thr Lys Pro
225                 230                 235                 240
Ala Asp Leu Glu Met Cys Ile Ala Lys Phe Cys Val Gly Tyr Glu Thr
                245                 250                 255
Ile His Ser Asp Trp Thr Gly Arg Val Lys Pro Thr Met Glu Glu Arg
                260                 265                 270
Ser Gly Ala Thr Gly Asn Tyr Asn His Leu Met Leu Ser Met Lys Phe
            275                 280                 285
Lys Thr Ala Val Val Tyr Gly Pro Trp Asn Ala Lys Glu Ser Ser Ser
            290                 295                 300
Gly Tyr Thr Pro Ser Ala Trp Arg Arg Gly Ala Lys Val Glu Thr Gly
305                 310                 315                 320
Pro Ile Trp Asp Val Gly Gly Leu Lys Gly Ile Asn Trp Lys Thr
                325                 330                 335
Thr Pro Ala Pro Asp Phe Ser Phe Ile Asn Glu Thr Pro Gly Gly Gly
                340                 345                 350
Ala His Ser Thr Ser His Thr Gly Pro Gly Thr Pro Val Gly Ala Thr
            355                 360                 365
Val Val Pro Asn Val Asn Val Asn Leu Gly Gly Ile Lys Val Asp Leu
            370                 375                 380
Gly Gly Ile Asn Leu Gly Gly Ile Thr Thr Asn Val Thr Thr Glu Glu
385                 390                 395                 400
Gly Gly Gly Thr Asn Ile Thr Ser Thr Lys Ser Thr Ser Thr Asp Asp
                405                 410                 415
Lys Val Ser Ile Thr Ser Thr Gly Ser Gln Ser Thr Ile Glu Glu Asp
                420                 425                 430
Thr Ile Gln Phe Asp Asp Pro Gly Gln Gly Glu Asp Asp Asn Ala Ile
                435                 440                 445
Pro Gly Thr Asn Thr Pro Pro Pro Gly Pro Pro Asn Leu Ser
                450                 455                 460
Ser Ser Arg Leu Leu Thr Ile Ser Asn Ala Ser Leu Asn Gln Val Leu
465                 470                 475                 480
Gln Asn Val Arg Gln His Leu Asn Thr Ala Tyr Asp Ser Asn Gly Asn
                485                 490                 495
```

-continued

```
Ser Val Ser Asp Leu Asn Gln Asp Leu Gly Gln Val Val Lys Asn Ser
            500                 505                 510

Glu Asn Gly Val Asn Phe Pro Thr Val Ile Leu Pro Lys Thr Thr Gly
            515                 520                 525

Asp Thr Asp Pro Ser Gly Gln Ala Thr Gly Val Thr Glu Gly Gly
            530                 535                 540

Gly His Ile Arg Asn Ile Ile Gln Arg Asn Thr Gln Ser Thr Gly Gln
545                 550                 555                 560

Ser Glu Gly Ala Thr Pro Thr Pro Gln Pro Thr Ile Ala Lys Ile Val
                565                 570                 575

Thr Ser Leu Arg Lys Ala Asn Val Ser Ser Ser Val Leu Pro Gln
                580                 585                 590

Pro Gln Val Ala Thr Thr Ile Thr Pro Gln Ala Arg Thr Ala Ser Thr
                595                 600                 605

Ser Thr Thr Ser Ile Gly Thr Gly Thr Glu Ser Thr Ser Thr Thr Ser
            610                 615                 620

Thr Gly Thr Gly Thr Gly Ser Val Ser Thr Gln Ser Thr Gly Val Gly
625                 630                 635                 640

Thr Pro Thr Thr Thr Thr Arg Ser Thr Gly Thr Ser Ala Thr Thr Thr
                645                 650                 655

Thr Ser Ser Ala Ser Thr Gln Thr Pro Gln Ala Pro Leu Pro Ser Gly
                660                 665                 670

Thr Arg His Val Ala Thr Ile Ser Leu Val Arg Asn Ala Ala Gly Arg
                675                 680                 685

Ser Ile Val Leu Gln Gln Gly Gly Arg Ser Gln Ser Phe Pro Ile Pro
            690                 695                 700

Pro Ser Gly Thr Gly Thr Gln Asn Met Gly Ala Gln Leu Trp Ala Ala
705                 710                 715                 720

Ala Ser Gln Val Ala Ser Thr Leu Gly Gln Val Val Asn Gln Ala Ala
                725                 730                 735

Thr Ala Gly Ser Gln Pro Ser Ser Arg Arg Ser Ser Pro Thr Ser Pro
            740                 745                 750

Arg Arg Lys
        755

<210> SEQ ID NO 54
<211> LENGTH: 221
<212> TYPE: PRT
<213> ORGANISM: C. pneumoniae CWL029
<220> FEATURE:
<221> NAME/KEY: misc_feature
<223> OTHER INFORMATION: SET Domain protein
<221> NAME/KEY: misc_feature
<223> OTHER INFORMATION: gi[43]77196

<400> SEQUENCE: 54

Met Ser Thr Val Thr Thr Glu Pro Cys Ser Ser Ile His Ile Ser Leu
1               5                   10                  15

Asn Asn Asp Trp Arg Asp Ser Gln Pro Tyr Ser Leu Asp Arg Ala Ser
            20                  25                  30

Glu Leu Leu His Phe Arg Phe Leu Pro Ser Leu Val Phe Ser Asn Trp
        35                  40                  45

Lys Val Glu Gln Gln Ile Glu Thr Leu Cys His Lys Ser Glu Lys Arg
    50                  55                  60

Arg Leu Ile Ser Pro Leu Ala Lys Trp Leu Gly Lys Leu His Lys Gln
65                  70                  75                  80
```

```
Asp Leu Leu Cys Pro Pro Ala Pro Val Ser Val Cys Trp Ile Asn
                 85                  90                  95

Ala His Val Gly Tyr Gly Val Phe Ala Arg Asp Glu Ile Ala Pro Trp
            100                 105                 110

Thr Tyr Ile Gly Glu Tyr Thr Gly Ile Leu Arg His Arg Gln Ala Ile
            115                 120                 125

Trp Met Asp Glu Asn Asp Tyr Cys Phe Arg Tyr Pro Met Pro Leu Phe
        130                 135                 140

Thr Leu Arg Tyr Phe Thr Ile Asp Ser Gly Lys Gln Gly Asn Val Thr
145                 150                 155                 160

Arg Phe Ile Asn His Ser Glu Gln Pro Asn Ala Glu Ala Ile Gly Val
                165                 170                 175

Phe Ser Glu Gly Leu Phe His Val Ile Arg Thr Val Ala Pro Ile
            180                 185                 190

Tyr Ala Gly Gln Glu Ile Cys Tyr His Tyr Gly Pro Leu Tyr Trp Lys
            195                 200                 205

His Arg Lys Lys Arg Glu Glu Phe Ile Pro Glu Glu Glu
    210                 215                 220

<210> SEQ ID NO 55
<211> LENGTH: 98
<212> TYPE: PRT
<213> ORGANISM: C. pneumoniae CWL029
<220> FEATURE:
<221> NAME/KEY: misc_feature
<223> OTHER INFORMATION: hypothetical protein
<221> NAME/KEY: misc_feature
<223> OTHER INFORMATION: gi[43]76483

<400> SEQUENCE: 55

Met Ser Tyr Pro Asp Ile Ser Asn Val Gln Ala Ser Ser Ile Gln Ser
1               5                   10                  15

Ala Leu Leu His Lys Thr Ser Asp Gln Ile Gln Gln Lys Arg Cys Phe
            20                  25                  30

Lys Gln Ser Thr Phe Val Ile Leu Ala Val Ser Leu Val Ile Ile Gly
        35                  40                  45

Ser Leu Phe Leu Leu Ala Gly Val Ala Ile Leu Thr Val Phe Ser His
    50                  55                  60

Gly Val Leu Ser Leu Val Phe Gly Val Leu Gly Ile Val Leu Gly Leu
65              70                  75                  80

Leu Leu Leu Ala Gly Gly Val Gly Leu Leu Val Glu Glu Ala Lys Ser
                85                  90                  95

Leu Leu

<210> SEQ ID NO 56
<211> LENGTH: 64
<212> TYPE: PRT
<213> ORGANISM: C. pneumoniae CWL029
<220> FEATURE:
<221> NAME/KEY: misc_feature
<223> OTHER INFORMATION: CT382.1 hypothetical protein
<221> NAME/KEY: misc_feature
<223> OTHER INFORMATION: gi[43]76770

<400> SEQUENCE: 56

Met Ile Lys Gln Ala Cys Lys Phe Tyr Leu Leu Gln Cys Leu Leu Cys
1               5                   10                  15

Ala Leu Tyr Trp Leu Leu Lys Tyr Cys Arg Lys Leu Leu Lys Gly Thr
            20                  25                  30
```

```
Leu His His Ser Glu Glu Thr Leu Tyr Gln Ala Leu Leu Ser Ser Leu
            35                  40                  45

Ile Asp Leu Leu Tyr Gln Leu Lys Gln Leu Pro Ala Pro Thr Asn Glu
        50                  55                  60
```

<210> SEQ ID NO 57
<211> LENGTH: 50
<212> TYPE: PRT
<213> ORGANISM: C. pneumoniae CWL029
<220> FEATURE:
<221> NAME/KEY: misc_feature
<223> OTHER INFORMATION: hypothetical protein
<221> NAME/KEY: misc_feature
<223> OTHER INFORMATION: gi[43]76779

<400> SEQUENCE: 57

```
Met Arg Thr Tyr Thr Arg Ser Pro Lys Gln Ser Gly Val Glu Arg Lys
1               5                   10                  15

Gln Glu Asp Ala Glu Thr Ser Phe Ile Glu Thr Pro Lys Gly Ile Leu
            20                  25                  30

Lys Lys Pro Gly Asn Lys Asp Pro Lys Gly Lys His Val His Trp Lys
        35                  40                  45

Asp Ser
    50
```

<210> SEQ ID NO 58
<211> LENGTH: 775
<212> TYPE: PRT
<213> ORGANISM: C. pneumoniae CWL029
<220> FEATURE:
<221> NAME/KEY: misc_feature
<223> OTHER INFORMATION: hypothetical protein
<221> NAME/KEY: misc_feature
<223> OTHER INFORMATION: gi[43]76756

<400> SEQUENCE: 58

```
Met Ala Ser Gly Ile Gly Gly Ser Ser Gly Leu Gly Lys Ile Pro Pro
1               5                   10                  15

Lys Asp Asn Gly Asp Arg Ser Arg Ser Pro Ser Pro Lys Gly Glu Leu
            20                  25                  30

Gly Ser His Glu Ile Ser Leu Pro Pro Gln Glu His Gly Glu Glu Gly
        35                  40                  45

Ala Ser Gly Ser Ser His Ile His Ser Ser Ser Phe Leu Pro Glu
    50                  55                  60

Asp Gln Glu Ser Gln Ser Ser Ser Ala Ala Ser Ser Pro Gly Phe
65                  70                  75                  80

Phe Ser Arg Val Arg Ser Gly Val Asp Arg Ala Leu Lys Ser Phe Gly
            85                  90                  95

Asn Phe Phe Ser Ala Glu Ser Thr Ser Gln Ala Arg Glu Thr Arg Gln
            100                 105                 110

Ala Phe Val Arg Leu Ser Lys Thr Ile Thr Ala Asp Glu Arg Arg Asp
        115                 120                 125

Val Asp Ser Ser Ala Ala Thr Glu Ala Arg Val Ala Glu Asp
        130                 135                 140

Ala Ser Val Ser Gly Glu Asn Pro Ser Gln Gly Val Pro Glu Thr Ser
145                 150                 155                 160

Ser Gly Pro Glu Pro Gln Arg Leu Phe Ser Leu Pro Ser Val Lys Lys
            165                 170                 175

Gln Ser Gly Leu Gly Arg Leu Val Gln Thr Val Arg Asp Arg Ile Val
```

-continued

```
              180                 185                 190
Leu Pro Ser Gly Ala Pro Pro Thr Asp Ser Glu Pro Leu Ser Leu Tyr
        195                 200                 205
Glu Leu Asn Leu Arg Leu Ser Ser Leu Arg Gln Glu Leu Ser Asp Ile
    210                 215                 220
Gln Ser Asn Asp Gln Leu Thr Pro Glu Glu Lys Ala Glu Ala Thr Val
225                 230                 235                 240
Thr Ile Gln Gln Leu Ile Gln Ile Thr Glu Phe Gln Cys Gly Tyr Met
                245                 250                 255
Glu Ala Thr Gln Ser Ser Val Ser Leu Ala Glu Ala Arg Phe Lys Gly
            260                 265                 270
Val Glu Thr Ser Asp Glu Ile Asn Ser Leu Cys Ser Glu Leu Thr Asp
        275                 280                 285
Pro Glu Leu Gln Glu Leu Met Ser Asp Gly Asp Ser Leu Gln Asn Leu
    290                 295                 300
Leu Asp Glu Thr Ala Asp Asp Leu Glu Ala Ala Leu Ser His Thr Arg
305                 310                 315                 320
Leu Ser Phe Ser Leu Asp Asp Asn Pro Thr Pro Ile Asp Asn Asn Pro
                325                 330                 335
Thr Leu Ile Ser Gln Glu Glu Pro Ile Tyr Glu Glu Ile Gly Gly Ala
            340                 345                 350
Ala Asp Pro Gln Arg Thr Arg Glu Asn Trp Ser Thr Arg Leu Trp Asn
        355                 360                 365
Gln Ile Arg Glu Ala Leu Val Ser Leu Leu Gly Met Ile Leu Ser Ile
    370                 375                 380
Leu Gly Ser Ile Leu His Arg Leu Arg Ile Ala Arg His Ala Ala Ala
385                 390                 395                 400
Glu Ala Val Gly Arg Cys Cys Thr Cys Arg Gly Glu Cys Thr Ser
                405                 410                 415
Ser Glu Glu Asp Ser Met Ser Val Gly Ser Pro Ser Glu Ile Asp Glu
            420                 425                 430
Thr Glu Arg Thr Gly Ser Pro His Asp Val Pro Arg Arg Asn Gly Ser
        435                 440                 445
Pro Arg Glu Asp Ser Pro Leu Met Asn Ala Leu Val Gly Trp Ala His
    450                 455                 460
Lys His Gly Ala Lys Thr Lys Glu Ser Ser Glu Ser Ser Thr Pro Glu
465                 470                 475                 480
Ile Ser Ile Ser Ala Pro Ile Val Arg Gly Trp Ser Gln Asp Ser Ser
                485                 490                 495
Val Ser Phe Ile Val Met Glu Asp Asp His Ile Phe Tyr Asp Val Pro
            500                 505                 510
Arg Arg Lys Asp Gly Ile Tyr Asp Val Pro Ser Ser Pro Arg Trp Ser
        515                 520                 525
Pro Ala Arg Glu Leu Glu Glu Asp Val Phe Gly Asp Tyr Glu Val Pro
    530                 535                 540
Ile Thr Ser Ala Glu Pro Ser Lys Asp Lys Asn Ile Tyr Met Thr Pro
545                 550                 555                 560
Arg Leu Ala Thr Pro Ala Ile Tyr Asp Leu Pro Ser Arg Pro Gly Ser
                565                 570                 575
Ser Gly Ser Ser Arg Ser Pro Ser Asp Arg Val Arg Ser Ser Ser
            580                 585                 590
Pro Asn Arg Arg Gly Val Pro Leu Pro Pro Val Pro Ser Pro Ala Met
        595                 600                 605
```

-continued

Ser Glu Glu Gly Ser Ile Tyr Glu Asp Met Ser Gly Ala Ser Gly Ala
    610                 615                 620

Gly Glu Ser Asp Tyr Glu Asp Met Ser Arg Ser Pro Ser Pro Arg Gly
625                 630                 635                 640

Asp Leu Asp Glu Pro Ile Tyr Ala Asn Thr Pro Glu Asp Asn Pro Phe
                645                 650                 655

Thr Gln Arg Asn Ile Asp Arg Ile Leu Gln Glu Arg Ser Gly Gly Ala
            660                 665                 670

Ser Ala Ser Pro Val Glu Pro Ile Tyr Asp Glu Ile Pro Trp Ile His
        675                 680                 685

Gly Arg Pro Pro Ala Thr Leu Pro Arg Pro Glu Asn Thr Leu Thr Asn
    690                 695                 700

Val Ser Leu Arg Val Ser Pro Gly Phe Gly Pro Glu Val Arg Ala Ala
705                 710                 715                 720

Leu Leu Ser Glu Ser Val Ser Ala Val Met Val Glu Ala Glu Ser Ile
                725                 730                 735

Val Pro Pro Thr Glu Pro Gly Asp Gly Glu Ser Glu Tyr Leu Glu Pro
            740                 745                 750

Leu Gly Gly Leu Val Ala Thr Thr Lys Ile Leu Leu Gln Lys Gly Trp
        755                 760                 765

Pro Arg Gly Glu Ser Asn Ala
    770                 775

<210> SEQ ID NO 59
<211> LENGTH: 104
<212> TYPE: PRT
<213> ORGANISM: C. trachomatis
<220> FEATURE:
<221> NAME/KEY: misc_feature
<223> OTHER INFORMATION: hypothetical protein
<221> NAME/KEY: misc_feature
<223> OTHER INFORMATION: gi[33]28515

<400> SEQUENCE: 59

Met Gly Asp Val Met Ile Gln Ser Val Lys Thr Glu Ser Gly Leu Val
1               5                   10                  15

Glu Gly His Arg Gly Ile Cys Asp Ser Leu Gly Arg Val Val Gly Ala
            20                  25                  30

Leu Ala Lys Val Ala Lys Leu Val Ala Leu Ala Ala Leu Val Leu
        35                  40                  45

Asn Gly Ala Leu Cys Val Leu Ser Leu Val Ala Leu Cys Val Gly Ala
    50                  55                  60

Thr Pro Val Gly Pro Leu Ala Val Leu Val Ala Thr Thr Leu Ala Ser
65                  70                  75                  80

Phe Leu Cys Ala Ala Cys Val Leu Phe Ile Ala Ala Lys Asp Arg Gly
                85                  90                  95

Trp Ile Ala Ser Thr Asn Lys Cys
            100

<210> SEQ ID NO 60
<211> LENGTH: 439
<212> TYPE: PRT
<213> ORGANISM: C. trachomatis
<220> FEATURE:
<221> NAME/KEY: misc_feature
<223> OTHER INFORMATION: hypothetical protein
<221> NAME/KEY: misc_feature
<223> OTHER INFORMATION: gi[33]29021

<400> SEQUENCE: 60

```
Met Thr Thr Gly Val Arg Gly Asp Asn Ala Pro Asp Pro Ser Leu Leu
  1               5                  10                  15
Ala Gln Leu Thr Gln Asn Ala Asn Ser Ala Ser Ala Ala Ser Thr Gly
             20                  25                  30
Lys Asn Gly Gln Val Ala Gly Lys Gln Glu Asn Val Asp Ala Ser
         35                  40                  45
Phe Glu Asp Leu Leu Gln Asp Ala Gln Gly Thr Gly Gly Ser Lys Lys
 50                  55                  60
Ala Thr Ala Asn Gln Thr Ser Lys Ser Gly Lys Ser Glu Lys Ala Gln
 65                  70                  75                  80
Ala Ser Ser Gly Thr Ser Thr Thr Ser Val Ala Gln Ala Ser Gln
             85                  90                  95
Thr Ala Thr Ala Gln Ala Val His Gly Ala Arg Asp Ser Gly Phe Asn
                100                 105                 110
Ser Asp Gly Ser Ala Thr Leu Pro Ser Pro Thr Gly Thr Glu Val Asn
             115                 120                 125
Gly Val Val Leu Arg Lys Gly Met Gly Thr Leu Ala Leu Met Gly Leu
         130                 135                 140
Ile Met Thr Leu Leu Ala Gln Ala Ser Ala Lys Ser Trp Ser Ser Ser
145                 150                 155                 160
Phe Gln Gln Gln Asn Gln Ala Ile Gln Asn Gln Val Ala Met Ala Pro
                165                 170                 175
Glu Ile Gly Asn Ala Ile Arg Thr Gln Ala Asn His Gln Ala Gln Ala
             180                 185                 190
Thr Glu Leu Gln Ala Gln Gln Ser Leu Ile Ser Gly Ile Thr Asn Ile
         195                 200                 205
Val Gly Phe Ala Val Ser Val Gly Gly Gly Ile Leu Ser Ala Ser Lys
     210                 215                 220
Ser Leu Gly Gly Leu Lys Ser Ala Ala Phe Thr Asn Glu Thr Ala Ser
225                 230                 235                 240
Ala Thr Thr Ser Ala Thr Ser Ser Leu Ala Lys Thr Ala Thr Ser Ala
                245                 250                 255
Leu Asp Asp Val Ala Gly Thr Ala Thr Ala Val Gly Ala Lys Ala Thr
             260                 265                 270
Ser Gly Ala Ala Ser Ala Ala Ser Ser Ala Ala Thr Lys Leu Thr Gln
         275                 280                 285
Asn Met Ala Glu Ser Ala Ser Lys Thr Leu Ser Gln Thr Ala Ser Lys
     290                 295                 300
Ser Ala Gly Gly Leu Phe Gly Gln Ala Leu Asn Thr Pro Ser Trp Ser
305                 310                 315                 320
Glu Lys Val Ser Arg Gly Met Asn Val Val Lys Thr Gln Gly Thr Arg
                325                 330                 335
Ala Ala Lys Phe Ala Gly Arg Ala Leu Ser Ser Ala Met Asn Ile Ser
             340                 345                 350
Gln Met Val His Gly Leu Thr Ala Gly Ile Asp Gly Ile Val Gly Gly
         355                 360                 365
Val Ile Gly Ala Gln Val Ala Gln Glu Gln Arg Met Ala Gly Met Ala
     370                 375                 380
Glu Ala Arg Ala Glu Glu Leu Lys Ser Leu Asn Ser Val Gln Ala Gln
385                 390                 395                 400
Tyr Ala Ser Gln Ala Gln Leu Gln Glu Gln Ser Gln Gln Ser Phe
                405                 410                 415
```

```
Asn Ser Ala Leu Gln Thr Leu Gln Ser Ile Ser Asp Ser Ala Leu Gln
            420                 425                 430

Thr Thr Ala Ser Met Phe Asn
        435
```

```
<210> SEQ ID NO 61
<211> LENGTH: 168
<212> TYPE: PRT
<213> ORGANISM: C. trachomatis
<220> FEATURE:
<221> NAME/KEY: misc_feature
<223> OTHER INFORMATION: hypothetical protein
<221> NAME/KEY: misc_feature
<223> OTHER INFORMATION: gi[33]29121

<400> SEQUENCE: 61
```

```
Met Val Arg Tyr Pro Leu Glu Pro Val Leu Ser Ile Lys Lys Asp Arg
1               5                   10                  15

Val Asp Arg Ala Glu Lys Val Val Lys Glu Lys Arg Arg Leu Leu Glu
            20                  25                  30

Leu Glu Gln Glu Lys Leu Arg Glu Arg Glu Ser Glu Arg Asp Lys Val
        35                  40                  45

Lys Asn His Tyr Met Gln Lys Ile Arg Gln Leu Arg Glu Gln Leu Asp
    50                  55                  60

Asp Gly Thr Thr Ser Asp Ala Ile Leu Lys Met Lys Ala Tyr Ile Lys
65                  70                  75                  80

Val Val Ala Ile Gln Leu Ser Glu Glu Glu Lys Val Asn Lys Gln
                85                  90                  95

Lys Glu Asn Val Leu Ala Ala Ser Lys Glu Leu Glu Arg Ala Glu Val
            100                 105                 110

Glu Leu Thr Lys Arg Arg Lys Glu Glu Lys Thr Arg Leu His Lys
        115                 120                 125

Glu Glu Trp Met Lys Glu Ala Leu Lys Glu Glu Ala Arg Gln Glu Glu
    130                 135                 140

Lys Glu Gln Asp Glu Met Gly Gln Leu Leu His Gln Leu His Lys Gln
145                 150                 155                 160

Lys Gln Arg Glu Ser Gly Glu Asn
                165
```

```
<210> SEQ ID NO 62
<211> LENGTH: 819
<212> TYPE: PRT
<213> ORGANISM: H. influenzae
<220> FEATURE:
<221> NAME/KEY: misc_feature
<223> OTHER INFORMATION: conserved hypothetical protein
<221> NAME/KEY: misc_feature
<223> OTHER INFORMATION: gi[15]74537

<400> SEQUENCE: 62
```

```
Met Ala Asp Val Leu Ser Arg Phe Asn Ser Gly Lys Leu Trp Asp Phe
1               5                   10                  15

Lys Gly Gly Ile His Pro Pro Glu Met Lys Ser Gln Ser Asn Ser Gln
            20                  25                  30

Pro Leu Arg His Leu Pro Leu Gly Thr Asp Phe Tyr Ile Pro Leu Lys
        35                  40                  45

Gln His Leu Gly Thr Thr Gly Asn Leu Leu Ile Lys Glu Gly Asp Tyr
    50                  55                  60

Val Leu Lys Gly Gln Ala Leu Thr Lys Gly Asp Gly Leu Arg Met Leu
```

```
                65                  70                  75                  80
Pro Val His Ala Pro Thr Ser Gly Thr Ile Lys Ser Ile Lys Pro Tyr
                    85                  90                  95
Val Ala Thr His Pro Ser Gly Leu Asp Glu Pro Thr Ile His Leu Gln
                    100                 105                 110
Ala Asp Gly Leu Asp Gln Trp Ile Glu Arg Asn Pro Ile Asp Asp Phe
                    115                 120                 125
Ser Thr Leu Ser Ser Glu Gln Leu Ile His Lys Ile Tyr Gln Ala Gly
                    130                 135                 140
Ile Ala Gly Leu Gly Gly Ala Val Phe Pro Thr Ala Ala Lys Ile Gln
145                 150                 155                 160
Ser Ala Glu Gln Lys Val Lys Leu Leu Ile Ile Asn Gly Ala Glu Cys
                    165                 170                 175
Glu Pro Tyr Ile Thr Cys Asp Asp Arg Leu Met Arg Glu Arg Ala Asp
                    180                 185                 190
Glu Ile Ile Lys Gly Ile Arg Ile Leu Arg Tyr Ile Leu His Pro Glu
                    195                 200                 205
Lys Val Val Ile Ala Ile Glu Asp Asn Lys Pro Glu Ala Ile Ser Ala
210                 215                 220
Ile Arg Asn Ala Leu Gln Gly Ala Asn Asp Ile Ser Ile Arg Val Ile
225                 230                 235                 240
Pro Thr Lys Tyr Pro Ser Gly Ala Thr Lys Gln Leu Ile Tyr Leu Leu
                    245                 250                 255
Thr Gly Ile Glu Val Pro Ser Gly Glu Arg Ser Ser Ile Gly Val
                    260                 265                 270
Leu Met Gln Asn Val Gly Thr Met Phe Ala Ile Lys Arg Ala Ile Ile
                    275                 280                 285
Asn Asp Glu Pro Leu Ile Glu Arg Val Val Thr Leu Thr Gly Asn Lys
                    290                 295                 300
Ile Ala Glu Lys Gly Asn Tyr Trp Val Arg Leu Gly Thr Pro Ile Ser
305                 310                 315                 320
Gln Ile Leu Ser Asp Ala Gly Tyr Gln Phe Asp Lys His Phe Pro Ile
                    325                 330                 335
Phe Ala Gly Gly Pro Met Met Gly Leu Glu Leu Pro Asn Leu Asn Ala
                    340                 345                 350
Pro Val Thr Lys Leu Val Asn Cys Leu Leu Ala Pro Asp Tyr Leu Glu
                    355                 360                 365
Tyr Ala Glu Pro Glu Ala Glu Gln Ala Cys Ile Arg Cys Ser Ser Cys
                    370                 375                 380
Ser Asp Ala Cys Pro Val Asn Leu Met Pro Gln Gln Leu Tyr Trp Phe
385                 390                 395                 400
Ala Arg Ser Glu Asp His Lys Lys Ser Glu Glu Tyr Ala Leu Lys Asp
                    405                 410                 415
Cys Ile Glu Cys Gly Ile Cys Ala Tyr Val Cys Pro Ser His Ile Pro
                    420                 425                 430
Leu Ile Gln Tyr Phe Arg Gln Glu Lys Ala Lys Ile Trp Gln Ile Lys
                    435                 440                 445
Glu Lys Gln Lys Lys Ser Asp Glu Ala Lys Ile Arg Phe Glu Ala Lys
                    450                 455                 460
Gln Ala Arg Met Glu Arg Glu Glu Arg Lys Ala Arg Ser Gln
465                 470                 475                 480
Arg Ala Ala Gln Ala Arg Arg Glu Glu Leu Ala Gln Thr Lys Gly Glu
                    485                 490                 495
```

```
Asp Pro Val Lys Ala Ala Leu Glu Arg Leu Lys Ala Lys Lys Ala Asn
            500                 505                 510

Glu Thr Glu Ser Thr Gln Ile Lys Thr Leu Thr Ser Glu Lys Gly Glu
        515                 520                 525

Val Leu Pro Asp Asn Thr Asp Leu Met Ala Gln Arg Lys Ala Arg Arg
    530                 535                 540

Leu Ala Arg Gln Gln Ala Ala Ser Gln Val Glu Asn Gln Glu Gln Gln
545                 550                 555                 560

Thr Gln Pro Thr Asn Ala Lys Lys Ala Val Ala Ala Leu Ala
                565                 570                 575

Arg Ala Lys Ala Lys Lys Leu Ala Gln Ala Asn Ser Thr Ser Glu Ala
            580                 585                 590

Ile Ser Asn Ser Gln Thr Ala Glu Asn Gln Val Glu Lys Thr Lys Ser
            595                 600                 605

Ala Val Glu Lys Thr Gln Glu Asn Ser Thr Ala Leu Asp Pro Lys Lys
            610                 615                 620

Ala Ala Val Ala Ala Ala Ile Ala Arg Ala Lys Ala Lys Lys Leu Ala
625                 630                 635                 640

Gln Thr Asn Ser Thr Ser Glu Ala Ile Ser Asn Ser Gln Thr Ala Glu
                645                 650                 655

Asn Glu Val Glu Lys Thr Lys Ser Ala Val Glu Lys Thr Gln Glu Asn
            660                 665                 670

Ser Thr Ala Leu Asp Ala Lys Lys Ala Ile Ala Ala Ala Ile Ala
                675                 680                 685

Arg Ala Lys Ala Lys Lys Leu Ala Gln Ala Asn Ser Ala Ser Glu Ala
            690                 695                 700

Ile Ser Asn Ser Gln Thr Ala Glu Asn Glu Val Glu Lys Thr Lys Ser
705                 710                 715                 720

Ala Val Glu Lys Thr Gln Gln Asn Ser Thr Ala Leu Asp Pro Lys Lys
                725                 730                 735

Ala Ala Val Ala Ala Ala Ile Ala Arg Ala Lys Ala Lys Lys Leu Ala
                740                 745                 750

Gln Ala Asn Ser Thr Ser Glu Ala Ile Ser Asn Ser Gln Thr Ala Glu
            755                 760                 765

Asn Glu Val Glu Lys Thr Lys Ser Ala Val Glu Lys Thr Gln Glu Asn
            770                 775                 780

Ser Thr Ala Leu Asp Pro Lys Lys Ala Ala Val Ala Ala Ala Ile Ala
785                 790                 795                 800

Arg Ala Lys Ala Lys Lys Leu Ala Lys Thr Gln Ala Thr Leu Glu Asn
                805                 810                 815

Asn Gln Glu

<210> SEQ ID NO 63
<211> LENGTH: 52
<212> TYPE: PRT
<213> ORGANISM: H. influenzae
<220> FEATURE:
<221> NAME/KEY: misc_feature
<223> OTHER INFORMATION: predicted coding region HI1562
<221> NAME/KEY: misc_feature
<223> OTHER INFORMATION: gi[15]74414

<400> SEQUENCE: 63

Met Leu Ser Lys Asp Pro Lys Val Leu Ile Lys Leu Gly Glu Leu Glu
1               5                   10                  15
```

```
Lys Asp Lys Ser Lys Ala Lys Lys Tyr Phe Gly Asp Ala Cys Asp Leu
            20                  25                  30

Arg Ser Gln Glu Gly Cys Asp Lys Tyr Arg Glu Leu Asn Gln Lys Gln
        35                  40                  45

Asp Thr Asn Lys
    50

<210> SEQ ID NO 64
<211> LENGTH: 150
<212> TYPE: PRT
<213> ORGANISM: H. influenzae
<220> FEATURE:
<221> NAME/KEY: misc_feature
<223> OTHER INFORMATION: conserved hypothetical protein
<221> NAME/KEY: misc_feature
<223> OTHER INFORMATION: gi[15]74625

<400> SEQUENCE: 64

Met Thr Leu Gln Leu Asn Thr Ile Ala Leu Leu Val Ile Leu Leu
1               5                   10                  15

Ile Leu Gly Val Leu Ser Asn Asn Ser Thr Ile Thr Ile Ser Ala Ala
            20                  25                  30

Val Leu Leu Ile Met Gln Gln Thr Phe Leu Ser Ser His Ile Pro Leu
        35                  40                  45

Leu Glu Lys Tyr Gly Val Lys Ile Gly Ile Ile Leu Thr Ile Gly
    50                  55                  60

Val Leu Ser Pro Leu Val Ser Gly Lys Ile Gln Leu Pro Asp Leu Ser
65                  70                  75                  80

Gly Phe Leu Ser Trp Lys Met Ala Leu Ser Ile Ser Val Gly Val Leu
                85                  90                  95

Val Ala Trp Leu Ala Gly Lys Gly Val Pro Leu Met Gly Glu Gln Pro
            100                 105                 110

Ile Leu Val Thr Gly Leu Leu Ile Gly Thr Ile Ile Gly Val Ala Phe
        115                 120                 125

Leu Gly Gly Ile Pro Val Gly Pro Leu Ile Ala Ala Gly Ile Leu Ala
    130                 135                 140

Leu Leu Leu Gly Lys Ile
145                 150

<210> SEQ ID NO 65
<211> LENGTH: 129
<212> TYPE: PRT
<213> ORGANISM: H. influenzae
<220> FEATURE:
<221> NAME/KEY: misc_feature
<223> OTHER INFORMATION: predicted coding region HI1339
<221> NAME/KEY: misc_feature
<223> OTHER INFORMATION: gi[15]74799

<400> SEQUENCE: 65

Met Glu Lys Ile Met Lys Lys Leu Thr Leu Ala Leu Val Leu Gly Ser
1               5                   10                  15

Ala Leu Val Val Thr Gly Cys Phe Asp Lys Gln Glu Ala Lys Gln Lys
            20                  25                  30

Val Glu Asp Thr Lys Gln Thr Val Ala Ser Val Ala Ser Glu Thr Lys
        35                  40                  45

Asp Ala Ala Ala Asn Thr Met Thr Glu Val Lys Glu Lys Ala Gln Gln
    50                  55                  60

Leu Ser Thr Asp Val Lys Asn Lys Val Ala Glu Lys Val Glu Asp Ala
65                  70                  75                  80
```

```
Lys Glu Val Ile Lys Ser Ala Thr Glu Ala Ala Ser Glu Lys Val Gly
                85                  90                  95

Glu Met Lys Glu Ala Ala Ser Glu Lys Ala Ser Glu Met Lys Glu Ala
            100                 105                 110

Val Ser Glu Lys Ala Thr Gln Ala Val Asp Ala Val Lys Glu Ala Thr
        115                 120                 125

Lys

<210> SEQ ID NO 66
<211> LENGTH: 136
<212> TYPE: PRT
<213> ORGANISM: H. influenzae
<220> FEATURE:
<221> NAME/KEY: misc_feature
<223> OTHER INFORMATION: predicted coding region HI1462.1
<221> NAME/KEY: misc_feature
<223> OTHER INFORMATION: "Xaa" may be any amino acid
<221> NAME/KEY: misc_feature
<223> OTHER INFORMATION: gi[32]12225

<400> SEQUENCE: 66

Met Xaa Gln Ser Asn Tyr Ser Met Glu Lys Ile Met Lys Lys Leu Thr
1               5                   10                  15

Leu Ala Leu Val Leu Gly Ser Ala Leu Val Val Thr Gly Cys Phe Asp
            20                  25                  30

Lys Gln Glu Ala Lys Gln Lys Val Glu Asp Thr Lys Gln Thr Val Ala
        35                  40                  45

Ser Val Ala Ser Glu Thr Lys Asp Ala Ala Ala Asn Thr Met Thr Glu
    50                  55                  60

Val Lys Glu Lys Ala Gln Gln Leu Ser Thr Asp Val Lys Asn Lys Val
65                  70                  75                  80

Ala Glu Lys Val Glu Asp Ala Lys Glu Val Ile Lys Ser Ala Thr Glu
                85                  90                  95

Ala Ala Ser Glu Lys Val Gly Glu Met Lys Glu Ala Ala Ser Glu Lys
            100                 105                 110

Ala Ser Glu Met Lys Glu Ala Val Ser Glu Lys Ala Thr Gln Ala Val
        115                 120                 125

Asp Ala Val Lys Glu Ala Thr Lys
    130                 135

<210> SEQ ID NO 67
<211> LENGTH: 113
<212> TYPE: PRT
<213> ORGANISM: H. influenzae
<220> FEATURE:
<221> NAME/KEY: misc_feature
<223> OTHER INFORMATION: conserved hypothetical protein
<221> NAME/KEY: misc_feature
<223> OTHER INFORMATION: gi[15]74607

<400> SEQUENCE: 67

Met Phe Thr Asp Trp Lys Glu His Thr Ser His Val Lys Lys Ser Phe
1               5                   10                  15

Gly Glu Leu Gly Lys Gln Tyr Pro Lys Met Leu Gln Ala Tyr Gln Ala
            20                  25                  30

Leu Gly Ala Ala Ala Ala Glu Gly Asn Val Leu Asp Ala Lys Thr Arg
        35                  40                  45

Glu Leu Ile Ala Leu Ala Val Ala Val Thr Thr Arg Cys Glu Ser Cys
    50                  55                  60
```

-continued

Ile Ser Ala His Ala Glu Glu Ala Val Lys Ala Gly Ala Ser Glu Ala
 65                  70                  75                  80

Glu Val Ala Ala Ala Leu Ala Thr Ala Ile Ala Leu Asn Ala Gly Ala
             85                  90                  95

Ala Tyr Thr Tyr Ser Leu Arg Ala Leu Glu Ala Tyr Ser Val Gln Lys
        100                 105                 110

Ala

<210> SEQ ID NO 68
<211> LENGTH: 33
<212> TYPE: PRT
<213> ORGANISM: H. pylori
<220> FEATURE:
<221> NAME/KEY: misc_feature
<223> OTHER INFORMATION: predicted coding region HP0131
<221> NAME/KEY: misc_feature
<223> OTHER INFORMATION: gi[23]13229

<400> SEQUENCE: 68

Met Pro Tyr Pro Phe Met Ser Phe Lys Gln Thr Phe Tyr Tyr Lys Met
1               5                   10                  15

Glu Ser Lys Thr Met Lys Glu Arg Phe Lys Thr Leu Phe Phe Lys Ile
            20                  25                  30

Phe

<210> SEQ ID NO 69
<211> LENGTH: 12
<212> TYPE: PRT
<213> ORGANISM: H. pylori
<220> FEATURE:
<221> NAME/KEY: misc_feature
<223> OTHER INFORMATION: predicted coding region HP0429
<221> NAME/KEY: misc_feature
<223> OTHER INFORMATION: gi[23]13552

<400> SEQUENCE: 69

Met Asn Glu Asn Gly Lys Lys Glu Ala Leu Gln Leu
1               5                   10

<210> SEQ ID NO 70
<211> LENGTH: 26
<212> TYPE: PRT
<213> ORGANISM: H. pylori
<220> FEATURE:
<221> NAME/KEY: misc_feature
<223> OTHER INFORMATION: predicted coding region HP0560
<221> NAME/KEY: misc_feature
<223> OTHER INFORMATION: gi[23]13684

<400> SEQUENCE: 70

Met Gly Ile Ile Tyr Leu Ile Leu Phe Leu Ile Val Ile Tyr Leu Leu
1               5                   10                  15

Tyr Arg Ile Leu Asp Val Leu Glu Gln Lys
            20                  25

<210> SEQ ID NO 71
<211> LENGTH: 48
<212> TYPE: PRT
<213> ORGANISM: H. pylori
<220> FEATURE:
<221> NAME/KEY: misc_feature
<223> OTHER INFORMATION: predicted coding region HP0756
<221> NAME/KEY: misc_feature
<223> OTHER INFORMATION: gi[23]13894

<400> SEQUENCE: 71

Met Lys Asp Tyr Glu Asp Glu Leu Glu Asp Phe Glu Glu Glu Leu
1               5                   10                  15

Glu Gly Phe Glu Glu Glu Asp Glu Tyr Gly Asp Tyr Lys Asn Val
            20                  25                  30

Tyr Asp Asp Asp Tyr Glu Asp Tyr Asn Ser Asp Tyr Glu Glu Glu
            35                  40                  45

<210> SEQ ID NO 72
<211> LENGTH: 23
<212> TYPE: PRT
<213> ORGANISM: H. pylori
<220> FEATURE:
<221> NAME/KEY: misc_feature
<223> OTHER INFORMATION: predicted coding region HP1500
<221> NAME/KEY: misc_feature
<223> OTHER INFORMATION: gi[23]14686

<400> SEQUENCE: 72

Met Cys Ser Asn Ser Ser Ser Leu Lys Ile Tyr Ser Leu Glu Ser Asn
1               5                   10                  15

Phe Ser Phe Asn Ser Leu Phe
            20

<210> SEQ ID NO 73
<211> LENGTH: 1805
<212> TYPE: PRT
<213> ORGANISM: M. genitalium
<220> FEATURE:
<221> NAME/KEY: misc_feature
<223> OTHER INFORMATION: gi[10]45905

<400> SEQUENCE: 73

Met Lys Pro Phe Asp Lys Lys Pro Ser Leu Gln Pro Ile Tyr Asp Ile
1               5                   10                  15

Gly Phe Asp Asp Gly Tyr Leu Gln Ser Glu Tyr Glu Lys Asn Arg Ser
            20                  25                  30

Lys Thr Asp Val Asp Lys Ile Glu Asn Gln Leu Leu Lys Glu Ile Lys
        35                  40                  45

Ser Leu Glu Asp Glu Leu Lys Asn Leu Lys Gly Leu Lys Asn Gln Ala
    50                  55                  60

Glu Asp Asn Pro Glu Leu Asp Lys Lys Ile Asn His Leu Glu Val Asp
65                  70                  75                  80

Leu Asn Arg Leu Val Asn Glu Tyr Lys Asn Phe Gln Phe Gln Lys Asn
                85                  90                  95

His Met Val Asp Lys Val Ser Glu Leu Asp Asn Leu Thr Arg Phe Tyr
            100                 105                 110

Lys Asn Glu Leu Thr Arg Leu Gln Gln Glu Asn Ala Asp Phe Leu Asn
        115                 120                 125

Ser Lys Tyr Ala Asn Leu Ala Asn Phe Gln Ala Asn Tyr His Asn Lys
    130                 135                 140

Leu Asn Asp Phe His Arg Leu Ile Glu Asn Gln Asn Thr Ile Asn
145                 150                 155                 160

Arg Leu Asn Gln Lys Ile Asn Gly Asn Gln Asn Leu Ile Asp Asn Asn
                165                 170                 175

Val Ala Leu Leu Gln Asn Pro Asn Ile Thr Val Glu Lys Lys Asn Tyr
            180                 185                 190

Leu Leu Asn Val Ile Asp Gln Leu Tyr Asn Glu Leu Asp Gln Leu Glu
        195                 200                 205

-continued

Asn Gln Lys Arg Leu Leu Ser Ile Glu Tyr Glu Asn Thr Tyr Arg Glu
    210                 215                 220

Leu Val Ser Ala Asp Asn Glu Leu Gln Asn Val Tyr Glu Asn Ile Asp
225                 230                 235                 240

Gln Asn Gln Ile Gln Phe Lys His Gln Tyr Gln Thr Tyr Arg Asp Glu
                    245                 250                 255

Leu Ser Gln Leu Glu Arg Lys Ile Gln Leu Thr Lys Gln Glu Leu Val
            260                 265                 270

Asp Lys Glu Ser Ala Leu Arg Val Lys Ile Asp Asp Ala Asp Phe Tyr
        275                 280                 285

Ile Asn Ala Arg Leu Ala Glu Leu Asp Asp Val Ala Lys Gln Leu Ser
    290                 295                 300

Phe Gln Asp Gly Ile Thr Lys Gln Asn Ala Gln His Val Glu Asp Lys
305                 310                 315                 320

Leu Val Ala Leu Asn Lys Glu Lys Asp Arg Leu Asn Thr Gln Lys Glu
                    325                 330                 335

Ala Phe Phe Asn Leu Arg Gln Ser Ala Leu Ile Asp Ile Asn Lys Leu
            340                 345                 350

Gln Gln Glu Asn Glu Leu Phe Ala Lys His Leu Glu His Gln Gln Asn
        355                 360                 365

Glu Phe Glu Gln Lys Gln Ser Asp Ser Leu Leu Lys Leu Glu Thr Glu
    370                 375                 380

Tyr Lys Ala Leu Gln His Lys Ile Asn Glu Phe Lys Asn Glu Ser Ala
385                 390                 395                 400

Thr Lys Ser Glu Glu Leu Leu Asn Gln Glu Arg Glu Leu Phe Glu Lys
                    405                 410                 415

Arg Arg Glu Ile Asp Thr Leu Leu Thr Gln Ala Ser Leu Glu Tyr Glu
            420                 425                 430

His Gln Arg Glu Ser Ser Gln Leu Leu Lys Asp Lys Gln Asn Glu Val
        435                 440                 445

Lys Gln His Phe Gln Asn Leu Glu Tyr Ala Lys Lys Glu Leu Asp Lys
    450                 455                 460

Glu Arg Asn Leu Leu Asp Gln Gln Lys Lys Val Asp Ser Glu Ala Ile
465                 470                 475                 480

Phe Gln Leu Lys Glu Lys Val Ala Gln Glu Arg Lys Glu Leu Glu Glu
                    485                 490                 495

Leu Tyr Leu Val Lys Lys Gln Lys Gln Asp Gln Lys Glu Asn Glu Leu
            500                 505                 510

Leu Phe Phe Glu Lys Gln Leu Lys Gln His Gln Ala Asp Phe Glu Asn
        515                 520                 525

Glu Leu Glu Ala Lys Gln Gln Glu Leu Phe Glu Ala Lys His Ala Leu
    530                 535                 540

Glu Arg Ser Phe Ile Lys Leu Glu Asp Lys Glu Lys Asp Leu Asn Thr
545                 550                 555                 560

Lys Ala Gln Gln Ile Ala Asn Glu Phe Ser Gln Leu Lys Thr Asp Lys
                    565                 570                 575

Ser Lys Ser Ala Asp Phe Glu Leu Met Leu Gln Asn Glu Tyr Glu Asn
            580                 585                 590

Leu Gln Gln Glu Lys Gln Lys Leu Phe Gln Glu Arg Thr Tyr Phe Glu
        595                 600                 605

Arg Asn Ala Ala Val Leu Ser Asn Arg Leu Gln Gln Lys Arg Glu Glu
    610                 615                 620

Leu Leu Gln Gln Lys Glu Thr Leu Asp Gln Leu Thr Lys Ser Phe Glu

```
                625               630               635               640
Gln Glu Arg Leu Ile Asn Gln Arg Glu His Lys Glu Leu Val Ala Ser
                    645               650               655
Val Glu Lys Gln Lys Glu Ile Leu Gly Lys Lys Leu Gln Asp Phe Ser
                    660               665               670
Gln Thr Ser Leu Asn Ala Ser Lys Asn Leu Ala Glu Arg Glu Met Ala
                    675               680               685
Ile Lys Phe Lys Glu Lys Glu Ile Glu Ala Thr Glu Lys Gln Leu Leu
                    690               695               700
Asn Asp Val Asn Ala Glu Val Ile Gln Ala Asp Leu Ala Gln Leu
705                 710               715               720
Asn Gln Ser Leu Asn Gln Glu Arg Ser Glu Leu Gln Asn Ala Lys Gln
                    725               730               735
Arg Ile Ala Asp Phe His Asn Asp Ser Leu Lys Lys Leu Asn Glu Tyr
                    740               745               750
Glu Leu Ser Leu Gln Lys Arg Leu Gln Glu Leu Gln Thr Leu Glu Ala
                    755               760               765
Asn Gln Lys Gln His Ser Tyr Gln Asn Gln Ala Tyr Phe Glu Gly Glu
                    770               775               780
Leu Asp Lys Leu Asn Arg Glu Lys Gln Ala Phe Leu Asn Leu Arg Lys
785                 790               795               800
Lys Gln Thr Met Glu Val Asp Ala Ile Lys Gln Arg Leu Ser Asp Lys
                    805               810               815
His Gln Ala Leu Asn Met Gln Gln Ala Glu Leu Asp Arg Lys Thr His
                    820               825               830
Glu Leu Asn Asn Ala Phe Leu Asn His Asp Ala Asp Gln Lys Ser Leu
                    835               840               845
Gln Asp Gln Leu Ala Thr Val Lys Glu Thr Gln Lys Leu Ile Asp Leu
                    850               855               860
Glu Arg Ser Ala Leu Leu Lys Gln Arg Glu Phe Ala Glu Asn Val
865                 870               875               880
Ala Gly Phe Lys Arg His Trp Ser Asn Lys Thr Ser Gln Leu Gln Lys
                    885               890               895
Ile Tyr Glu Leu Thr Lys Lys Gln Glu Ser Glu Gln Thr Gln Lys Glu
                    900               905               910
Thr Glu Leu Lys Ile Ala Phe Ser Asp Leu Gln Lys Asp Tyr Gln Val
                    915               920               925
Phe Glu Leu Gln Lys Asp Gln Glu Phe Arg Gln Ile Glu Ala Lys Gln
                    930               935               940
Arg Glu Leu Asp Lys Leu Ala Glu Lys Asn Asn Gln Val Lys Leu Glu
945                 950               955               960
Leu Asp Asn Arg Phe Gln Ala Leu Gln Asn Gln Lys Gln Asp Thr Val
                    965               970               975
Gln Ala Gln Leu Glu Leu Glu Arg Glu Gln His Gln Leu Asn Leu Glu
                    980               985               990
Gln Thr Ala Phe Asn Gln Ala Asn  Glu Ser Leu Leu Lys  Gln Arg Glu
                    995               1000              1005
Gln Leu  Thr Lys Lys Ile Gln  Ala Phe His Tyr Glu  Leu Lys Lys
         1010              1015              1020
Arg Asn  Gln Phe Leu Ala Leu  Lys Gly Lys Arg Leu  Phe Ala Lys
         1025              1030              1035
Glu Gln  Asp Gln Gln Arg Lys  Asp Gln Glu Ile Asn  Trp Arg Phe
         1040              1045              1050
```

-continued

```
Lys Gln Phe Glu Lys Glu Tyr Thr Asp Phe Asp Glu Ala Lys Lys
1055                1060                1065

Arg Glu Leu Glu Gln Leu Glu Lys Ile Arg Arg Ser Leu Ser Gln
1070                1075                1080

Ser Asn Val Glu Leu Glu Arg Lys Arg Glu Lys Leu Ala Thr Asp
1085                1090                1095

Phe Thr Asn Leu Asn Lys Val Gln His Asn Thr Gln Ile Asn Arg
1100                1105                1110

Asp Gln Leu Asn Ser Gln Ile Arg Gln Phe Leu Leu Glu Arg Lys
1115                1120                1125

Asn Phe Gln Arg Phe Ser Asn Glu Ala Asn Ala Lys Lys Ala Phe
1130                1135                1140

Leu Ile Lys Arg Leu Arg Ser Phe Ala Ser Asn Leu Lys Leu Gln
1145                1150                1155

Lys Glu Ala Leu Ala Ile Gln Lys Leu Glu Phe Asp Lys Arg Asp
1160                1165                1170

Glu Gln Gln Lys Lys Glu Leu Gln Gln Ala Thr Leu Gln Leu Glu
1175                1180                1185

Gln Phe Lys Phe Glu Lys Gln Asn Phe Asp Ile Glu Lys Gln Arg
1190                1195                1200

Gln Leu Val Ala Ile Lys Thr Gln Cys Glu Lys Leu Ser Asp Glu
1205                1210                1215

Lys Lys Ala Leu Asn Gln Lys Leu Val Glu Leu Lys Asn Leu Ser
1220                1225                1230

Gln Thr Tyr Leu Ala Asn Lys Asn Lys Ala Glu Tyr Ser Gln Gln
1235                1240                1245

Gln Leu Gln Gln Lys Tyr Thr Asn Leu Leu Asp Leu Lys Glu Asn
1250                1255                1260

Leu Glu Arg Thr Lys Asp Gln Leu Asp Lys Lys His Arg Ser Ile
1265                1270                1275

Phe Ala Arg Leu Thr Lys Phe Ala Asn Asp Leu Arg Phe Glu Lys
1280                1285                1290

Lys Gln Leu Leu Lys Ala Gln Arg Ile Val Asp Asp Lys Asn Arg
1295                1300                1305

Leu Leu Lys Glu Asn Glu Arg Asn Leu His Phe Leu Ser Asn Glu
1310                1315                1320

Thr Glu Arg Lys Arg Ala Val Leu Glu Asp Gln Ile Ser Tyr Phe
1325                1330                1335

Glu Lys Gln Arg Lys Gln Ala Thr Asp Ala Ile Leu Ala Ser His
1340                1345                1350

Lys Glu Val Lys Lys Lys Glu Gly Glu Leu Gln Lys Leu Leu Val
1355                1360                1365

Glu Leu Glu Thr Arg Lys Thr Lys Leu Asn Asn Asp Phe Ala Lys
1370                1375                1380

Phe Ser Arg Gln Arg Glu Glu Phe Glu Asn Gln Arg Leu Lys Leu
1385                1390                1395

Leu Glu Leu Gln Lys Thr Leu Gln Thr Gln Thr Asn Ser Asn Asn
1400                1405                1410

Phe Lys Thr Lys Ala Ile Gln Glu Ile Glu Asn Ser Tyr Lys Arg
1415                1420                1425

Gly Met Glu Glu Leu Asn Phe Gln Lys Lys Glu Phe Asp Lys Asn
1430                1435                1440
```

-continued

```
Lys Ser Arg Leu Tyr Glu Tyr Phe Arg Lys Met Arg Asp Glu Ile
1445                1450                1455

Glu Arg Lys Glu Ser Gln Val Lys Leu Val Leu Lys Glu Thr Gln
1460                1465                1470

Arg Lys Ala Asn Leu Leu Glu Ala Gln Ala Asn Lys Leu Asn Ile
    1475                1480                1485

Glu Lys Asn Thr Ile Asp Phe Lys Glu Lys Glu Leu Lys Ala Phe
    1490                1495                1500

Lys Asp Lys Val Asp Gln Asp Ile Asp Ser Thr Asn Lys Gln Arg
1505                1510                1515

Lys Glu Leu Asn Glu Leu Leu Asn Glu Asn Lys Leu Leu Gln Gln
1520                1525                1530

Ser Leu Ile Glu Arg Glu Arg Ala Ile Asn Ser Lys Asp Ser Leu
1535                1540                1545

Leu Asn Lys Lys Ile Glu Thr Ile Lys Arg Gln Leu His Asp Lys
1550                1555                1560

Glu Met Arg Val Leu Arg Leu Val Asp Arg Met Lys Leu Ala Glu
1565                1570                1575

Gln Lys Tyr Gln Thr Glu Ile Asn Arg Leu Arg Thr Gln Thr Phe
1580                1585                1590

Asp Ser Glu Lys Gln Asp Ile Lys Asn Phe Phe Pro Pro Leu Phe
1595                1600                1605

Lys Ile Asn Gly Asn Asp Met Ala Phe Pro Tyr Leu Tyr Pro Trp
1610                1615                1620

Leu Tyr Pro Gln Gln Lys Gln Asp Asp Asn Thr Leu Gln Ile Arg
    1625                1630                1635

Gln Leu Phe Glu Gln Gln Leu Gln Phe Met Gln Gln Arg Tyr Glu
1640                1645                1650

Asn Glu Leu Asn Glu Leu Arg Arg Gln Arg Asn Leu Leu Glu Lys
1655                1660                1665

Lys Leu Asp Gln Ile Gln Leu Glu Ser Gln Leu Asn Asn Lys Gln
1670                1675                1680

Ser Glu Phe Ser Lys Val Ser Met Met Glu Lys Leu Leu Glu
1685                1690                1695

Lys Thr Glu Ser Arg Leu Asn Asp Phe Asp Gln Lys Ile Asn Tyr
1700                1705                1710

Leu Thr Lys Lys Val Asn Gln His Asn Thr Tyr Gln Pro Ser Ser
1715                1720                1725

Tyr Gln Pro Thr Pro Ser Tyr Gln Asp Ser Asp Lys Gln Gln Leu
1730                1735                1740

Leu Phe Arg Ile Gln Glu Leu Glu Lys Gln Asn Leu Phe Gln Gln
1745                1750                1755

Gln Phe Gln Pro Ala Pro Ala Val Val Gln Gln Pro Thr Ser Phe
1760                1765                1770

Ala Ala Pro Asn Ile Thr Lys Gln Gln Gln Ile Ala Gln Leu Asn
1775                1780                1785

Ala Glu Ile Asn Asn Ile Lys Arg Leu Ile Ala Gln Lys Ala Ala
1790                1795                1800

Ser Lys
1805
```

<210> SEQ ID NO 74
<211> LENGTH: 74
<212> TYPE: PRT

```
<213> ORGANISM: M. genitalium
<220> FEATURE:
<221> NAME/KEY: misc_feature
<223> OTHER INFORMATION: hypothetical protein
<221> NAME/KEY: misc_feature
<223> OTHER INFORMATION: gi[10]45811

<400> SEQUENCE: 74

Met Gln Tyr Ser Ala Leu Ile Pro Leu Phe Ile Leu Ile Ser Leu
1               5                   10                  15

Val Leu Phe Cys Phe Ser Phe Arg Lys Asn Gln Ser Glu Asn Gln Ile
            20                  25                  30

Val Lys Ile Leu Phe Phe Ala Tyr Cys Ile Asp Phe Leu Ala Leu Ile
        35                  40                  45

Leu Ala Val Met Leu Leu Thr Phe Leu Ser His Gly Leu Leu Ser Leu
    50                  55                  60

Ala Ile Leu Ile Pro Val Leu Val Phe Gln
65                  70

<210> SEQ ID NO 75
<211> LENGTH: 1033
<212> TYPE: PRT
<213> ORGANISM: M. pneumoniae
<220> FEATURE:
<221> NAME/KEY: misc_feature
<223> OTHER INFORMATION: MG328 homolog
<221> NAME/KEY: misc_feature
<223> OTHER INFORMATION: gi[16]74046

<400> SEQUENCE: 75

Met Glu Phe Leu Glu Gln Glu Gly Gln Glu Val Leu Thr Lys Glu Ile
1               5                   10                  15

Lys Ala Gly Phe Cys Glu Ile Thr Pro Ser Ser Ile Thr Glu Gln Thr
            20                  25                  30

Thr Lys Pro Gln Leu Asp Glu Thr Gln Leu Val Asp Glu Tyr Val His
        35                  40                  45

Thr Lys Glu Leu Glu Thr Thr Pro Ile Pro Ile Ser Phe Ala Thr Lys
    50                  55                  60

Glu Val Leu Phe Glu Glu Val Phe Asn Thr Pro Ser Thr Gln Gln Val
65                  70                  75                  80

Asp Glu Ser Val Leu Val Asn Glu Tyr Ile Glu Leu Thr Gln Gln Ile
                85                  90                  95

Lys Asn Ala Ser Glu Gln Val Ser Ser Asn His Thr His Lys Phe Ser
            100                 105                 110

Val Ala Thr Glu Pro Ala Ala Thr Lys Ala Val Ser Glu Thr Met Leu
        115                 120                 125

Leu Asp Asp Tyr Val Glu Met Val Glu Gln Asp Val Gln Ala Gln Thr
    130                 135                 140

Ala Leu Pro Gln Ala Ala Leu Asp Pro Thr Val Ser Leu Thr Phe Ser
145                 150                 155                 160

Ser Pro Ile Asp Ser Asn Ala Ile Leu Val Tyr Pro Glu Met Lys Val
                165                 170                 175

Pro His Val Phe Asp Thr Val Ala Pro Thr Thr Thr Val Pro Leu
            180                 185                 190

Asp Gln Thr Gln Leu Leu Asp Glu Leu Glu Val Pro Val Leu Thr
        195                 200                 205

His Thr Val Thr Pro Ala Pro Leu Gln Pro Lys Ala Ala Pro Thr Asn
    210                 215                 220
```

-continued

```
Phe Ala Leu Asp Gln Thr Gln Leu Val Asp Glu Leu Thr Val Pro
225                 230                 235                 240

Leu Thr His Thr Leu Val Asn Glu Ser Ala Pro Val Thr Pro Val Val
        245                 250                 255

Val Thr Ser Pro Ala Ala Glu His Ser Phe Ser Ile Thr Thr Val Asp
            260                 265                 270

Lys Ala Asn Leu Thr Asn Ala Leu Ser Gln Thr Val Val Ile Lys Pro
                275                 280                 285

Ala Glu Asp Ser Ala His Gln Ser Ala Val Leu Asp Lys Glu Ile Ala
    290                 295                 300

Thr Lys Gln Ala Gln Leu Gln Gln Leu Gln Ala Gln Ile Glu Leu Arg
305                 310                 315                 320

Gln Ala Gln Leu Glu Thr Pro Pro Val Thr Tyr Met Gly Val Glu Glu
                325                 330                 335

Tyr Lys Leu Leu Pro Val Gln Asp Val Pro Val Gln Pro Thr Val
                340                 345                 350

Ser Phe Glu Met Thr Leu Leu Gln Glu Gln Leu Asp Lys Ala Leu Lys
    355                 360                 365

His Asn Ala Ala Leu Gln Ile Gln Leu Glu Glu Gln Leu Ala Lys Pro
    370                 375                 380

Leu Gln Tyr Asp Gln Ser Pro Val Leu Gln Glu Arg Ile Glu Leu Leu
385                 390                 395                 400

Gln Asn Gln Asn Thr Asn Leu Thr Gln Glu Leu Asn Glu Leu Gln Gln
                405                 410                 415

Lys Leu Phe Lys Ser Gln Asn Asn Ser Leu Leu Leu Ala Arg Leu Glu
                420                 425                 430

Glu Glu Asn Arg Thr Leu Lys Gln His Leu Gln Asn Asn Leu Pro Glu
            435                 440                 445

Ala Asn Gln Leu Asn Phe Val Leu Glu Lys Gln Leu Glu Gln Leu Gln
450                 455                 460

Gln Asp Lys His Ser Leu Thr Leu Gln Ile Glu Gln Tyr Lys Phe Asp
465                 470                 475                 480

Ser Lys Lys His Gln Glu Gln Leu Ala Leu Ile Pro Ser Leu Arg Ser
                485                 490                 495

Glu Ile Asn Ser Leu Glu Thr Glu Val Ile Ser Leu Lys Gln Thr Asn
            500                 505                 510

Gln Arg Leu Ser Leu Ile Glu Arg Glu Asn Asn Phe Leu Lys Thr Glu
        515                 520                 525

Ile Lys Gln Leu Arg Glu Thr Lys Leu Asn Asp Glu Asn Thr Lys Tyr
530                 535                 540

Arg Asn Leu Leu Lys Gln Tyr Glu Leu Met Arg Ala Asp Ser Asp Ala
545                 550                 555                 560

Lys Leu Lys Glu Leu Glu His Glu Gln His Leu Ala His Gln His His
                565                 570                 575

Gln Glu Gln Leu Ala Gln Leu Gln Arg His Asn Glu Ala Leu Val Lys
            580                 585                 590

Glu Leu Asp Gln Val Lys Ala Thr Asn Phe Glu Leu Gly Leu Ala Ala
        595                 600                 605

Gln Gly Phe Glu Gln Lys Val Val Leu Glu Gln Lys Asn Ser Ser
    610                 615                 620

Leu Leu Ala Ser Leu Gln Ala Ala Glu Glu Asn Val Gln Ala Leu Gly
625                 630                 635                 640

Ile Thr Asn Ser Glu Leu Gln Asn Gln Leu Asn Val Leu Glu Phe Thr
```

|   |   |   |   |   |   |   |   |   |   |   |
|---|---|---|---|---|---|---|---|---|---|---|
| | | 645 | | | 650 | | | 655 | | |
| His | Lys | Glu | Lys | Thr | Ala | Phe | Asp | Ser | Lys | Thr | Leu | Thr | Leu | Thr | Lys |
| | | | 660 | | | | | 665 | | | | | 670 | | |

Gln Gln Leu Glu Gln Thr Gln Phe Asp Leu Ser Leu Thr Gln Glu Gln
                675                 680                 685

Leu Ala Thr Phe Lys Gln Gln Asn Gln Ser Leu Thr Asp Lys Leu Met
690                 695                 700

Ala Ser Glu Thr Gln Leu Asn His Leu Gln Gln Ser Asp Glu Asn Leu
705                 710                 715                 720

Thr Gln Leu Gln Thr Gln His Glu Leu Leu Gln Glu Ser Tyr Asn Lys
                725                 730                 735

Leu Gln Asp Glu Ala Asn His Thr Gln Gln Gln Phe His Gln Ala Gln
                740                 745                 750

Asn Glu Leu Asp Ala Ala His Gln Gln Leu Ala Leu Phe Lys Gln Asn
                755                 760                 765

Asn Glu Glu Leu Thr Asp Lys Cys Ser Asn Ile Gln Asn Glu Leu His
                770                 775                 780

Asp Leu Asn Arg Val Lys Thr Asn Trp Glu Asn Leu Asn Thr Glu His
785                 790                 795                 800

Asn Leu Leu Gln Asp Lys Tyr Ala Gln Lys Glu Gln Met Gln His
                805                 810                 815

Glu His Ser Asn Leu Ala Gln Ile Gln Ala Glu His Glu Leu Leu Gln
                820                 825                 830

Glu Ser Tyr Asn Lys Val Lys Ala Glu Leu Asn Glu Ile Gln Ile Thr
                835                 840                 845

Asn Leu Asn Glu Ala Asn Ala Gln Tyr Gln Asp Leu Leu Ser Ala Tyr
                850                 855                 860

Glu Leu Leu Gln Ser Asn His Asn Lys Leu Lys Gln Glu Leu Gln Val
865                 870                 875                 880

Leu Asn Gln Val Asn Leu Glu Lys Gln Gln Leu Ala Gln Lys Leu His
                885                 890                 895

Asn Thr His Gln Ser Leu Ser Gln Thr His Ala Glu Leu Thr Gln Leu
                900                 905                 910

Gln Ala Ala Tyr Asn Asn Leu Gln Ala Thr Pro Pro Val Ser Asp Glu
                915                 920                 925

Leu Leu Glu Gln Phe Asn Gln Val Gln Leu Glu Lys Gln Arg Leu Leu
                930                 935                 940

Gln Gln Asn Leu Ala Leu Val His Glu Leu Gln Tyr Phe Asn Glu Leu
945                 950                 955                 960

Asn Ser Ser Gln Thr His Glu Ile Lys Thr Lys Gln Asp Glu Thr Val
                965                 970                 975

Lys Glu Val Ile Ile Val Glu Lys Glu Ile Pro Val Pro Pro Glu Lys
                980                 985                 990

Lys Pro Arg Leu Lys Lys Arg Asp Ile Val Ile Glu Asn Lys Glu Asp
                995                 1000                1005

Ala Leu Gly Lys Leu Ser Lys Lys Glu Arg Ile Gln Ala Tyr Ala
        1010                1015                1020

Glu Arg Leu Ala Lys Ile Asn Gly Lys Gln
        1025                1030

<210> SEQ ID NO 76
<211> LENGTH: 22
<212> TYPE: PRT
<213> ORGANISM: M. pneumoniae

```
<220> FEATURE:
<221> NAME/KEY: misc_feature
<223> OTHER INFORMATION: A05_orf139 Protein
<221> NAME/KEY: misc_feature
<223> OTHER INFORMATION: gi[16]73719

<400> SEQUENCE: 76

Met Arg Trp Cys Arg Gly Ser Pro Tyr His Trp Asn Leu Asp Arg Arg
1               5                   10                  15

Asn Pro Asp Phe Pro Ala
            20

<210> SEQ ID NO 77
<211> LENGTH: 103
<212> TYPE: PRT
<213> ORGANISM: M. pneumoniae
<220> FEATURE:
<221> NAME/KEY: misc_feature
<223> OTHER INFORMATION: B01_orf103b Protein
<221> NAME/KEY: misc_feature
<223> OTHER INFORMATION: gi[16]73772

<400> SEQUENCE: 77

Met Ser Ser Val Phe Ser Lys Pro Asn Leu Lys Arg Pro Ser Phe Asp
1               5                   10                  15

Val Lys Asn Leu Thr Lys Pro Ser Arg Leu Leu Ser Ala Thr Leu Arg
            20                  25                  30

Ser Ser Cys Ala Phe Leu Ser Ser Ala Ser Phe Phe Ala Cys Ser Leu
        35                  40                  45

Cys Phe Phe Cys Cys Ser Ser Ile Ser Phe Cys Ser Leu Ala Ser Ser
    50                  55                  60

Ser Ala Arg Leu Arg Tyr Ser Ser Ser His Ser Phe Phe Cys Trp Val
65                  70                  75                  80

Leu Phe Ser Arg Ser Gly Leu Ala Tyr Ser Ser Ser Asn Leu Ser Ser
                85                  90                  95

Lys Ser Ser Arg Leu Arg Ser
            100

<210> SEQ ID NO 78
<211> LENGTH: 112
<212> TYPE: PRT
<213> ORGANISM: M. pneumoniae
<220> FEATURE:
<221> NAME/KEY: misc_feature
<223> OTHER INFORMATION: VXpSPT7_orf112 Protein
<221> NAME/KEY: misc_feature
<223> OTHER INFORMATION: gi[16]74374

<400> SEQUENCE: 78

Met Ile Asp Arg Phe Phe Trp Ser Ile Leu Ser Phe Leu Leu Thr Asn
1               5                   10                  15

Leu Val Phe Leu Phe Val Ala Phe Leu Ile Leu Ile Ile Tyr Leu Ile
            20                  25                  30

Ser Glu Ile Thr Gln Gln Phe Ala Phe Ala Phe Ile Ala Thr Ile Val
        35                  40                  45

Phe Ile Ile Phe Tyr Asn Ile Leu Phe Leu Ser Tyr Leu Leu Thr Met
    50                  55                  60

Tyr Ile Lys Gly Leu Lys Gln Ile Glu Gln Lys Ser Arg Tyr Leu Leu
65                  70                  75                  80

Leu Val Leu Asp Val Lys Ala Asp Glu Leu Leu Pro Phe Ser Phe Leu
                85                  90                  95
```

```
Gly Ser Leu Arg Lys Ser His Met Leu Glu Glu Met Leu Leu Glu Gln
                100                 105                 110

<210> SEQ ID NO 79
<211> LENGTH: 147
<212> TYPE: PRT
<213> ORGANISM: M. pneumoniae
<220> FEATURE:
<221> NAME/KEY: misc_feature
<223> OTHER INFORMATION: B01_orf147 Protein
<221> NAME/KEY: misc_feature
<223> OTHER INFORMATION: gi[16]73775

<400> SEQUENCE: 79

Met Pro Ser Ser Ala Phe Lys Ile Asn Leu Ser Val Ser Pro Trp Phe
1               5                   10                  15

Phe Cys Ser Thr Trp Ser Ser Leu Ile Cys Trp Pro Trp Thr Ile Thr
                20                  25                  30

Thr Ser Val Ser Arg Ser Thr Leu Ser Ser Thr Thr Trp Ile Leu Trp
            35                  40                  45

Thr Trp Leu Phe Asn Ser Val Ser Ile Phe Val Ser Arg Trp Ser Phe
    50                  55                  60

Asp Phe Leu Tyr Ser Leu Asn Ser Leu Arg Val Thr Tyr Ser Val Phe
65                  70                  75                  80

Thr Gly Ile Thr Gly Leu Leu Ser Leu Asn Cys Leu Leu Lys Leu Pro
                85                  90                  95

Glu Asn Ser Thr Leu Leu Leu Ser Leu Ser Ile Ile Tyr Gln Pro Glu
                100                 105                 110

Lys Val Pro Phe Trp Ser Phe Ser Pro Cys His Glu Ile Leu Phe Arg
            115                 120                 125

Tyr Lys Thr Glu Phe Ser Leu Ser Leu Ser His Thr Ser Phe Leu Phe
    130                 135                 140

Ser Glu Ile
145

<210> SEQ ID NO 80
<211> LENGTH: 217
<212> TYPE: PRT
<213> ORGANISM: M. tuberculosis
<220> FEATURE:
<221> NAME/KEY: misc_feature
<223> OTHER INFORMATION: hypothetical protein Rv3611
<221> NAME/KEY: misc_feature
<223> OTHER INFORMATION: gi[21]13965

<400> SEQUENCE: 80

Met Ala Ile Ala Asn Pro Ala Glu Pro Gly Ala Ala Gly Arg His His
1               5                   10                  15

Gln Pro Arg Gly Asp Arg Lys Pro Arg Ala Trp Arg Gln Cys Gly Pro
                20                  25                  30

Gln Asn Gly Pro Arg Arg Ser Gln Ala Ile Thr Pro Glu Pro Gly Ala
            35                  40                  45

Ala Gly Arg His His Gln Pro Arg Gly Asp Arg Lys Pro Arg Ala Trp
    50                  55                  60

Arg Gln Cys Gly Pro Gln Asn Gly Pro Arg Arg Ser Gln Ala Ile Thr
65                  70                  75                  80

Pro Glu Pro Gly Ala Ala Gly Arg His His Gln Pro Arg Gly Asp Arg
                85                  90                  95

Lys Pro Arg Ala Trp Arg Gln Cys Gly Pro Gln Asn Gly Pro Arg Arg
                100                 105                 110
```

-continued

```
Ser Gln Ala Ile Thr Pro Glu Pro Gly Ala Ala Gly Arg His His Gln
        115                 120                 125

Pro Arg Gly Asp Arg Lys Pro Arg Ala Trp Arg Gln Cys Gly Pro Gln
    130                 135                 140

Asn Gly Pro Arg Arg Ser Gln Ala Ile Thr Pro Glu Pro Gly Ala Ala
145                 150                 155                 160

Gly Arg His His Gln Pro Arg Gly Asp Arg Lys Pro Arg Ala Trp Arg
                165                 170                 175

Gln Cys Gly Pro Gln Asn Gly Pro Arg Arg Ser Gln Ala Ile Thr Pro
            180                 185                 190

Glu Pro Gly Ala Ala Gly Arg His Trp Leu Asp Gln Arg Pro Val Val
        195                 200                 205

Pro Asp Gly Val Gly Lys Ser Asp Ser
    210                 215

<210> SEQ ID NO 81
<211> LENGTH: 27
<212> TYPE: PRT
<213> ORGANISM: M. tuberculosis
<220> FEATURE:
<221> NAME/KEY: misc_feature
<223> OTHER INFORMATION: hypothetical protein Rv1572c
<221> NAME/KEY: misc_feature
<223> OTHER INFORMATION: gi[21]17265

<400> SEQUENCE: 81

His Gly Gln Pro Arg Thr Asn Thr Phe His His Glu Lys Leu Leu
1               5                   10                  15

Arg His Asn Asp Glu Asp Asn His Asp Pro
            20                  25

<210> SEQ ID NO 82
<211> LENGTH: 73
<212> TYPE: PRT
<213> ORGANISM: M. tuberculosis
<220> FEATURE:
<221> NAME/KEY: misc_feature
<223> OTHER INFORMATION: hypothetical protein Rv0378
<221> NAME/KEY: misc_feature
<223> OTHER INFORMATION: gi[29]09499

<400> SEQUENCE: 82

Met Ser Gly Arg Trp Glu Ala Gly Asn Ala Asp Gly Asn Gly Ser
1               5                   10                  15

Ala Gly Leu Ile Gly Ser Gly Gly Ala Gly Gly Asp Gly Gly Ser Gly
            20                  25                  30

Gly Ala Thr Gly Ala Gly Gly Glu Gly Gly Asp Ala Gly Ala Ser Gly
        35                  40                  45

Ser Ile Asn Gly Asn Ala Gly Asp Pro Gly Asn Ser Gly Glu Arg Gly
    50                  55                  60

Ala Val Gly Lys Pro Gly Ala Pro Gly
65                  70

<210> SEQ ID NO 83
<211> LENGTH: 47
<212> TYPE: PRT
<213> ORGANISM: N. meningitis MC58
<220> FEATURE:
<221> NAME/KEY: misc_feature
<223> OTHER INFORMATION: hypothetical protein
<221> NAME/KEY: misc_feature
<223> OTHER INFORMATION: gi[72]25315
```

```
<400> SEQUENCE: 83

Met Glu Trp Ala Glu Asn Glu Thr Val Lys Leu Ala Gln Lys Trp Glu
1               5                   10                  15

Gln Glu Gln Lys Lys Gln Gln Ile Gln Lys Lys Glu Thr Glu Lys
            20                  25                  30

Ser Pro Lys His Lys Ala Ser Arg Asp Asp Trp Glu Met Glu Arg
        35                  40                  45

<210> SEQ ID NO 84
<211> LENGTH: 107
<212> TYPE: PRT
<213> ORGANISM: N. meningitis MC58
<220> FEATURE:
<221> NAME/KEY: misc_feature
<223> OTHER INFORMATION: hypothetical protein
<221> NAME/KEY: misc_feature
<223> OTHER INFORMATION: gi[72]26708

<400> SEQUENCE: 84

Met Lys Lys Leu Leu Ile Ala Ala Met Met Ala Ala Ala Leu Ala Ala
1               5                   10                  15

Cys Ser Gln Glu Ala Lys Gln Glu Val Lys Glu Ala Val Gln Ala Val
            20                  25                  30

Glu Ser Asp Val Lys Asp Thr Ala Ala Ser Ala Ala Glu Ser Ala Ala
        35                  40                  45

Ser Ala Val Glu Glu Ala Lys Asp Gln Val Lys Asp Ala Ala Ala Asp
50                  55                  60

Ala Lys Ala Ser Ala Glu Gly Ala Val Thr Glu Ala Lys Glu Ala Val
65                  70                  75                  80

Thr Glu Ala Ala Lys Asp Thr Leu Asn Lys Ala Ala Asp Ala Thr Gln
            85                  90                  95

Glu Ala Ala Asp Lys Met Lys Asp Ala Ala Lys
            100                 105

<210> SEQ ID NO 85
<211> LENGTH: 98
<212> TYPE: PRT
<213> ORGANISM: N. meningitis MC58
<220> FEATURE:
<221> NAME/KEY: misc_feature
<223> OTHER INFORMATION: hypothetical protein
<221> NAME/KEY: misc_feature
<223> OTHER INFORMATION: gi[72]26768

<400> SEQUENCE: 85

Met Lys Lys Ser Leu Phe Ala Ala Ala Leu Leu Ser Leu Val Leu Ala
1               5                   10                  15

Ala Cys Gly Gly Glu Lys Ala Ala Glu Ala Pro Ala Ala Glu Ala Pro
            20                  25                  30

Ala Ala Glu Ala Pro Ala Thr Glu Pro Ala Ala Glu Ala Pro Ala
        35                  40                  45

Ala Glu Ala Pro Ala Ala Glu Ala Pro Ala Ala Glu Ala Ala Thr
50                  55                  60

Glu Ala Pro Ala Ala Glu Ala Ala Thr Glu Ala Pro Ala Ala Glu
65                  70                  75                  80

Ala Ala Ala Thr Glu Ala Pro Ala Ala Glu Ala Pro Ala Ala Glu Ala
            85                  90                  95

Ala Lys
```

```
<210> SEQ ID NO 86
<211> LENGTH: 34
<212> TYPE: PRT
<213> ORGANISM: N. meningitis MC58
<220> FEATURE:
<221> NAME/KEY: misc_feature
<223> OTHER INFORMATION: hypothetical protein
<221> NAME/KEY: misc_feature
<223> OTHER INFORMATION: gi[72]27030

<400> SEQUENCE: 86

Met Pro Trp Lys Ile Ser Thr Thr Thr Asn Leu Thr Pro Val Pro Ser
1               5                   10                  15

Ala Asn Leu Ser Ala Leu Pro Thr Thr Arg Cys Thr Thr Pro Pro Pro
            20                  25                  30

Thr Pro

<210> SEQ ID NO 87
<211> LENGTH: 114
<212> TYPE: PRT
<213> ORGANISM: N. meningitis MC58
<220> FEATURE:
<221> NAME/KEY: misc_feature
<223> OTHER INFORMATION: hypothetical protein
<221> NAME/KEY: misc_feature
<223> OTHER INFORMATION: gi[72]27104

<400> SEQUENCE: 87

Met Gly Ile Pro Glu Ser Ser Gly Ile Pro Glu Ser Ser Gly Ile Pro
1               5                   10                  15

Glu Ser Ser Gly Ile Pro Glu Ser Ser Gly Ile Pro Glu Ser Ser Gly
            20                  25                  30

Ile Pro Glu Ser Ser Gly Ile Pro Glu Ser Ser Gly Ile Pro Glu Ser
        35                  40                  45

Ser Gly Ile Pro Glu Ser Ser Gly Ile Pro Glu Ser Ser Gly Ile Pro
    50                  55                  60

Glu Ser Ser Gly Ile Pro Glu Ser Ser Gly Ile Pro Glu Ser Ser Gly
65                  70                  75                  80

Ile Pro Glu Ser Ser Gly Ile Pro Glu Ser Ser Gly Ile Pro Glu Pro
                85                  90                  95

Ser Phe Pro Arg Arg Arg Glu Ser Arg Pro Val Gly Ala Glu Thr Tyr
            100                 105                 110

Arg Val

<210> SEQ ID NO 88
<211> LENGTH: 120
<212> TYPE: PRT
<213> ORGANISM: N. meningitis MC58
<220> FEATURE:
<221> NAME/KEY: misc_feature
<223> OTHER INFORMATION: hypothetical protein
<221> NAME/KEY: misc_feature
<223> OTHER INFORMATION: gi[72]26645

<400> SEQUENCE: 88

Met Ile Ala Lys Ser Leu Phe Phe Arg Cys Gln Lys Ile Tyr Phe Ile
1               5                   10                  15

Tyr Phe Ile Leu Phe Ile Cys Leu Tyr Leu Asn Ile Ser Tyr Asp Gly
            20                  25                  30

Glu Ile Phe Ile Tyr Phe Ile Ile Asn Phe Thr His Leu Leu Ile Cys
        35                  40                  45
```

-continued

```
His Gly Ile Leu Leu Val Phe Cys Arg Ile Phe Pro Tyr Glu Asn Ile
            50                  55                  60

Pro Phe Thr Ile Phe Leu Asn Phe Ile Ser Leu Phe Leu Ile Phe Leu
 65                  70                  75                  80

Pro Leu Ile Phe Thr Ile Arg Glu Leu Ile Asp Ser Tyr Tyr Ile Glu
                85                  90                  95

Ser Ile Ile Asn Leu Phe Leu Ile Leu Ile Pro His Val Ile Phe Leu
                100                 105                 110

Ile Tyr Leu Lys Gly Lys Gln Ile
        115                 120

<210> SEQ ID NO 89
<211> LENGTH: 78
<212> TYPE: PRT
<213> ORGANISM: Pseudomonas aeruginosa
<220> FEATURE:
<221> NAME/KEY: misc_feature
<223> OTHER INFORMATION: AE004587_5 hypothetical protein
<221> NAME/KEY: misc_feature
<223> OTHER INFORMATION: gi[99]47556

<400> SEQUENCE: 89

Met Lys Lys Thr Val Thr Leu Ala Leu Leu Leu Ala Ala Ser Leu Gly
 1               5                  10                  15

Leu Ala Ala Cys Asp Lys Lys Glu Glu Asp Lys Ala Ala Ala Pro Ala
                20                  25                  30

Ala Pro Ala Thr Glu Thr Gln Pro Ser Ala Pro Ala Thr Pro Pro Ala
                35                  40                  45

Glu Pro Ser Ala Pro Ala Pro Ser Ser Asp Thr Pro Ala Thr Pro Gln
            50                  55                  60

Thr Pro Ala Pro Thr Pro Glu Gln Pro Gln Gln Asn Gln Gln
 65                  70                  75

<210> SEQ ID NO 90
<211> LENGTH: 52
<212> TYPE: PRT
<213> ORGANISM: Pseudomonas aeruginosa
<220> FEATURE:
<221> NAME/KEY: misc_feature
<223> OTHER INFORMATION: AE004746_3 hypothetical protein
<221> NAME/KEY: misc_feature
<223> OTHER INFORMATION: gi[99]49353

<400> SEQUENCE: 90

Met Ser Leu Gly Thr Ile Leu Leu Ile Ile Leu Ile Leu Leu Leu Ile
 1               5                  10                  15

Gly Gly Leu Pro Val Phe Pro His Ser Arg Asn Trp Gly Tyr Gly Pro
                20                  25                  30

Ser Gly Ile Ile Gly Ala Leu Leu Val Val Leu Leu Val Leu Leu Leu
            35                  40                  45

Leu Gly Met Ile
        50

<210> SEQ ID NO 91
<211> LENGTH: 126
<212> TYPE: PRT
<213> ORGANISM: Pseudomonas aeruginosa
<220> FEATURE:
<221> NAME/KEY: misc_feature
<223> OTHER INFORMATION: AE004708_10 hypothetical protein
<221> NAME/KEY: misc_feature
<223> OTHER INFORMATION: gi[99]48900
```

```
<400> SEQUENCE: 91

Met Leu Lys Leu Phe Ala Thr Gly Leu Ala Ala Ser Phe Leu Leu Leu
1               5                   10                  15

Pro Pro Ala Gln Ala Ala Pro Pro Ala Pro Tyr Gly Val Gln Pro His
            20                  25                  30

Gln Gln Ala Val Gln Arg Ala Gly Glu Gln Arg Gln Arg Gln Leu Gln
        35                  40                  45

Glu Gln Arg Gln Arg Phe Asp Glu Gln Arg Leu Gln Leu Gln Gln Asp
    50                  55                  60

Gln Leu Gln Arg Gln Gln Asn Leu Gln Arg Gln Arg Gln Gln Arg
65                  70                  75                  80

Gln Met Gln Asp Asn Leu Ile Arg Gln Gln Leu Asp Gln Arg
                85                  90                  95

Trp Arg Leu Glu Gln Asp Gln Arg Arg Leu Asp Ser Glu Arg Arg Gln
            100                 105                 110

Leu Glu Asn Arg Arg Arg Gln Ser Gln Ser Pro Ala Ile Arg
            115                 120                 125

<210> SEQ ID NO 92
<211> LENGTH: 101
<212> TYPE: PRT
<213> ORGANISM: Pseudomonas aeruginosa
<220> FEATURE:
<221> NAME/KEY: misc_feature
<223> OTHER INFORMATION: AE004643_2 hypothetical protein
<221> NAME/KEY: misc_feature
<223> OTHER INFORMATION: gi[99]48180

<400> SEQUENCE: 92

Met Ser Ala Asp Glu Lys Arg Ile Arg Glu Phe Ala Tyr Gln Ile Trp
1               5                   10                  15

Glu Ser Glu Gly Cys Pro Asp Gly Gln Ala Glu Arg His Trp Ala Met
            20                  25                  30

Ala Arg Gln Leu Ala Glu Ala Glu Ala Ala Ala Pro Lys Lys
        35                  40                  45

Thr Arg Gly Arg Ala Lys Ala Lys Glu Thr Pro Ala Leu Leu Gln
    50                  55                  60

Ala Pro Ala Ala Lys Pro Arg Lys Pro Arg Ala Ala Ser Pro Ala Arg
65                  70                  75                  80

Pro Ala Ser Glu Lys Pro Ala Ala Lys Pro Arg Ser Arg Arg Lys
                85                  90                  95

Pro Glu Ala Gly Glu
            100

<210> SEQ ID NO 93
<211> LENGTH: 521
<212> TYPE: PRT
<213> ORGANISM: R. prowazekii
<220> FEATURE:
<221> NAME/KEY: misc_feature
<223> OTHER INFORMATION: unknown
<221> NAME/KEY: misc_feature
<223> OTHER INFORMATION: gi[38]60652

<400> SEQUENCE: 93

Met Lys Lys Glu Ile Leu Ser Lys Gln Gly Asn Ile Leu Glu Gln Leu
1               5                   10                  15

Lys Phe Ile Asn Ala Asn Thr Glu Ile Leu Thr Glu His Ser Lys Ala
            20                  25                  30
```

-continued

```
Ile Leu Lys Asp Lys Leu Lys Glu Leu Ser Lys Gln Leu Asp Glu Ile
        35                  40                  45
Ser Ser Asn Lys Leu Val Gly Phe Ile Leu Asp Glu Asn Lys Ile Asn
 50                  55                  60
Thr Asn Phe Lys Asn Val Pro Phe Ser Glu Lys Lys Val Arg Glu Gln
 65                  70                  75                  80
Val Asn Asn Leu Asn Asn Lys Ile Leu Glu Lys Ile Phe Leu Lys Asp
                85                  90                  95
Asp Gly Thr Ile Thr Glu Gln Asp Leu Thr Lys Ile Leu Gln Lys His
                100                 105                 110
Lys Glu Thr Val Leu Ile Lys Asn Leu Thr Lys Ala Ile Val Tyr Ile
            115                 120                 125
Asp Gly Asn Lys Asn Asn Glu Thr Val Asn Lys Thr Leu Glu Lys Cys
130                 135                 140
Leu Glu Glu Thr Thr Pro Glu Gln Gln Gly Met Ile Leu Asp Val Leu
145                 150                 155                 160
Thr Asn Asn Thr Arg Ile Arg Lys Ala Leu Ile Thr Lys Ile Glu Arg
                165                 170                 175
Glu Gln Arg Gln Glu His Asn Gln Lys Leu Asn Lys Asn Ile Ala Gly
            180                 185                 190
Asp Thr Phe Val Asp Ala Leu Lys Lys Ala Leu Val His Arg Thr Ser
            195                 200                 205
Asn Pro Glu Thr Ile Gln Lys Ser Leu Glu Arg Arg Lys Lys Glu Thr
            210                 215                 220
Pro Lys Asn Leu Asn Val Trp Asp Arg Ile Ser Gln Asn Ile Pro Asn
225                 230                 235                 240
Leu Asn Asn Gln Asn Asp Asn Gln Asn Gly Gln Asp Glu Asn Asn Lys
                245                 250                 255
Glu Trp Glu Glu Ser Asn Gln Asn Ala Asp Tyr Leu Asn Asn Thr Asn
            260                 265                 270
Ile Tyr Arg Ile Thr Lys Ala Lys Gln Asp Leu Glu Lys Ala Val Lys
            275                 280                 285
Glu Thr Ile Asn Lys Phe Ser Ala Met Ser Thr Leu Ile Lys Asp Asn
            290                 295                 300
Thr Ile Lys Asn Thr Met Ala Tyr Gln Lys Tyr Leu Lys Gly Ala Glu
305                 310                 315                 320
Asp Gln Leu Ala Leu Ala Lys Glu Lys Gly Lys Glu Leu Ile Glu Asn
                325                 330                 335
Ser Val Gln Thr Phe Lys Ile Ile Pro Lys Lys Tyr Gln Asp Asp Met
            340                 345                 350
Asn Glu Asn Trp Gln Asn Tyr Leu Ser Pro Glu Glu Ile Ile Glu Leu
            355                 360                 365
Thr Ala Leu Asn Glu His Thr Asn Thr Leu Thr Ser Asn Lys Asn Lys
        370                 375                 380
Ser Gly Tyr Phe Thr Ser Thr Ala Glu Ala Leu Gln Cys Lys Thr Lys
385                 390                 395                 400
Gln Gln Glu Tyr Tyr Thr Leu Leu Ser Lys Leu Lys Lys Ile Gly Ile
                405                 410                 415
Glu Lys Gln Gln Lys Lys Leu Val Lys Asp Tyr Val Asp Glu Met Ile
            420                 425                 430
Thr Asn Ala Lys Gln Ala Val Lys Lys Ile Glu Arg Thr Leu Glu Lys
            435                 440                 445
Val Asn Gln Lys Lys Glu Asn Lys Tyr Glu Phe Ser Glu Ser Ser Ala
```

```
                450             455             460
Leu Ile Ser Lys Glu Ile Leu Asp Ala Gln Ala Arg Leu Glu Asn Ala
465                 470                 475                 480

Lys Gln Lys Ile Glu Phe Ile Lys Leu Lys Gln Ile Ile Ser Asp Lys
                485                 490                 495

Arg Gln Val Asn Ser Ser Asp Glu Asp Ser Asp Asp Asp Ser Lys Lys
            500                 505                 510

Lys Cys Asn Gln Thr Lys Ser Arg Thr
        515                 520

<210> SEQ ID NO 94
<211> LENGTH: 143
<212> TYPE: PRT
<213> ORGANISM: R. prowazekii
<220> FEATURE:
<221> NAME/KEY: misc_feature
<223> OTHER INFORMATION: unknown
<221> NAME/KEY: misc_feature
<223> OTHER INFORMATION: gi[38]60651

<400> SEQUENCE: 94

Met Lys Ile Gln Met Met Ile Leu Lys Lys Asn Ala Ile Lys Leu Lys
1               5                   10                  15

Val Glu Leu Glu Asn Ala Gln Lys Asp Ile Asn Gln Ala Lys Lys Asn
            20                  25                  30

Leu Glu Asn Ala Glu Ala Lys Asn Glu Ala Leu Gln Arg Gln Ile Ile
        35                  40                  45

Leu Asn His Asn Gln Asn Glu Val Asn Ser His Thr Thr Lys Asn Gln
50                  55                  60

Glu Lys Phe Lys Thr Asp Asn Val Thr Glu Glu Tyr Leu Glu Asp Met
65                  70                  75                  80

Ala Leu Met Phe Lys Asn Ser Glu Asp Thr Ala Glu Gln Lys Glu Glu
                85                  90                  95

Val Asn Cys Gln His His Glu Glu Gln Asn Arg Gln Lys Gln Glu His
            100                 105                 110

Ile Asn Thr Glu Glu Glu Ala Val His Lys Glu Lys Ile Ile His Ile
        115                 120                 125

Thr Glu Glu Thr Glu Thr Glu Ala Phe Lys Lys Glu Ile Asp Leu
    130                 135                 140

<210> SEQ ID NO 95
<211> LENGTH: 369
<212> TYPE: PRT
<213> ORGANISM: T. pallidum
<220> FEATURE:
<221> NAME/KEY: misc_feature
<223> OTHER INFORMATION: conserved hypothetical protein
<221> NAME/KEY: misc_feature
<223> OTHER INFORMATION: gi[33]22751

<400> SEQUENCE: 95

Met Cys Gln Lys Ser Ser Pro Cys Thr Tyr Ala Arg Val Arg Ser Leu
1               5                   10                  15

Pro Ser Val Arg Leu Phe Ser Phe Leu Ala Leu Ala Phe Ala Ser Phe
            20                  25                  30

Leu Arg Ala Glu Asp Ala Phe Asp His Phe Arg Glu Gly Glu Arg Leu
        35                  40                  45

Leu Ser Leu Gln Gln Ala Gln Gln Ala Ile Gly Pro Leu His Lys Ala
50                  55                  60
```

```
Ala Gln Gln Lys Pro Ala His Pro Lys Ala Ala Leu Tyr Leu Gly Met
 65                  70                  75                  80

Ala Tyr Leu Gln Thr Gly Arg Tyr Thr Gln Ala Ile Gln Trp Leu Gln
                 85                  90                  95

Asn Pro Pro Val His Ser Gln Glu Tyr Ala His Leu Tyr Ala Tyr Asn
            100                 105                 110

Leu Gly Asn Val Tyr Phe Val Gln His Arg Tyr Glu Glu Ala Gln His
        115                 120                 125

Ala Tyr Glu Gln Ala Leu Ala Leu Lys His Asp Tyr Pro Pro Ala Leu
    130                 135                 140

Leu Asn Arg Ala Asn Thr Ala Met Lys Arg Gln Ala Tyr Ala His Ala
145                 150                 155                 160

Leu Ala Asp Tyr Lys Lys Tyr Val Ser Gln Asn Pro Thr Ala Ser Gln
                165                 170                 175

His Tyr Glu Val Gln Arg Met Ile Ala Ala Leu Glu Gln Trp Leu Gln
            180                 185                 190

Arg Lys Glu Ala Glu Glu Ala Arg Lys Glu Ala Glu Glu Ala Arg
        195                 200                 205

Arg Lys Glu Ala Glu Glu Ala Arg Arg Lys Glu Ala Glu Glu Ala Arg
210                 215                 220

Arg Lys Glu Ala Glu Glu Ala Arg Arg Lys Glu Ala Glu Glu Ala Arg
225                 230                 235                 240

Arg Lys Glu Ala Glu Glu Ala Arg Arg Lys Glu Ala Glu Glu Ala Arg
                245                 250                 255

Arg Lys Glu Ala Glu Glu Ala Arg Arg Lys Glu Ala Glu Glu Ala Arg
            260                 265                 270

Arg Lys Glu Ala Glu Glu Ala Arg Arg Lys Glu Ala Glu Glu Ala Arg
        275                 280                 285

Arg Lys Glu Ala Glu Glu Ala Arg Arg Lys Glu Ala Glu Glu Ala Arg
    290                 295                 300

Arg Lys Glu Ala Glu Glu Ala Arg Arg Lys Glu Ala Glu Glu Ala Arg
305                 310                 315                 320

Arg Lys Glu Ala Glu Glu Ala Arg Arg Lys Glu Ala Glu Phe Glu Ala
                325                 330                 335

Leu Lys Arg Ala Leu Arg Leu Lys Gln Ala Glu Asp Ala Arg Thr Leu
            340                 345                 350

Ser Thr Gly Ser Glu Asp Thr Val Pro Tyr Gln Glu Glu His Asn Leu
        355                 360                 365

Glu

<210> SEQ ID NO 96
<211> LENGTH: 41
<212> TYPE: PRT
<213> ORGANISM: T. pallidum
<220> FEATURE:
<221> NAME/KEY: misc_feature
<223> OTHER INFORMATION: predicted coding region TP0266
<221> NAME/KEY: misc_feature
<223> OTHER INFORMATION: gi[33]22546

<400> SEQUENCE: 96

Met Val Arg Val Gln Arg Arg Val Leu Lys Asn Phe Met Arg Val Val
  1               5                  10                  15

Gly Val Asp Lys Gly Tyr Arg Leu Trp Val Glu Trp Leu Ser Cys Val
             20                  25                  30

Cys Cys Gly Tyr Val Val Arg Ala Glu
```

```
<210> SEQ ID NO 97
<211> LENGTH: 38
<212> TYPE: PRT
<213> ORGANISM: Vibrio cholerae
<220> FEATURE:
<221> NAME/KEY: misc_feature
<223> OTHER INFORMATION: hypothetical protein
<221> NAME/KEY: misc_feature
<223> OTHER INFORMATION: gi[96]54409

<400> SEQUENCE: 97

Met Ser Lys Gln Glu Met Lys Lys Pro Gln Leu Ser Leu Lys Glu Lys
 1               5                  10                  15

Arg Lys Leu Lys Gln Glu Lys Ala Gln Glu Ser Ser Val Ile Lys Pro
            20                  25                  30

Arg Lys Ser Lys Gly Arg
        35

<210> SEQ ID NO 98
<211> LENGTH: 85
<212> TYPE: PRT
<213> ORGANISM: Vibrio cholerae
<220> FEATURE:
<221> NAME/KEY: misc_feature
<223> OTHER INFORMATION: hypothetical protein
<221> NAME/KEY: misc_feature
<223> OTHER INFORMATION: gi[96]54544

<400> SEQUENCE: 98

Met Phe Leu Ser Phe Ile Cys Phe Tyr Ile Phe Lys Asn Gly Ser Tyr
 1               5                  10                  15

Phe Ser Phe Ile Cys Leu Val Gly Cys Phe Gln Phe Asp Phe Phe
            20                  25                  30

Val Val Val Phe Ile Gly Phe Leu Phe Leu Phe Cys Ser Phe Gly Leu
        35                  40                  45

Val Asp Phe Ser Phe Phe Tyr Phe Val Leu Ile Val Phe His Leu Phe
    50                  55                  60

Gly Val Asp Leu Leu Ser Trp Phe Gly Trp Trp Gln Val Phe Leu Phe
65                  70                  75                  80

Cys Asn Phe Ile Glu
                85

<210> SEQ ID NO 99
<211> LENGTH: 43
<212> TYPE: PRT
<213> ORGANISM: Vibrio cholerae
<220> FEATURE:
<221> NAME/KEY: misc_feature
<223> OTHER INFORMATION: hypothetical protein
<221> NAME/KEY: misc_feature
<223> OTHER INFORMATION: gi[96]54912

<400> SEQUENCE: 99

Met Leu Asn His Leu Leu Val Arg Leu Thr Ile Gly Cys Leu Leu Val
 1               5                  10                  15

Leu Gly Ile Lys Leu Ser Ala Leu Tyr Phe Leu Pro Met Val Leu Leu
            20                  25                  30

Leu Asn Thr His His Lys Glu Phe Phe Gly Trp
        35                  40

<210> SEQ ID NO 100
```

-continued

```
<211> LENGTH: 31
<212> TYPE: PRT
<213> ORGANISM: Vibrio cholerae
<220> FEATURE:
<221> NAME/KEY: misc_feature
<223> OTHER INFORMATION: hypothetical protein
<221> NAME/KEY: misc_feature
<223> OTHER INFORMATION: gi[96]56707

<400> SEQUENCE: 100

Met Pro Arg His Pro Phe Val Phe Val Val Ile Pro Lys Pro Pro Phe
1               5                   10                  15

Leu Ala Val Val Ile Val Leu Arg Phe Val Val Thr Arg Tyr Leu
            20                  25                  30

<210> SEQ ID NO 101
<211> LENGTH: 88
<212> TYPE: PRT
<213> ORGANISM: Vibrio cholerae
<220> FEATURE:
<221> NAME/KEY: misc_feature
<223> OTHER INFORMATION: hypothetical protein
<221> NAME/KEY: misc_feature
<223> OTHER INFORMATION: gi[96]57609

<400> SEQUENCE: 101

Met Leu Ser Leu Ala Val Pro Leu Leu Phe Met Ser Leu Leu Gly Phe
1               5                   10                  15

Lys Leu Lys Leu Pro Tyr Gly Leu Leu Met Gly Leu Ile Ile Leu Thr
            20                  25                  30

Leu Leu Leu Gly Trp Leu Gly Asn Val Ser Leu Leu Pro Val Leu Val
        35                  40                  45

Val Leu Phe Phe Met Ser Pro Leu Leu Ala Thr Lys Arg Ala Pro
    50                  55                  60

Trp Gln Ser Ile Leu Phe Gly Val Gly Cys Leu Leu Pro Gln Leu Val
65                  70                  75                  80

Gln Phe Val Met Leu Asn Gln Arg
                85

<210> SEQ ID NO 102
<211> LENGTH: 33
<212> TYPE: PRT
<213> ORGANISM: Vibrio cholerae
<220> FEATURE:
<221> NAME/KEY: misc_feature
<223> OTHER INFORMATION: hypothetical protein
<221> NAME/KEY: misc_feature
<223> OTHER INFORMATION: gi[96]57724

<400> SEQUENCE: 102

Met Arg Arg Leu Leu Cys Leu Ser Phe Asn Thr Leu His Leu Asn Gln
1               5                   10                  15

Ile Asn Asp Asn Gln Leu Lys Ser Leu Thr Lys Leu Arg Ile Ile Leu
            20                  25                  30

Asn

<210> SEQ ID NO 103
<211> LENGTH: 34
<212> TYPE: PRT
<213> ORGANISM: Vibrio cholerae
<220> FEATURE:
<221> NAME/KEY: misc_feature
<223> OTHER INFORMATION: hypothetical protein
<221> NAME/KEY: misc_feature
<223> OTHER INFORMATION: gi[96]57931
```

-continued

<400> SEQUENCE: 103

Met Gly Lys Ser Met Pro Ile Gln Leu Leu Leu Ser Ile Pro Phe
1               5                   10                  15

Leu Leu Asp Ala Ala Thr Pro Ser Arg Leu Gly Ile Lys Ile Leu Ile
            20                  25                  30

Leu Lys

<210> SEQ ID NO 104
<211> LENGTH: 36
<212> TYPE: PRT
<213> ORGANISM: Vibrio cholerae
<220> FEATURE:
<221> NAME/KEY: misc_feature
<223> OTHER INFORMATION: hypothetical protein
<221> NAME/KEY: misc_feature
<223> OTHER INFORMATION: gi[96]58035

<400> SEQUENCE: 104

Met Gly Tyr Pro Ser Met Ala Ala Leu His Ala Ala Leu Asn
1               5                   10                  15

Ile Ala Leu Asn Ile Gln Leu Asn Ile Ser Met Arg Ala Met Leu Leu
            20                  25                  30

Ala Phe Leu Glu
        35

<210> SEQ ID NO 105
<211> LENGTH: 38
<212> TYPE: PRT
<213> ORGANISM: Vibrio cholerae
<220> FEATURE:
<221> NAME/KEY: misc_feature
<223> OTHER INFORMATION: hypothetical protein
<221> NAME/KEY: misc_feature
<223> OTHER INFORMATION: gi[96]58254

<400> SEQUENCE: 105

Met Leu Ile Arg Glu Leu Ala Leu Ala Ala Tyr Gln Phe His Arg Tyr
1               5                   10                  15

Phe Lys Ile His Phe Met Phe Gln Phe Lys Val Phe Leu Phe Leu Ala
            20                  25                  30

Lys Gly Phe Phe Ser Phe
        35

<210> SEQ ID NO 106
<211> LENGTH: 35
<212> TYPE: PRT
<213> ORGANISM: Vibrio cholerae
<220> FEATURE:
<221> NAME/KEY: misc_feature
<223> OTHER INFORMATION: hypothetical protein
<221> NAME/KEY: misc_feature
<223> OTHER INFORMATION: gi[96]56580

<400> SEQUENCE: 106

Met Lys Leu Asn Asp Leu Asn Lys Lys Pro Leu Val Ile Lys Lys Thr
1               5                   10                  15

Ala Leu Ser Phe Gln Lys Leu Lys Lys Leu Gln Gln Pro Val Lys Lys
            20                  25                  30

Phe His Phe
        35

<210> SEQ ID NO 107

```
<211> LENGTH: 665
<212> TYPE: PRT
<213> ORGANISM: Plasmodium falciparum
<220> FEATURE:
<221> NAME/KEY: misc_feature
<223> OTHER INFORMATION: hypothetical protein
<221> NAME/KEY: misc_feature
<223> OTHER INFORMATION: gi[38]45248

<400> SEQUENCE: 107

Met Gln Tyr Phe Phe Leu Val Phe Leu Ala Val Leu Ala Lys Gly Phe
1               5                   10                  15

Leu Arg Asn Lys Glu His Ala Asn Leu Ile Asn Ser Tyr Asn Asp Ile
            20                  25                  30

Val Glu Asp Ile Asn Ile Lys Lys Glu Glu Lys Ser Ser Ser Glu Pro
        35                  40                  45

Pro Phe Ile Pro Ile Lys Asn Lys Ile Asp Asn Val His Thr Lys Asn
    50                  55                  60

Asn Asn Gln Tyr Asn Leu His Asn Asn Lys Ser Asn Lys Thr His Leu
65                  70                  75                  80

Thr Tyr Gly Thr His Thr Ser Phe Leu Gln Asn Cys Thr Ile Asn Asp
                85                  90                  95

Cys Val Asp Val Asp Asn Lys Asp Ser Glu Ile Asn Asn Ile Thr Lys
            100                 105                 110

Glu Lys Asp Asp Asn Asn Asn Asn Gly Thr Lys Gln Ile Glu Glu
        115                 120                 125

Lys Asn Lys Ile Asn Lys Ser Asp Leu His Arg Gln Asn Glu Leu Asn
130                 135                 140

Leu Gln Ser Gly Lys Asn Glu Gln Asp Ile Asn Lys Asn Glu Lys Gly
145                 150                 155                 160

Lys Gln Asp Ile Ser Asn Ser Asn Ala Glu Asn Lys Lys Asp Val Lys
                165                 170                 175

Glu Gly Val Lys Glu Leu Glu Glu Lys Lys Glu Glu Lys Ile Ser
            180                 185                 190

Asp Asp His Lys Val Glu Glu Asn Lys Lys Ser Asp Asp His Lys Val
        195                 200                 205

Glu Glu Asn Lys Lys Ser Asp Asp His Lys Val Glu Glu Asn Lys Lys
    210                 215                 220

Ser Asp Asp His Lys Ile Glu Glu Val Lys Lys Val Glu Glu His Glu
225                 230                 235                 240

Glu Asp Glu Glu Glu Asp Lys Lys Glu Lys Ser Gly Asn Lys Asn
                245                 250                 255

Lys Asp Glu Asn Lys Asp Glu Asn Asp Glu Asp Asn Asp Glu Ile Ser
            260                 265                 270

Asp Glu Asp Glu Val Asp Asp Val Glu Glu Asp Lys Asn Glu Asn
        275                 280                 285

Asp Asp Ile Asp Asp Lys Lys Glu Thr Asp Lys Thr His Leu Glu
    290                 295                 300

Glu Glu Glu Asn Glu Ile Ile Glu Lys Glu Phe Ser Asp Lys Lys
305                 310                 315                 320

Asn Gly Lys Asn Lys Asp Thr Lys Glu Lys Ser Lys Asp Thr Glu
                325                 330                 335

Lys Glu Lys Ser Lys Asp Ile Glu Glu Ser Lys Asp Lys Glu
            340                 345                 350

Lys Glu Lys Ser Lys Asp Lys Glu Lys Gly Lys Asp Lys Glu
        355                 360                 365
```

```
Lys Glu Lys Ser Lys Asp Ile Glu Lys Glu Lys Asp Lys Asp
            370                 375                 380

Ile Glu Lys Glu Lys Ser Lys Asp Thr Ala Lys Glu Lys Glu Lys Asp
385                 390                 395                 400

Lys Asp Ile Glu Lys Glu Lys Ser Lys Asp Met Glu Lys Leu Lys Asn
                405                 410                 415

Lys Gln Asn Asp Glu Lys Lys Asp Asp Asn Glu Lys Lys Lys Asn
            420                 425                 430

Asp Lys Gln Asp Ile His Asp Asp Asn Asp Glu Asn Asp Met Glu
            435                 440                 445

Glu Ile Glu Glu Asn Asp Asp Glu Asp Glu Asp Glu Asp Met Glu
        450                 455                 460

Asn Lys Lys Lys Lys Lys Gly Lys Asn Gly Asn Glu Asn Gly Asn
465                 470                 475                 480

Glu Asn Gly Ser Glu Asn Gly Asn Glu Asn Gly Asn Glu Asn Gly Asn
                485                 490                 495

Glu Asn Glu Asn Lys Asn Glu Ser Glu Asn Glu Asn Glu Asn Glu Asn
            500                 505                 510

Glu Asn Glu Asn Gly Asn Glu Asn Glu Asn Glu Lys Glu Asn Glu Lys
            515                 520                 525

Asp Lys Asn Ile Lys Glu Ile Glu Asn Val Thr Asn Ala Asn Lys Glu
530                 535                 540

Asn Tyr Glu Lys Ile Asn Lys Asn Ser Glu Ile Thr Ile Thr Lys Ser
545                 550                 555                 560

Asn Ile Asp Ile Tyr Asn Asn Asn Arg Asn Asn Asp Ile Asp Lys Val
                565                 570                 575

Asn Asn His Ile Phe Thr Asn Gln Gln Lys Lys His Asn Leu His Asn
            580                 585                 590

Glu Gln Asn Lys Phe Asn Glu Thr Leu Asn Val Ser Thr Asn His Lys
        595                 600                 605

Asn His Tyr Glu Glu Lys Lys Lys Tyr Glu Ser Asn Met Phe Asn Val
    610                 615                 620

Asp Lys Arg Met His Lys Asn Leu Thr Ser Met Asp Thr Ile Leu His
625                 630                 635                 640

Asn Leu Asn Asp Lys Leu Ser His His Lys Asp Leu Lys Asn Val Leu
                645                 650                 655

Asn Asp Lys Lys Lys Lys Lys Asn Lys
            660                 665

<210> SEQ ID NO 108
<211> LENGTH: 807
<212> TYPE: PRT
<213> ORGANISM: Plasmodium falciparum
<220> FEATURE:
<221> NAME/KEY: misc_feature
<223> OTHER INFORMATION: hypothetical protein
<221> NAME/KEY: misc_feature
<223> OTHER INFORMATION: gi[38]45292

<400> SEQUENCE: 108

Met Ala Val Glu Ser Lys Pro Asn Asn Ser Lys Glu Lys Asn Glu
1               5                   10                  15

Glu Asn Asp Ile Ile Asn Lys Cys Asp Asp Ser Asn Lys Ile Asn Gly
            20                  25                  30

Lys Glu Asn Ile Phe Ala Val Glu Lys Val Gly Ile Asn Glu Ser Gly
        35                  40                  45
```

-continued

```
His Met Ser Asn Asp Asn Ile Asn Lys Asn Gln Glu Lys Asn Lys Lys
 50                  55                  60

Lys Lys Lys Lys Lys Asn Thr His Lys Lys Val Asn Ile Asn Asn Thr
 65                  70                  75                  80

His Ile Asn Ile His Thr Thr Asn Asp Lys Asn Asn Gly Gln Asp Ile
                 85                  90                  95

Asn Lys Pro Glu Val Ile Glu Arg Asp Asn Ile Asn Ile Lys Asn
            100                 105                 110

Asp Thr Asn Asn Ile Leu Asp Ser Ser Tyr Asn Glu Glu Gly Asn Glu
            115                 120                 125

Asn Asn Arg Asn Asp Ile Asn Asn Asn Asn Asn Asn Asn Asn Ile Asn
        130                 135                 140

Ile Asn Asn Asn Asn Ile Asn Asn Ser Cys Ser Asn Asn Tyr Gly Leu
145                 150                 155                 160

Lys Lys Lys Ile Thr Leu Leu Lys Arg Asn Asp Ile Lys Asp Glu Gly
                165                 170                 175

Tyr Asn Asn Glu Asn Ile Thr Thr Leu Asn Asn Lys Asn Asn Leu Lys
            180                 185                 190

Asn Asn Asn Asn Tyr Asn Asp Asn Arg Asn Asn Asn Asn Asn Lys
        195                 200                 205

Asn Asn Ile Asn Asn Asn Asn Asn Asn Cys Cys Ser Glu Lys Thr
210                 215                 220

Leu Glu Gln Arg Glu Lys Glu Tyr Asn Lys Ile Arg Ala Arg Ile Phe
225                 230                 235                 240

Ser Asn Phe Asn Lys Lys Gln Lys Asn Val Gln Lys Thr Glu Gln Asn
                245                 250                 255

Asn Leu Asn His Thr Tyr Leu Asn Asn Asn Ile Ile Asn Asn Ile Asn
            260                 265                 270

Asn Gly Asp Asn Gln Tyr Ala Tyr Ile Asn Asn Phe Tyr His Ile Tyr
            275                 280                 285

His Asn Asn Ser Tyr Asn His Ile Tyr Arg Gln Asn Asn Ile Pro Ile
        290                 295                 300

Cys Asn Ile Asn Asn His Ala Pro Asn Ile Glu Lys Leu Asn Asn Pro
305                 310                 315                 320

Tyr Tyr Tyr His Asp Asn His Ile Ala Tyr Thr Asn Tyr Met Tyr Ser
                325                 330                 335

Thr Gln Asn Lys Met Asn Asn Met Lys Thr Lys Gln Ile Gly His Tyr
            340                 345                 350

Gly Ile Asn Asn Glu Asp Asn Asn Asn Asn Asn Asn Asn Ile Asn
        355                 360                 365

Asn Asn Asn Asn Asn Ile Asn Asn Asn Ile Asn Asn Asn Asn
    370                 375                 380

Val Pro Leu Cys Ile Pro Gln Leu Asp Asn Tyr Asn Lys Thr Lys Asn
385                 390                 395                 400

Asn Phe Asn Gln Gly Thr Asn Asn Phe Asn Gln Gly Thr Asn Asn Phe
                405                 410                 415

Asn Lys Cys Thr Asn Asn Phe Asn Asn Ala Lys Asn His Ile Lys His
            420                 425                 430

Asn Ile Asn Asn Thr Asn Lys Asn Ile Glu His Leu Asn Asn His Ser
        435                 440                 445

Ile Tyr Asn Phe Val Tyr Pro Glu Asn Lys Asn Ile Tyr Asp Ala Asn
450                 455                 460
```

```
Gly Asn Leu Ile Asn Asn Ile Ser Tyr Thr Gln Leu Lys Met Asn
465                 470                 475                 480

Asn Asn Ile Asn Phe Asn Ile His Met Glu Ser Pro Ile Asn Gln Gln
            485                 490                 495

His Asn Asn Thr Phe Lys Val Asn Asn Asp Thr Asn Phe Phe Asn Glu
        500                 505                 510

Pro Thr Asn Lys Met Lys Lys Lys Asn Lys Glu Lys Lys Asn Ile His
        515                 520                 525

Phe Asn Asn Asn Asn Asn Asn Asn Lys Cys Leu Tyr Lys Asp
530                 535                 540

Ile Asn Gln Asn Asp His Asn Asn Ser Ile Ile Asn Thr Asn Gln Asn
545                 550                 555                 560

Phe Asp His Ile Asn Asn Val Lys Asn Thr Glu Gln Asn Leu Gln Lys
            565                 570                 575

Lys His Asn Lys Met Ser Gln Val Ser Lys Gln Ser Asn Asn Lys Asn
        580                 585                 590

Asn Lys Asn Asn Ser His Leu Lys Lys Gln Ile Asn Ile Asn Thr Asn
        595                 600                 605

Asn Asn Met Asp Asn Lys Asn Asn Ser His Ile Ser Lys Asn Val Ile
610                 615                 620

Val Asp Asp Asn Lys Leu Lys Ser Ser His Ala Asp Asn Ser Asn Glu
625                 630                 635                 640

Ile Val Thr Lys Gly Lys Lys Lys Asn Thr Asn Lys Lys Lys
            645                 650                 655

Ile Asn Asn Ile Asn Ser Val Asn Val Asn Asn Ile Asn Ser Met
            660                 665                 670

Asn Asn Ile Asn Ser Met Asn Ile Ile Ser Met Asn Asn Val Asn
        675                 680                 685

Asn Met Asn Asn Pro Met Tyr Phe Pro Asn Val Asn Ile Gln Lys Asp
690                 695                 700

Asp Ser Asn Ile Ala Leu Leu Tyr Asn Asn Lys Pro Asn Ile Asp Phe
705                 710                 715                 720

Asn Asn Phe Gln Leu Asn His Ile Asn Asn His Met Ile Gln Asn Asn
            725                 730                 735

Ile Met Thr Asn Asn Val Met Leu Asn Asn Leu Thr Thr Ser Asn
            740                 745                 750

Phe Asn Tyr Asn Leu Ile Asn Tyr Ser Tyr Glu Pro Phe Tyr Glu Glu
        755                 760                 765

Asn Leu Met Asn Asp Leu Asp Tyr Cys Arg Asp Ile Ser Leu Tyr Glu
770                 775                 780

Lys Arg Tyr Asp Arg Gly Asp Asn Leu Gln Gln Asn His Lys Arg Tyr
785                 790                 795                 800

Asp Ile Asp Phe Pro Ser Leu
                805

<210> SEQ ID NO 109
<211> LENGTH: 861
<212> TYPE: PRT
<213> ORGANISM: Plasmodium falciparum
<220> FEATURE:
<221> NAME/KEY: misc_feature
<223> OTHER INFORMATION: hypothetical protein
<221> NAME/KEY: misc_feature
<223> OTHER INFORMATION: gi[44]93994

<400> SEQUENCE: 109
```

-continued

```
Met Tyr Glu Leu Leu Leu Arg Phe Leu Lys Tyr Glu Cys Asp Tyr
1               5                   10                  15

Asp Asp Ser Glu Asp Ile Leu Asn Lys Tyr Cys Phe Ile Arg Glu Arg
            20                  25                  30

Lys Tyr Asn Lys Pro Gly Gly Asn Lys Tyr Ile Pro Arg Asp Arg Ser
        35                  40                  45

Asn Asn Asn Asn Asn Ile Gly Asn Asn Val Asn Gly Met Asn Asn Phe
50                  55                  60

Val Leu Leu Asn Asn Asn Asn Asn Met Arg Ile Arg Asn Thr Tyr
65              70                  75                  80

Asn Asn Asn Asn Asn Asn Ile Asn Asn Asn Asn Asn Asn Asn Asn
                85                  90                  95

Asn Phe Asn Asn Phe Asn Asn Asn Asn Asn Asn Asn Phe Asn Asn
            100                 105                 110

Phe Asn Asn Phe Asn Asn Asn Asn Phe Asn Asn Asn Asn His Phe
        115                 120                 125

Asn Ile His Asn Ile Asp Asn Tyr Asp Asp Ser Tyr Val Lys Gly Arg
    130                 135                 140

His Arg Gly Asn Tyr Leu Ser Ser Ser Leu Asn Asn Ile Asn Gly Lys
145                 150                 155                 160

Val Phe Lys Asn Leu Asp Asp Asn Cys Tyr Asn Leu Pro Thr Asn Asn
                165                 170                 175

Leu Tyr Ile Asp Lys Glu Gly Lys Met His Leu Thr Gly Lys Glu His
            180                 185                 190

Tyr Asn Ala Ala Ser Ser Asn Glu Tyr Asn His Asn Asn Lys Asn Thr
        195                 200                 205

Asn Asn Tyr Asn Asn Asn Ser Tyr Asn Asn Asn Phe Cys Asn Asn
210                 215                 220

Asn Tyr Asn Asp Asn Asn Tyr Asn Asn Ser Asn Asn Lys Gly Met Gly
225                 230                 235                 240

Asn Lys Tyr Glu Arg Ser Leu Asn Tyr Leu Lys Lys Glu His Asp Met
                245                 250                 255

Val Asp Tyr Glu Tyr Asn Asn Lys Gly Asn Ile Arg Lys Asn Asp Ser
            260                 265                 270

Glu Lys Tyr Trp Asp Asn Pro Pro Leu His Tyr Ser Lys Lys Asn Asn
        275                 280                 285

Tyr Asp Ile Phe Thr Leu Gly Asp Ile Lys Lys Tyr Ala Lys Asn Asn
    290                 295                 300

Glu Lys Lys Gly Asn Asn Lys Tyr Met Asn Met His Asp Asn Asn Ser
305                 310                 315                 320

Asn Asn Ser Asn Asn Val Leu Asn Asn Asn Met Asn Ser Asn Ser
                325                 330                 335

Asn Asn Tyr Asn Asn Ile Phe Lys Asp Asn Asp Glu Glu Asn Leu Thr
            340                 345                 350

Lys Ser Asn Phe Ala Lys Trp Phe Lys Asn Asn Asn Met Asn Val
        355                 360                 365

Asn Glu Asn Thr Asp Ile Ile Lys Tyr Leu Asn Asn Lys Asn Ser Gln
    370                 375                 380

Gly His Ser Asp Gly Lys Asn Asn Asn Asn Asn Gly Asn Asn Ile
385                 390                 395                 400

Ile Asn Asn Asn Ser Asn Asn Lys Asn Asn Ile Phe Gln Gly Asn Ser
                405                 410                 415

Arg Asn Tyr Glu Asn Val Met Tyr Asn Ile Asn Asn Asn Asn Asn
```

-continued

```
                420                 425                 430
Asn Ile Ile Ser Asn Asn Lys Asn Glu Ala Ser Phe Asn Thr Asp Asn
            435                 440                 445
Ile Asn Thr Asn Ser Gly Arg Glu Glu Lys Ile Ser Asn Thr Val
        450                 455                 460
Ala Glu Leu Leu Met Lys Gln Ile Ser Met Ile Lys Glu Arg Asn Lys
465                 470                 475                 480
Gly Leu Asp Val Leu Glu Lys Lys Asn Thr Phe Gly Phe Leu Asp Asn
                485                 490                 495
Asn Tyr Gln Asn Tyr Gly Ser Asn Asn Ser Ser Leu Glu Lys Asn
            500                 505                 510
Asn Met Lys Glu Asn Asp Ile Tyr Ser Lys Glu Ala Ser Lys Arg Ile
            515                 520                 525
Met Asp Ile Phe Arg Thr Leu Asn Ser Asn Gly Leu Val Ser Gln Glu
            530                 535                 540
Ser Leu Leu Val Asn Gln Ser Val Leu Asn Asn Asn Asn Tyr Asn
545                 550                 555                 560
Asn Tyr Asn Ser Asn Asn Asn Arg Asn Lys Asn Gln Asn Asn Asn
            565                 570                 575
Asn Asn Asn Asn Asn Met Asn Asn Met Asn Asn Ser Asn Asn Asn Ile
            580                 585                 590
Asn Asn Asn Asn Asn Tyr Tyr Lys Asn Asn His Lys Tyr His Ser Met
            595                 600                 605
Asp Asn Val Thr Tyr Lys Lys Ile Phe Ile Asn Asn Tyr Ser Asn Asn
            610                 615                 620
Asp Gly Asn Asn Asn Ser Asn Asn Ser Asn Ser Asn Asn Asn Val Glu
625                 630                 635                 640
His Tyr Tyr Met Asn Asn Lys Lys Asn Phe Lys Asn Lys Ile Asn Asn
            645                 650                 655
Tyr His Asn Leu Pro Asp Asn Lys Asn Asn Met Met Asn Asn Asn Thr
            660                 665                 670
Tyr Asn Asn Ile Asn Lys Asn Asn Leu Ser Asn Met Glu Asn Phe Pro
            675                 680                 685
Pro Ser Leu Ser Phe Asn Asn Ser Asp Ile Asn Lys Asn Asn Ala Gln
            690                 695                 700
Gly Asn Ile Asn Ile Thr Pro Ile Ile Asn Ser Ile Leu Arg Leu Asp
705                 710                 715                 720
Asn Glu Val Asp Asn Val His Asn Asn Ser Ile Ser Glu Asn Ile Gln
                725                 730                 735
Asn Ala Lys Val Ser Asn Val Leu Asp Ser Leu Lys Ser Leu Leu Lys
                740                 745                 750
Ala Ser Lys Ser Gln Gly Asn Asn Tyr Asn Ile Pro Lys Asn Phe
            755                 760                 765
Asn Asn Asn Asn Asn Asn Asn Ser Lys Phe Ile Asn Tyr Asn
            770                 775                 780
Ser Gln Gln Tyr Tyr Pro Ser His Gln Gln Gln Gln His Gln
785                 790                 795                 800
Gln Gln Gln Gln Gln Gln Gln Gln Thr Leu Ile Gln Thr Gln Ile
                805                 810                 815
Asn Ser Thr His Leu Asn Asp Phe Asn Lys Lys Lys Phe Asn Lys Lys
            820                 825                 830
Glu Arg Tyr Pro Met Lys Tyr Pro Glu Phe Asp Gly Thr Thr Asn Glu
            835                 840                 845
```

-continued

```
Thr Met Met Val Arg Glu Lys Ala Glu Arg Gln Leu Val
    850                 855                 860

<210> SEQ ID NO 110
<211> LENGTH: 54
<212> TYPE: PRT
<213> ORGANISM: Plasmodium falciparum
<220> FEATURE:
<221> NAME/KEY: misc_feature
<223> OTHER INFORMATION: Homologue of C.elegans F49C12.11 protein
<221> NAME/KEY: misc_feature
<223> OTHER INFORMATION: gi[44]94004

<400> SEQUENCE: 110

Met Pro Leu Asn Thr Gln Gly Gly Lys Lys Pro Leu Lys Ala Ala
1               5                   10                  15

Lys Lys Gly Pro Val Glu Leu Thr Glu Glu Asp Ile Ala Phe Lys Lys
                20                  25                  30

Glu Met Ala Glu Lys Lys Lys Ala Glu Glu Ala Lys Gln Lys Leu
                35                  40                  45

Leu Lys Ala Lys Lys Lys
        50

<210> SEQ ID NO 111
<211> LENGTH: 71
<212> TYPE: PRT
<213> ORGANISM: L. major
<220> FEATURE:
<221> NAME/KEY: misc_feature
<223> OTHER INFORMATION: hypothetical protein P1105.01
<221> NAME/KEY: misc_feature
<223> OTHER INFORMATION: gi[69]96498

<400> SEQUENCE: 111

Met Arg Glu Arg Leu Ser Thr Asp Glu Tyr Val Tyr Trp Ser Gly Ile
1               5                   10                  15

Leu Leu Pro Leu Ile Arg Val Ile Asp Leu Ala Ser Val Asp Ser Pro
                20                  25                  30

Leu Ala Leu Ala Leu Arg Ala Cys Val Cys Val Cys Val Cys Val Cys
                35                  40                  45

Val Cys Val Cys Val Cys Val Cys Val Val Phe Leu Pro Leu Pro
        50                  55                  60

Ser Leu Arg Ala Gln Ser Pro
65                  70

<210> SEQ ID NO 112
<211> LENGTH: 923
<212> TYPE: PRT
<213> ORGANISM: L. major
<220> FEATURE:
<221> NAME/KEY: misc_feature
<223> OTHER INFORMATION: AC005941_2 L5204.2
<221> NAME/KEY: misc_feature
<223> OTHER INFORMATION: gi[69]78417

<400> SEQUENCE: 112

Met Gln Leu Ser Gln Glu Asp Glu Glu Ala Ile Arg Thr Leu Arg Gly
1               5                   10                  15

Glu Ile Glu Ala Ala Trp Ala Lys Ala Asp Thr Ala His Glu Gln Glu
                20                  25                  30

Gln Arg Ser Arg Glu Leu Leu His Thr Leu Arg Gln Gln Val Thr Glu
                35                  40                  45
```

```
Leu Asp Ala Met Val Glu Lys Thr Ala Gly Leu Ser Met Gly Gln Glu
 50                  55                  60
Ala Tyr Leu Arg Asp Leu Leu Thr Val Lys Lys Asp Arg Glu Glu Glu
 65                  70                  75                  80
Ala Met Leu Leu His Ala Ala Leu Asn Arg Thr Glu Ala Asp His Arg
                 85                  90                  95
Gln Val Cys Val Gln Leu Ala Ala Ala Lys Gln Ala His Glu Ala Ala
            100                 105                 110
Gln Arg Glu Arg Asp Glu Gln Arg Gln Val Tyr Gln His Leu Leu Thr
        115                 120                 125
Ser Leu Glu Ala Glu Gln Arg Glu Arg Ala Ala Lys Glu Ala Ser Val
        130                 135                 140
Arg Gln Tyr Arg Asp Thr Thr Glu Leu Cys Met Arg Arg Leu Asp Glu
145                 150                 155                 160
Arg Gly Val Glu Val Glu Arg Ala Ile Arg Glu Glu Lys Lys Ala Ala
                165                 170                 175
Lys Glu Ala Glu Gly Thr Ala Gln Glu Ile Gln Ala Ile Ala Arg Gln
            180                 185                 190
Leu Gln Glu Arg Gln Glu Arg Phe Gly Val Glu Ala Ala Arg Leu Ala
        195                 200                 205
Ala Ala Glu Arg Glu Asn Thr Ile Leu Thr Arg Glu Leu Pro Gln Arg
    210                 215                 220
Gln Ala Ala Leu His Glu Gln Gln Asp Glu Leu Lys Arg Glu Glu Lys
225                 230                 235                 240
Gln Leu His Leu Leu Glu Lys Ser Ala Arg Ala Gln Gln Ala Glu Leu
                245                 250                 255
Ala Ala Leu Val Glu Lys Arg Ala Thr Ala Ala Ala Val Gln Thr
            260                 265                 270
Arg Ala Asn Ser Val Asp Ala Ala Leu Thr Glu Leu Ala Thr Glu Glu
        275                 280                 285
Lys Ala Arg Ala Ala Leu Glu Glu Ala Val Ala Lys Glu Met Gln Arg
    290                 295                 300
Lys Thr Asn Thr Met His Thr Asn Thr Phe Lys Ala Thr Ala Ser Ser
305                 310                 315                 320
Lys Val Glu Gly Gln Arg Val Met Glu Ala Gly Lys Ser Arg Arg Leu
                325                 330                 335
His Gln Gln Leu Glu Leu Leu Arg Thr Glu Asn Glu Lys Met Arg Lys
            340                 345                 350
Glu Ile Tyr Tyr Ala Glu Gln Asn His Glu Lys Asn Thr Lys Glu Ala
        355                 360                 365
Gln Gln Ala Leu Leu Asn Tyr His Arg Thr Leu Asp Ala Ile Arg Thr
    370                 375                 380
Arg Arg Ser Glu Ala Lys Ala Val Glu Glu Asp Ile Ala Leu His Gln
385                 390                 395                 400
Lys Lys Leu Lys Ala Gln Gln Ala Leu Leu Ser Thr Val Thr Ala Asp
                405                 410                 415
Arg Gln Lys Thr Glu Lys Ala Leu Arg Glu Thr Glu Ala Glu Leu Leu
            420                 425                 430
Leu Leu Arg Asn Arg His Ala Ser Lys Gln Glu Glu Leu Glu Ser Val
        435                 440                 445
Lys Thr Glu Leu Ile Gln Gln Glu Ala Asp Met Cys Gln Leu His Gly
    450                 455                 460
Leu Ser Arg Gln Leu Asn Lys Asp Val Ala Asn Thr Glu Gln Arg Leu
```

```
                465                 470                 475                 480
            Arg Phe Leu Arg Glu Asp Gln Gln His Ala Glu Ser Arg Val Glu Ala
                            485                 490                 495
            Leu Arg Ser Glu Ala Gln Glu Leu Arg Gln Val Ile Ala Gln Tyr Asp
                            500                 505                 510
            Leu Glu Ala Gln Gln Gln Gly Thr Arg Leu Lys Tyr Met Thr His Glu
                            515                 520                 525
            Arg Asn Ala Ile Ala Thr Gln Leu Leu Leu Arg Ser Glu Glu Leu Glu
                            530                 535                 540
            Leu Ile Arg Glu Lys Ile Arg Leu Ala Asp Ala Thr Arg Val Ser Gly
            545                 550                 555                 560
            Thr Thr Lys Tyr Gln Arg Ala Met Lys Gln Leu Leu Glu Ser Arg Asp
                            565                 570                 575
            Leu Leu Val Glu Gln Arg Leu Arg Cys Arg Ile Ala Leu Val Arg Leu
                            580                 585                 590
            Arg Tyr Leu Asp Arg Leu His Thr Lys Glu Val His Gln Glu Lys Leu
                            595                 600                 605
            Leu Ser Gln Ser Arg Ala Arg Val Arg Ala Leu Ala Asp Glu Leu Gly
                            610                 615                 620
            Thr Lys His Asn Val His Cys Trp Arg Ser Met Glu Ser Asn Ala Pro
            625                 630                 635                 640
            Glu Val Leu Asp Ala Leu Ala Lys Val Gln Leu Leu Gln Ala Lys Leu
                            645                 650                 655
            Leu Arg Lys His Gly Glu Leu Lys Glu Lys Thr Asp Leu Val Glu Lys
                            660                 665                 670
            Glu Glu Arg Ala Tyr Gln Gln Leu Arg Gln Lys Leu Ala Arg Met Pro
                            675                 680                 685
            Gly Pro Glu Ala Ala Glu Glu Leu Ala Leu Cys Ala Glu Asn Met Gln
                            690                 695                 700
            Gln Arg Lys Ala Gln Leu Leu Cys Met Thr Asp Ser Leu Ala Glu Ala
            705                 710                 715                 720
            Glu Gln Glu Ala Glu Val Leu Glu Val His Val Ala Gln Leu Gln Glu
                            725                 730                 735
            Glu Leu Gln Asp Leu Lys His Arg Tyr Tyr Gln Glu Lys Thr Lys His
                            740                 745                 750
            Ala Ala Leu Arg Gln Glu Glu Lys Leu Val Ala Arg Thr Trp Gly Ala
                            755                 760                 765
            Gly Gly Ala Gly Ala Ala Arg Gln Ala Gly Ser Gly Thr Gly Ser Ser
                            770                 775                 780
            Val Gly Asp Gly Asp Gly Ala Val Val Ala Ala Gly Ala Ser Ala Pro
            785                 790                 795                 800
            Ser Ala Glu Gln Arg Arg Thr Asn Thr Asp Asp Arg Ser Pro Ser Ala
                            805                 810                 815
            Gly Gly Pro Ala Ser Ala Asp Val Glu His Arg Ser Ala Ser Gln Pro
                            820                 825                 830
            Gln Gln Pro His Ser His Ala Gly Gly Ser Ala Ile Val Ser Asn Ser
                            835                 840                 845
            His Asn Gly Val Gln Ala Ala Ser Gly Thr Gly Arg Met Ser Ala
                            850                 855                 860
            Ala Asn Ser Gly Arg Val Gly Asn Gly Ser Val Pro Pro Arg Asn Gly
            865                 870                 875                 880
            Arg Arg Arg Ala Pro Leu Ala Glu Ala Ile Leu Asp Thr Leu Thr Ala
                            885                 890                 895
```

Gly Pro Pro Gln Pro Asn Phe Pro Leu Gln Arg Pro Pro His Gln Arg
                900                 905                 910

Gln Phe Val Gly Gly Gly Phe Ser Leu Thr Arg
            915                 920

<210> SEQ ID NO 113
<211> LENGTH: 2354
<212> TYPE: PRT
<213> ORGANISM: L. major
<220> FEATURE:
<221> NAME/KEY: misc_feature
<223> OTHER INFORMATION: AC005802_5 L6202.3
<221> NAME/KEY: misc_feature
<223> OTHER INFORMATION: gi[68]99670

<400> SEQUENCE: 113

Met Ser Thr Pro Val Ser Gly Val Val Pro Gln Asp Arg Trp Gln Pro
1               5                   10                  15

Gln Gln Arg Val Lys Val Cys Gln Tyr Gln Asp Cys Gly Ala Pro Phe
            20                  25                  30

Gly Phe Phe Ser Thr Lys Val Asn Cys His Arg Cys Gly Ile Val Leu
        35                  40                  45

Cys Ser Lys Cys Ala Ala Thr Lys Thr Val Ile Pro Arg Tyr Tyr Ser
50                  55                  60

Asn Glu Thr Val Pro Val Cys Gln Arg Cys Tyr Gln Val Val Glu Arg
65                  70                  75                  80

Tyr Lys Glu Arg Gly Ser Val Thr Pro Gly Tyr Val Val His Ser Thr
                85                  90                  95

Thr Ile Ser Ala Thr Pro Ala Arg Ser Ser Pro Val Pro Pro Leu His
            100                 105                 110

Thr Thr Pro Ala Leu Arg Pro His Ala Pro Ser Pro Gln Pro Ala Ser
        115                 120                 125

Val Val Ser Thr Ala Thr Leu Val His Pro Val Glu Glu Asp Ala Val
130                 135                 140

Ser Thr Lys Pro Ser Val Ser Glu Ala Asp Leu His Ala Leu Arg Ser
145                 150                 155                 160

Ile Ile Glu Thr Leu Gln Gln Ala Leu Asn Asp Glu Gln His Asn Ala
                165                 170                 175

Ala Leu Ala Ala Thr Ser Ala Ala Glu Gln Leu Arg Thr Ala Lys Glu
            180                 185                 190

Glu Asn Thr Ala Leu Lys Ser Thr Ala His Leu Gln Gln Arg Leu
        195                 200                 205

Asp Thr Ala Thr Gln Gln Arg Ala Glu Leu Glu Ala Arg Val Ala Arg
210                 215                 220

Leu Ala Ala Asp Arg Asp Glu Ala Arg Gln Gln Leu Ala Ala Asn Ala
225                 230                 235                 240

Glu Glu Leu Gln Gln Arg Leu Asp Thr Ala Thr Gln Gln Arg Ala Glu
                245                 250                 255

Leu Glu Ala Arg Val Ala Arg Leu Ala Ala Asp Arg Asp Glu Ala Arg
            260                 265                 270

Gln Gln Leu Ala Ala Asn Ala Glu Glu Leu Gln Gln Arg Leu Asp Thr
        275                 280                 285

Ala Thr Gln Gln Arg Ala Glu Leu Glu Ala Gln Val Ala Arg Leu Ala
    290                 295                 300

Ala Asp Gly Asp Glu Ala Arg Gln Gln Leu Ala Ala Asn Ala Glu Glu
305                 310                 315                 320

-continued

```
Leu Gln Gln Arg Leu Asp Thr Ala Thr Gln Gln Arg Ala Glu Leu Glu
                325                 330                 335

Ala Arg Val Ala Arg Leu Ala Ala Asp Arg Asp Glu Ala Arg Gln Gln
            340                 345                 350

Leu Ala Ala Asn Ala Glu Glu Leu Gln Gln Arg Leu Asp Thr Ala Thr
        355                 360                 365

Gln Gln Arg Ala Glu Leu Glu Ala Gln Leu Ala Arg Leu Ala Ala Asp
    370                 375                 380

Arg Asp Glu Ala Arg Gln Gln Leu Ala Ala Asn Ala Glu Glu Leu Gln
385                 390                 395                 400

Gln Arg Leu Asp Thr Ala Thr Gln Gln Arg Ala Glu Leu Glu Ala Gln
            405                 410                 415

Val Ala Arg Leu Ala Ala Asn Ala Glu Glu Leu Gln Gln Arg Leu Asp
        420                 425                 430

Thr Ala Thr Gln Gln Arg Ala Glu Leu Glu Ala Arg Val Ala Arg Leu
    435                 440                 445

Ala Ala Asp Arg Asp Glu Ala Arg Gln Gln Leu Ala Ala Asn Ala Glu
    450                 455                 460

Glu Leu Gln Gln Arg Leu Asp Thr Ala Thr Gln Gln Arg Ala Glu Leu
465                 470                 475                 480

Glu Ala Arg Val Ala Arg Leu Ala Ala Asp Gly Asp Glu Ala Arg Gln
            485                 490                 495

Gln Leu Ala Ala Asn Ala Glu Glu Leu Gln Gln Arg Leu Asp Thr Ala
        500                 505                 510

Thr Gln Gln Arg Ala Glu Leu Glu Ala Gln Val Ala Arg Leu Ala Ala
    515                 520                 525

Asn Ala Glu Glu Leu Gln Gln Arg Leu Asp Thr Ala Thr Gln Gln Arg
    530                 535                 540

Ala Glu Leu Glu Ala Arg Val Ala Arg Leu Ala Ala Asp Arg Asp Glu
545                 550                 555                 560

Ala Arg Gln Gln Leu Ala Ala Asn Ala Glu Glu Leu Gln Gln Arg Leu
            565                 570                 575

Asp Thr Ala Thr Gln Gln Arg Ala Glu Leu Glu Ala Gln Val Ala Arg
        580                 585                 590

Leu Ala Ala Asn Ala Glu Glu Leu Gln Gln Arg Leu Asp Thr Ala Thr
    595                 600                 605

Gln Gln Arg Ala Glu Leu Glu Ala Arg Val Ala Arg Leu Ala Val Asp
    610                 615                 620

Arg Asp Glu Ala Arg Gln Gln Leu Ala Ala Asn Ala Glu Glu Leu Gln
625                 630                 635                 640

Gln Arg Leu Asp Thr Ala Thr Gln Gln Arg Ala Glu Leu Glu Ala Gln
            645                 650                 655

Val Ala Arg Leu Ala Ala Asp Arg Asp Glu Ala Arg Gln Gln Leu Ala
        660                 665                 670

Ala Asn Ala Glu Glu Leu Gln Gln Arg Leu Asp Thr Ala Thr Gln Gln
    675                 680                 685

Arg Ala Glu Leu Glu Ala Gln Leu Ala Arg Leu Ala Ala Asp Arg Asp
    690                 695                 700

Glu Ala Arg Gln Gln Leu Ala Ala Asn Ala Glu Glu Leu Gln Gln Arg
705                 710                 715                 720

Leu Asp Thr Ala Thr Gln Gln Arg Ala Glu Leu Glu Ala Gln Val Ala
            725                 730                 735
```

-continued

```
Arg Leu Ala Ala Asp Arg Asp Glu Ala Arg Gln Gln Leu Ala Ala Asn
                740                 745                 750

Ala Glu Glu Leu Gln Gln Arg Leu Asp Thr Ala Thr Gln Gln Arg Ala
        755                 760                 765

Glu Leu Glu Ala Gln Leu Ala Arg Leu Ala Ala Asp Arg Asp Glu Ala
        770                 775                 780

Arg Gln Gln Leu Ala Ala Asn Ala Glu Leu Gln Gln Arg Leu Asp
785                 790                 795                 800

Thr Ala Thr Gln Gln Arg Ala Glu Leu Glu Ala Gln Val Ala Arg Leu
            805                 810                 815

Ala Ala Asp Arg Asp Glu Ala Arg Gln Gln Leu Ala Ala Asn Ala Glu
            820                 825                 830

Glu Leu Gln Gln Arg Leu Asp Thr Ala Thr Gln Gln Arg Ala Glu Leu
            835                 840                 845

Glu Ala Gln Val Ala Arg Leu Ala Ala Asp Arg Asp Glu Ala Arg Gln
            850                 855                 860

Gln Leu Ala Ala Asn Ala Glu Glu Leu Gln Gln Arg Leu Asp Thr Ala
865                 870                 875                 880

Thr Gln Gln Arg Ala Glu Leu Glu Ala Gln Val Ala Arg Leu Ala Ala
                885                 890                 895

Asn Ala Glu Glu Leu Gln Gln Arg Leu Asp Thr Ala Thr Gln Gln Arg
            900                 905                 910

Ala Glu Leu Glu Ala Arg Val Ala Arg Leu Ala Ala Asp Arg Asp Glu
            915                 920                 925

Ala Arg Gln Gln Leu Ala Ala Asn Ala Glu Glu Leu Gln Gln Arg Leu
            930                 935                 940

Asp Thr Ala Thr Gln Gln Arg Ala Glu Leu Glu Ala Gln Leu Ala Arg
945                 950                 955                 960

Leu Ala Ala Asp Arg Asp Glu Ala Arg Gln Gln Leu Ala Ala Asn Ala
                965                 970                 975

Glu Glu Leu Gln Gln Arg Leu Asp Thr Ala Thr Gln Gln Arg Ala Glu
            980                 985                 990

Leu Glu Ala Gln Leu Ala Arg Leu Ala Ala Asp Arg Asp Glu Ala Arg
            995                1000                1005

Gln Gln Leu Ala Ala Asn Ala Glu Glu Leu Gln Gln Arg Leu Asp
        1010                1015                1020

Thr Ala Thr Gln Gln Arg Ala Glu Leu Glu Ala Gln Val Ala Arg
        1025                1030                1035

Leu Ala Ala Asp Arg Asp Glu Ala Arg Gln Gln Leu Ala Ala Asn
        1040                1045                1050

Ala Glu Glu Leu Gln Gln Arg Leu Asp Thr Ala Thr Gln Gln Arg
        1055                1060                1065

Ala Glu Leu Glu Ala Arg Val Ala Arg Leu Ala Ala Asp Arg Asp
        1070                1075                1080

Glu Ala Arg Gln Gln Leu Ala Ala Asn Ala Glu Glu Leu Gln Gln
        1085                1090                1095

Arg Leu Asp Thr Ala Thr Gln Gln Arg Ala Glu Leu Glu Ala Gln
        1100                1105                1110

Val Ala Arg Leu Ala Ala Asp Gly Asp Glu Ala Arg Gln Gln Leu
        1115                1120                1125

Ala Ala Asn Ala Glu Glu Leu Gln Gln Arg Leu Asp Thr Ala Thr
        1130                1135                1140

Gln Gln Arg Ala Glu Leu Glu Ala Arg Val Ala Arg Leu Ala Ala
```

```
                1145                1150                1155

Asp Arg Asp Glu Ala Arg Gln Gln Leu Ala Ala Asn Ala Glu Glu
        1160                1165                1170

Leu Gln Gln Arg Leu Asp Thr Ala Thr Gln Gln Arg Ala Glu Leu
        1175                1180                1185

Glu Ala Gln Leu Ala Arg Leu Ala Ala Asp Arg Asp Glu Ala Arg
        1190                1195                1200

Gln Gln Leu Ala Ala Asn Ala Glu Glu Leu Gln Gln Arg Leu Asp
        1205                1210                1215

Thr Ala Thr Gln Gln Arg Ala Glu Leu Glu Ala Gln Val Ala Arg
        1220                1225                1230

Leu Ala Ala Asp Gly Asp Glu Ala Arg Gln Gln Leu Ala Ala Asn
        1235                1240                1245

Ala Glu Glu Leu Gln Gln Arg Leu Asp Thr Ala Thr Gln Gln Arg
        1250                1255                1260

Ala Glu Leu Glu Ala Gln Leu Ala Arg Leu Ala Ala Asp Arg Asp
        1265                1270                1275

Glu Ala Arg Gln Gln Leu Ala Ala Asn Ala Glu Glu Leu Gln Gln
        1280                1285                1290

Arg Leu Asp Thr Ala Thr Gln Gln Arg Ala Glu Leu Glu Ala Gln
        1295                1300                1305

Val Ala Arg Leu Ala Ala Asn Ala Glu Glu Leu Gln Gln Arg Leu
        1310                1315                1320

Asp Thr Ala Thr Gln Gln Arg Ala Glu Leu Glu Ala Arg Val Ala
        1325                1330                1335

Arg Leu Ala Ala Asp Arg Asp Glu Ala Arg Gln Gln Leu Ala Ala
        1340                1345                1350

Asn Ala Glu Glu Leu Gln Gln Arg Leu Asp Thr Ala Thr Gln Gln
        1355                1360                1365

Arg Ala Glu Leu Glu Ala Arg Val Ala Arg Leu Ala Ala Asp Arg
        1370                1375                1380

Asp Glu Ala Arg Gln Gln Leu Ala Ala Asn Ala Glu Glu Leu Gln
        1385                1390                1395

Gln Arg Leu Asp Thr Ala Thr Gln Gln Arg Ala Glu Leu Glu Ala
        1400                1405                1410

Gln Val Ala Arg Leu Ala Ala Asn Ala Glu Glu Leu Gln Gln Arg
        1415                1420                1425

Leu Asp Thr Ala Thr Gln Gln Arg Ala Glu Leu Glu Ala Arg Val
        1430                1435                1440

Ala Arg Leu Ala Ala Asp Arg Asp Glu Ala Arg Gln Gln Leu Ala
        1445                1450                1455

Ala Asn Ala Glu Glu Leu Gln Gln Arg Leu Asp Thr Ala Thr Gln
        1460                1465                1470

Gln Arg Ala Glu Leu Glu Ala Gln Val Ala Arg Leu Ala Ala Asp
        1475                1480                1485

Arg Asp Glu Ala Arg Gln Gln Leu Ala Ala Asn Ala Glu Glu Leu
        1490                1495                1500

Gln Gln Arg Leu Asp Thr Ala Thr Gln Gln Arg Ala Glu Leu Glu
        1505                1510                1515

Ala Arg Val Ala Arg Leu Ala Ala Asp Gly Asp Glu Ala Arg Gln
        1520                1525                1530

Gln Leu Ala Ala Asn Ala Glu Glu Leu Gln Gln Arg Leu Asp Thr
        1535                1540                1545
```

```
Ala Thr Gln Gln Arg Ala Glu Leu Glu Ala Gln Leu Ala Arg Leu
    1550            1555                1560

Ala Ala Asp Arg Asp Glu Ala Arg Gln Gln Leu Ala Ala Asn Ala
    1565            1570                1575

Glu Glu Leu Gln Gln Arg Leu Asp Thr Ala Thr Gln Gln Arg Ala
    1580            1585                1590

Glu Leu Glu Ala Arg Val Ala Arg Leu Ala Ala Asp Gly Asp Glu
    1595            1600                1605

Ala Arg Gln Gln Leu Ala Ala Asn Ala Glu Glu Leu Gln Gln Arg
    1610            1615                1620

Leu Asp Thr Ala Thr Gln Gln Arg Ala Glu Leu Glu Ala Arg Val
    1625            1630                1635

Ala Arg Leu Ala Ala Asp Arg Asp Glu Ala Arg Gln Gln Leu Ala
    1640            1645                1650

Ala Asn Ala Glu Glu Leu Gln Gln Arg Leu Asp Thr Ala Thr Gln
    1655            1660                1665

Gln Arg Ala Glu Leu Glu Ala Gln Leu Ala Arg Leu Ala Ala Asp
    1670            1675                1680

Arg Asp Glu Ala Arg Gln Gln Leu Ala Ala Asn Ala Glu Glu Leu
    1685            1690                1695

Gln Gln Arg Leu Asp Thr Ala Thr Gln Gln Arg Ala Glu Leu Glu
    1700            1705                1710

Ala Gln Leu Ala Arg Leu Ala Ala Asp Gly Asp Glu Ala Arg Gln
    1715            1720                1725

Gln Leu Ala Ala Asn Ala Glu Glu Leu Gln Gln Arg Leu Asp Thr
    1730            1735                1740

Ala Thr Gln Gln Arg Ala Glu Leu Glu Val Glu Met Ala Val Leu
    1745            1750                1755

Leu Arg Glu Arg Glu Ala Arg Gly Glu Thr Ala Val Ala Gly
    1760            1765                1770

Glu Gln Val Gln Leu Tyr Arg Glu Thr Val Glu Glu Glu Glu Cys
    1775            1780                1785

Leu Lys Glu Glu Arg Trp Cys Leu Glu Ser Arg Val Ala Gln Leu
    1790            1795                1800

Arg Glu Ala Ser Ala Ala Ala Lys Gln Gln Arg Gln Glu Val Ala
    1805            1810                1815

Ala Lys Ala Asn Glu Val Gln Glu Arg Leu Asp Ser Met Ala Arg
    1820            1825                1830

Arg Cys Ile Ala His Glu Gly Asp Ala Pro Gln Arg Ala Asp Gly
    1835            1840                1845

Arg Asp Asp Ala Leu Arg Gln Leu Ala Asn Leu Arg Glu Glu Val
    1850            1855                1860

Lys Leu Ser Glu Lys Gln Lys Ala Met Glu Arg Val Ile Pro Gly
    1865            1870                1875

Val Arg Glu Arg Gln Met Arg Leu Glu Ala Ala Glu Glu Gln Arg
    1880            1885                1890

Ala Asp Leu Glu Ala Arg Leu Val Asp Glu Ala Gly Asp Leu Arg
    1895            1900                1905

Ser Arg Pro Ala Ala Ser Thr Asn Glu Val Asn Leu Tyr Arg Asp
    1910            1915                1920

Leu Ala Leu Gln Glu His Glu Ala Ala Gln Asn Arg Cys Thr Thr
    1925            1930                1935
```

-continued

```
Leu Glu Ala Gln Val Ala Ser Leu Thr Ser Asp Arg Asp Asn Gly
    1940                1945                1950

Arg Gln Gln Glu Ser Ala Asp Leu Ser Glu Ala Gln Arg His Leu
    1955                1960                1965

Asp Asn Val Gln Glu Arg Asp Met Ala His Arg Cys Ala Ala
    1970                1975                1980

Leu Glu Glu Gln Asn Ala Ala Met Ala Ser Glu Leu Gln Ala Val
    1985                1990                1995

Lys Ala Lys Leu Arg Gln Ala Ser Val Lys Ala Ser Ser Leu Met
    2000                2005                2010

Thr Arg Leu Ser Ala Ser Ser Ser Gly Ala Gly Gly Val Ser Ala
    2015                2020                2025

Arg Val Arg Val Gly Gly Ser Ser Ala Val Pro Gln Ala Ala Pro
    2030                2035                2040

His Arg Asp Ala Glu Leu Ile Ala Glu Val Gly Glu Arg Leu Arg
    2045                2050                2055

Glu Arg Gly Glu Ala Met Arg Leu Leu Ala Glu Gly Val Glu Leu
    2060                2065                2070

Arg Glu Arg Ala Arg Pro Leu Glu Arg Val Leu Ala Glu Lys Leu
    2075                2080                2085

Ile Gly Asp Arg Arg Thr Ser Asp Ala Glu Glu Val Ala Thr Glu
    2090                2095                2100

Pro Thr Gln Val Arg Arg Asn Ala Ala His Ser Arg His Leu Asp
    2105                2110                2115

Ser Arg Glu Ala Gln Leu Asp Glu Arg Ala Ala Arg Leu Arg Glu
    2120                2125                2130

Lys Glu Gln Gln Leu Leu Arg Val Ala Arg Glu Leu Gln Thr Lys
    2135                2140                2145

Ser Arg Ala Leu Gln Val Leu Tyr Ala Arg Ala Leu Asn Arg Pro
    2150                2155                2160

Gln Val Thr Ser Leu Leu Leu Thr Ala Asp Gly Asp Asp Thr Ser
    2165                2170                2175

Tyr Pro Asp Thr Pro Gln Gln Gln Gln Gln Gly Thr Arg Thr Pro
    2180                2185                2190

Leu Arg Glu Pro Val Tyr Ser Leu Asp Ser Glu Val Ala His Tyr
    2195                2200                2205

Gly Arg Thr Ala Gly Ala Ala Val Ser Ser Gly Leu Ala Ser Pro
    2210                2215                2220

Leu Pro Arg Glu Pro Pro Arg Ala Arg Met Val His Arg Ala Val
    2225                2230                2235

Glu Ala Thr Gly Thr Glu Glu Asp Thr Gln Val Arg Leu Thr Ala
    2240                2245                2250

Ala Thr Glu Ala Tyr Arg Asp Val Leu Tyr Glu His Ile Leu Glu
    2255                2260                2265

Ser Asn Gly Leu Gln Gly Val Asp Val Leu Ala Gln Tyr Leu Pro
    2270                2275                2280

His His Thr Ser Gly Gly Gly Leu Lys Thr Pro Arg Leu Pro Gly
    2285                2290                2295

Ser Gly Ile Ile Ser Lys Thr Arg Ala Met Leu Arg Ala Leu Glu
    2300                2305                2310

Glu Arg Leu Gly Ala Ser Arg Gly Val Gly Arg Gly Val Asp Pro
    2315                2320                2325

Ala Val Gln Glu Arg Ser Leu Glu Ala Phe Arg Arg Leu Glu Ala
```

-continued

```
           2330                2335                2340
Ala Leu  Ser Ala Leu Cys Gly  Gly Ser His Ala
    2345                2350

<210> SEQ ID NO 114
<211> LENGTH: 2310
<212> TYPE: PRT
<213> ORGANISM: L. major
<220> FEATURE:
<221> NAME/KEY: misc_feature
<223> OTHER INFORMATION: AC005893_12 L6202.3
<221> NAME/KEY: misc_feature
<223> OTHER INFORMATION: gi[68]99664

<400> SEQUENCE: 114

Met Ser Thr Pro Val Ser Gly Val Val Pro Gln Asp Arg Trp Gln Pro
1               5                   10                  15

Gln Gln Arg Val Lys Val Cys Gln Tyr Gln Asp Cys Gly Ala Pro Phe
            20                  25                  30

Gly Phe Phe Ser Thr Lys Val Asn Cys His Arg Cys Gly Ile Val Leu
        35                  40                  45

Cys Ser Lys Cys Ala Ala Thr Lys Thr Val Ile Pro Arg Tyr Tyr Ser
50                  55                  60

Asn Glu Thr Val Pro Val Cys Gln Arg Cys Tyr Gln Val Val Glu Arg
65                  70                  75                  80

Tyr Lys Glu Arg Gly Ser Val Thr Pro Gly Tyr Val Val His Ser Thr
                85                  90                  95

Thr Ile Ser Ala Thr Pro Ala Arg Ser Ser Pro Val Pro Pro Leu His
            100                 105                 110

Thr Thr Pro Ala Leu Arg Pro His Ala Pro Ser Pro Gln Pro Ala Ser
        115                 120                 125

Val Val Ser Thr Ala Thr Leu Val His Pro Val Glu Glu Asp Ala Val
130                 135                 140

Ser Thr Lys Pro Ser Val Ser Glu Ala Asp Leu His Ala Leu Arg Ser
145                 150                 155                 160

Ile Ile Glu Thr Leu Gln Gln Ala Leu Asn Asp Glu Gln His Asn Ala
                165                 170                 175

Ala Leu Ala Ala Thr Ser Ala Ala Glu Gln Leu Arg Thr Ala Lys Glu
            180                 185                 190

Glu Asn Thr Ala Leu Lys Ser Thr Ala His Leu Leu Gln Gln Arg Leu
        195                 200                 205

Asp Thr Ala Thr Gln Gln Arg Ala Glu Leu Glu Ala Gln Val Ala Arg
    210                 215                 220

Leu Ala Ala Asp Arg Asp Glu Arg Gln Gln Leu Ala Ala Asn Ala
225                 230                 235                 240

Glu Glu Leu Gln Gln Arg Leu Asp Thr Ala Thr Gln Gln Arg Ala Glu
                245                 250                 255

Leu Glu Ala Arg Val Ala Arg Leu Ala Ala Asp Arg Asp Glu Ala Arg
            260                 265                 270

Gln Gln Leu Ala Ala Asn Ala Glu Glu Leu Gln Gln Arg Leu Asp Thr
        275                 280                 285

Ala Thr Gln Gln Arg Ala Glu Leu Glu Ala Gln Val Ala Arg Leu Ala
    290                 295                 300

Ala Asn Ala Glu Glu Leu Gln Gln Arg Leu Asp Thr Ala Thr Gln Gln
305                 310                 315                 320

Arg Ala Glu Leu Glu Ala Gln Leu Ala Arg Leu Ala Ala Asp Arg Asp
```

-continued

```
                325                 330                 335
Glu Ala Arg Gln Gln Leu Ala Ala Asn Ala Glu Leu Gln Gln Arg
            340                 345                 350

Leu Asp Thr Ala Thr Gln Gln Arg Ala Glu Leu Glu Ala Gln Val Ala
            355                 360                 365

Arg Leu Ala Ala Asn Ala Glu Glu Leu Gln Gln Arg Leu Asp Thr Ala
            370                 375                 380

Thr Gln Gln Arg Ala Glu Leu Glu Ala Arg Val Ala Arg Leu Ala Ala
385                 390                 395                 400

Asp Arg Asp Glu Ala Arg Gln Gln Leu Ala Ala Asn Ala Glu Glu Leu
                405                 410                 415

Gln Gln Arg Leu Asp Thr Ala Thr Gln Gln Arg Ala Glu Leu Glu Ala
            420                 425                 430

Gln Val Ala Arg Leu Ala Ala Asn Arg Asp Glu Ala Arg Gln Gln Leu
            435                 440                 445

Ala Ala Asn Ala Glu Glu Leu Gln Gln Arg Leu Asp Thr Ala Thr Gln
            450                 455                 460

Gln Arg Ala Glu Leu Glu Ala Gln Val Ala Arg Leu Ala Ala Asp Arg
465                 470                 475                 480

Asp Glu Ala Arg Gln Gln Leu Ala Ala Asn Ala Glu Glu Leu Gln Gln
                485                 490                 495

Arg Leu Asp Thr Ala Thr Gln Gln Arg Ala Glu Leu Glu Ala Arg Val
            500                 505                 510

Ala Arg Leu Ala Ala Asp Arg Asp Glu Ala Arg Gln Gln Leu Ala Ala
            515                 520                 525

Asn Ala Glu Glu Leu Gln Gln Arg Leu Asp Thr Ala Thr Gln Gln Arg
            530                 535                 540

Ala Glu Leu Glu Ala Arg Val Ala Arg Leu Ala Ala Asn Ala Glu Glu
545                 550                 555                 560

Leu Gln Gln Arg Leu Asp Thr Ala Thr Gln Gln Arg Ala Glu Leu Glu
                565                 570                 575

Ala Gln Val Ala Arg Leu Ala Ala Asn Ala Glu Glu Leu Gln Gln Arg
            580                 585                 590

Leu Asp Thr Ala Thr Gln Gln Arg Ala Glu Leu Glu Ala Arg Val Ala
            595                 600                 605

Arg Leu Ala Ala Asp Arg Asp Glu Ala Arg Gln Gln Leu Ala Ala Asn
            610                 615                 620

Ala Glu Glu Leu Gln Gln Arg Leu Asp Thr Ala Thr Gln Gln Arg Ala
625                 630                 635                 640

Glu Leu Glu Ala Gln Leu Ala Arg Leu Ala Ala Asp Gly Asp Glu Ala
                645                 650                 655

Arg Gln Gln Leu Ala Ala Asn Ala Glu Glu Leu Gln Gln Arg Leu Asp
            660                 665                 670

Thr Ala Thr Gln Gln Arg Ala Glu Leu Glu Ala Arg Val Ala Arg Leu
            675                 680                 685

Ala Ala Asp Arg Asp Glu Ala Arg Gln Gln Leu Ala Ala Asn Ala Glu
            690                 695                 700

Glu Leu Gln Gln Arg Leu Asp Thr Ala Thr Gln Gln Arg Ala Glu Leu
705                 710                 715                 720

Glu Ala Gln Leu Ala Arg Leu Ala Ala Asp Arg Asp Glu Ala Arg Gln
                725                 730                 735

Gln Leu Ala Ala Asn Ala Glu Glu Leu Gln Gln Arg Leu Asp Thr Ala
            740                 745                 750
```

-continued

```
Thr Gln Gln Arg Ala Glu Leu Glu Ala Arg Val Ala Arg Leu Ala Ala
        755                 760                 765

Asp Gly Asp Glu Ala Arg Gln Gln Leu Ala Ala Asn Ala Glu Glu Leu
        770                 775                 780

Gln Gln Arg Leu Asp Thr Ala Thr Gln Gln Arg Ala Glu Leu Glu Ala
785                 790                 795                 800

Arg Val Ala Arg Leu Ala Ala Asp Arg Asp Glu Ala Arg Gln Gln Leu
                805                 810                 815

Ala Ala Asn Ala Glu Glu Leu Gln Gln Arg Leu Asp Thr Ala Thr Gln
            820                 825                 830

Gln Arg Ala Glu Leu Glu Ala Gln Leu Ala Arg Leu Ala Ala Asp Gly
        835                 840                 845

Asp Glu Ala Arg Gln Gln Leu Ala Ala Asn Ala Glu Glu Leu Gln Gln
        850                 855                 860

Arg Leu Asp Thr Ala Thr Gln Gln Arg Ala Glu Leu Glu Ala Arg Val
865                 870                 875                 880

Ala Arg Leu Ala Ala Asp Arg Asp Glu Ala Arg Gln Gln Leu Ala Ala
                885                 890                 895

Asn Ala Glu Glu Leu Gln Gln Arg Leu Asp Thr Ala Thr Gln Gln Arg
            900                 905                 910

Ala Glu Leu Glu Ala Gln Leu Ala Arg Leu Ala Ala Asp Arg Asp Glu
        915                 920                 925

Ala Arg Gln Gln Leu Ala Ala Asn Ala Glu Glu Leu Gln Gln Arg Leu
        930                 935                 940

Asp Thr Ala Thr Gln Gln Arg Ala Glu Leu Glu Ala Gln Val Ala Arg
945                 950                 955                 960

Leu Ala Ala Asp Gly Asp Glu Ala Arg Gln Gln Leu Ala Ala Asn Ala
                965                 970                 975

Glu Glu Leu Gln Gln Arg Leu Asp Thr Ala Thr Gln Gln Arg Ala Glu
            980                 985                 990

Leu Glu Ala Gln Leu Ala Arg Leu Ala Ala Asp Arg Asp Glu Ala Arg
        995                 1000                1005

Gln Gln Leu Ala Ala Asn Ala Glu Glu Leu Gln Gln Arg Leu Asp
    1010                1015                1020

Thr Ala Thr Gln Gln Arg Ala Glu Leu Glu Ala Gln Val Ala Arg
    1025                1030                1035

Leu Ala Ala Asn Ala Glu Glu Leu Gln Gln Arg Leu Asp Thr Ala
    1040                1045                1050

Thr Gln Gln Arg Ala Glu Leu Glu Ala Arg Val Ala Arg Leu Ala
    1055                1060                1065

Ala Asp Arg Asp Glu Ala Arg Gln Gln Leu Ala Ala Asn Ala Glu
    1070                1075                1080

Glu Leu Gln Gln Arg Leu Asp Thr Ala Thr Gln Gln Arg Ala Glu
    1085                1090                1095

Leu Glu Ala Arg Val Ala Arg Leu Ala Ala Asn Ala Glu Glu Leu
    1100                1105                1110

Gln Gln Arg Leu Asp Thr Ala Thr Gln Gln Arg Ala Glu Leu Glu
    1115                1120                1125

Ala Gln Val Ala Arg Leu Ala Ala Asn Ala Glu Glu Leu Gln Gln
    1130                1135                1140

Arg Leu Asp Thr Ala Thr Gln Gln Arg Ala Glu Leu Glu Ala Arg
    1145                1150                1155
```

-continued

```
Val Ala Arg Leu Ala Ala Asp Arg Asp Glu Ala Arg Gln Gln Leu
1160                1165                1170

Ala Ala Asn Ala Glu Glu Leu Gln Gln Arg Leu Asp Thr Ala Thr
1175                1180                1185

Gln Gln Arg Ala Glu Leu Glu Ala Gln Val Ala Arg Leu Ala Ala
1190                1195                1200

Asn Ala Glu Glu Leu Gln Gln Arg Leu Asp Thr Ala Thr Gln Gln
1205                1210                1215

Arg Ala Glu Leu Glu Ala Gln Leu Ala Arg Leu Ala Ala Asp Arg
1220                1225                1230

Asp Glu Ala Arg Gln Gln Leu Ala Ala Asn Ala Glu Glu Leu Gln
1235                1240                1245

Gln Arg Leu Asp Thr Ala Thr Gln Gln Arg Ala Glu Leu Glu Ala
1250                1255                1260

Gln Val Ala Arg Leu Ala Ala Asn Ala Glu Glu Leu Gln Gln Arg
1265                1270                1275

Leu Asp Thr Ala Thr Gln Gln Arg Ala Glu Leu Glu Ala Arg Val
1280                1285                1290

Ala Arg Leu Ala Ala Asp Arg Asp Glu Ala Arg Gln Gln Leu Ala
1295                1300                1305

Ala Asn Ala Glu Glu Leu Gln Gln Arg Leu Asp Thr Ala Thr Gln
1310                1315                1320

Gln Arg Ala Glu Leu Glu Ala Arg Val Ala Arg Leu Ala Ala Asp
1325                1330                1335

Gly Asp Glu Ala Arg Gln Gln Leu Ala Ala Asn Ala Glu Glu Leu
1340                1345                1350

Gln Gln Arg Leu Asp Thr Ala Thr Gln Gln Arg Ala Glu Leu Glu
1355                1360                1365

Ala Gln Val Ala Arg Leu Ala Ala Asn Ala Glu Glu Leu Gln Gln
1370                1375                1380

Arg Leu Asp Thr Ala Thr Gln Gln Arg Ala Glu Leu Glu Ala Arg
1385                1390                1395

Val Ala Arg Leu Ala Ala Asp Arg Asp Glu Ala Arg Gln Gln Leu
1400                1405                1410

Ala Ala Asn Ala Glu Glu Leu Gln Gln Arg Leu Asp Thr Ala Thr
1415                1420                1425

Gln Gln Arg Ala Glu Leu Glu Ala Gln Val Ala Arg Leu Ala Ala
1430                1435                1440

Asp Arg Asp Glu Ala Arg Gln Gln Leu Ala Ala Asn Ala Glu Glu
1445                1450                1455

Leu Gln Gln Arg Leu Asp Thr Ala Thr Gln Gln Arg Ala Glu Leu
1460                1465                1470

Glu Ala Arg Val Ala Arg Leu Ala Ala Asp Gly Asp Glu Ala Arg
1475                1480                1485

Gln Gln Leu Ala Ala Asn Ala Glu Glu Leu Gln Gln Arg Leu Asp
1490                1495                1500

Thr Ala Thr Gln Gln Arg Ala Glu Leu Glu Ala Gln Leu Ala Arg
1505                1510                1515

Leu Ala Ala Asp Arg Asp Glu Ala Arg Gln Gln Leu Ala Ala Asn
1520                1525                1530

Ala Glu Glu Leu Gln Gln Arg Leu Asp Thr Ala Thr Gln Gln Arg
1535                1540                1545

Ala Glu Leu Glu Ala Arg Val Ala Arg Leu Ala Ala Asp Gly Asp
```

-continued

|      |      |      |
|------|------|------|
| 1550 | 1555 | 1560 |

Glu Ala Arg Gln Gln Leu Ala Ala Asn Ala Glu Glu Leu Gln Gln
1565                1570                1575

Arg Leu Asp Thr Ala Thr Gln Gln Arg Ala Glu Leu Glu Ala Arg
1580                1585                1590

Val Ala Arg Leu Ala Ala Asp Arg Asp Glu Ala Arg Gln Gln Leu
1595                1600                1605

Ala Ala Asn Ala Glu Glu Leu Gln Gln Arg Leu Asp Thr Ala Thr
1610                1615                1620

Gln Gln Arg Ala Glu Leu Glu Ala Gln Leu Ala Arg Leu Ala Ala
1625                1630                1635

Asp Arg Asp Glu Ala Arg Gln Gln Leu Ala Ala Asn Ala Glu Glu
1640                1645                1650

Leu Gln Gln Arg Leu Asp Thr Ala Thr Gln Gln Arg Ala Glu Leu
1655                1660                1665

Glu Ala Gln Leu Ala Arg Leu Ala Ala Asp Gly Asp Glu Ala Arg
1670                1675                1680

Gln Gln Leu Ala Ala Asn Ala Glu Glu Leu Gln Gln Arg Leu Asp
1685                1690                1695

Thr Ala Thr Gln Gln Arg Ala Glu Leu Glu Val Glu Met Ala Val
1700                1705                1710

Leu Leu Arg Glu Arg Glu Glu Ala Arg Gly Glu Thr Ala Val Ala
1715                1720                1725

Gly Glu Gln Val Gln Leu Tyr Arg Glu Thr Val Glu Glu Glu
1730                1735                1740

Cys Leu Lys Glu Glu Arg Trp Cys Leu Glu Ser Arg Val Ala Gln
1745                1750                1755

Leu Arg Glu Ala Ser Ala Ala Lys Gln Gln Arg Gln Glu Val
1760                1765                1770

Ala Ala Lys Ala Asn Glu Val Gln Glu Arg Leu Asp Ser Met Ala
1775                1780                1785

Arg Arg Cys Ile Ala His Glu Gly Asp Ala Pro Gln Arg Ala Asp
1790                1795                1800

Gly Arg Asp Asp Ala Leu Arg Gln Leu Ala Asn Leu Arg Glu Glu
1805                1810                1815

Val Lys Leu Ser Glu Lys Gln Lys Ala Met Glu Arg Val Ile Pro
1820                1825                1830

Gly Val Arg Glu Arg Gln Met Arg Leu Glu Ala Ala Glu Glu Gln
1835                1840                1845

Arg Ala Asp Leu Glu Ala Arg Leu Val Asp Glu Ala Gly Asp Leu
1850                1855                1860

Arg Ser Arg Pro Ala Ala Ser Thr Asn Glu Val Asn Leu Tyr Arg
1865                1870                1875

Asp Leu Ala Leu Gln Glu His Glu Ala Ala Gln Asn Arg Cys Thr
1880                1885                1890

Thr Leu Glu Ala Gln Val Ala Ser Leu Thr Ser Asp Arg Asp Asn
1895                1900                1905

Gly Arg Gln Gln Glu Ser Ala Asp Leu Ser Glu Ala Gln Arg His
1910                1915                1920

Leu Asp Asn Val Gln Glu Arg Asp Met Ala His His Arg Cys Ala
1925                1930                1935

Ala Leu Glu Glu Gln Asn Ala Ala Met Ala Ser Glu Leu Gln Ala
1940                1945                1950

Val Lys Ala Lys Leu Arg Gln Ala Ser Val Lys Ala Ser Ser Leu
1955                1960                1965

Met Thr Arg Leu Ser Ala Ser Ser Ser Gly Ala Gly Gly Val Ser
1970                1975                1980

Ala Arg Val Arg Val Gly Gly Ser Ser Ala Val Pro Gln Ala Ala
1985                1990                1995

Pro His Arg Asp Ala Glu Leu Ile Ala Glu Val Gly Glu Arg Leu
2000                2005                2010

Arg Glu Arg Gly Glu Ala Met Arg Leu Leu Ala Glu Gly Val Glu
2015                2020                2025

Leu Arg Glu Arg Ala Arg Pro Leu Glu Arg Val Leu Ala Glu Lys
2030                2035                2040

Leu Ile Gly Asp Arg Arg Thr Ser Asp Ala Glu Glu Val Ala Thr
2045                2050                2055

Glu Pro Thr Gln Val Arg Arg Asn Ala Ala His Ser Arg His Leu
2060                2065                2070

Asp Ser Arg Glu Ala Gln Leu Asp Glu Arg Ala Ala Arg Leu Arg
2075                2080                2085

Glu Lys Glu Gln Gln Leu Leu Arg Val Ala Arg Glu Leu Gln Thr
2090                2095                2100

Lys Ser Arg Ala Leu Gln Val Leu Tyr Ala Arg Ala Leu Asn Arg
2105                2110                2115

Pro Gln Val Thr Ser Leu Leu Leu Thr Ala Asp Gly Asp Asp Thr
2120                2125                2130

Ser Tyr Pro Asp Thr Pro Gln Gln Gln Gln Gly Thr Arg Thr
2135                2140                2145

Pro Leu Arg Glu Pro Val Tyr Ser Leu Asp Ser Glu Val Ala His
2150                2155                2160

Tyr Gly Arg Thr Ala Gly Ala Ala Val Ser Ser Gly Leu Ala Ser
2165                2170                2175

Pro Leu Pro Arg Glu Pro Pro Arg Ala Arg Met Val His Arg Ala
2180                2185                2190

Val Glu Ala Thr Gly Thr Glu Glu Asp Thr Gln Val Arg Leu Thr
2195                2200                2205

Ala Ala Thr Glu Ala Tyr Arg Asp Val Leu Tyr Glu His Ile Leu
2210                2215                2220

Glu Ser Asn Gly Leu Gln Gly Val Asp Val Leu Ala Gln Tyr Leu
2225                2230                2235

Pro His His Thr Ser Gly Gly Gly Leu Lys Thr Pro Arg Leu Pro
2240                2245                2250

Gly Ser Gly Ile Ile Ser Lys Thr Arg Ala Met Leu Arg Ala Leu
2255                2260                2265

Glu Glu Arg Leu Gly Ala Ser Arg Gly Val Gly Arg Gly Val Asp
2270                2275                2280

Pro Ala Val Gln Glu Arg Ser Leu Glu Ala Phe Arg Arg Leu Glu
2285                2290                2295

Ala Ala Leu Ser Ala Leu Cys Gly Gly Ser His Ala
2300                2305                2310

<210> SEQ ID NO 115
<211> LENGTH: 125
<212> TYPE: PRT
<213> ORGANISM: L. major
<220> FEATURE:

```
<221> NAME/KEY: misc_feature
<223> OTHER INFORMATION: hypothetical protein L7276.03
<221> NAME/KEY: misc_feature
<223> OTHER INFORMATION: gi[65]62665

<400> SEQUENCE: 115

Met Asn Ser Ala Asp Ala Leu Glu Pro Ile Pro Arg Ser Ile Ala Pro
1               5                   10                  15

Asp Gln Glu Leu Ser Ile Leu Lys Leu Ile Leu Asp Leu Arg Ser Leu
            20                  25                  30

Gly Asp Val Glu Gly Ser Lys Lys Val Arg Arg Val Arg Glu Ala
        35                  40                  45

Leu Leu Lys Ser Ser Asp Asp Ser Glu Ala Met Ser Lys Val Asp Asp
50                  55                  60

Ile Ile Arg Arg Gly Lys Arg Thr Gln Ser Lys Leu Asp Gly Ser Tyr
65                  70                  75                  80

Asp Glu Arg Gln Arg Leu Lys Arg Lys Arg Glu Glu Asp Leu Ala
                85                  90                  95

Ala Ala Ser Arg Leu Val Asp Val Glu Ala Gly Ser Gly Glu Asp Ser
            100                 105                 110

Glu Gly Ser Ala Ser Thr Glu Glu Asp Gly Thr Glu Asp
        115                 120                 125

<210> SEQ ID NO 116
<211> LENGTH: 57
<212> TYPE: PRT
<213> ORGANISM: L. major
<220> FEATURE:
<221> NAME/KEY: misc_feature
<223> OTHER INFORMATION: hypothetical protein P1105.12
<221> NAME/KEY: misc_feature
<223> OTHER INFORMATION: gi[69]96509

<400> SEQUENCE: 116

Gln Pro Asn Asp Leu Ile Glu Ala Leu Asn Gly Thr Arg Val Arg Asn
1               5                   10                  15

Val Gly Asp Phe Arg Arg Val Ile Glu Glu Leu Thr Pro Gly Met
            20                  25                  30

Ile Val Pro Val Arg Ile Asn Arg Gly Gly Val Ala Met Val Val Thr
        35                  40                  45

Val Arg Val Glu Ala Gly Arg Ser Leu
50                  55

<210> SEQ ID NO 117
<211> LENGTH: 94
<212> TYPE: PRT
<213> ORGANISM: L. major
<220> FEATURE:
<221> NAME/KEY: misc_feature
<223> OTHER INFORMATION: hypothetical protein L2743.10
<221> NAME/KEY: misc_feature
<223> OTHER INFORMATION: gi[64]33946

<400> SEQUENCE: 117

Met Ile Ser Val Asp Leu His His His Lys Thr Arg Ile Glu Met His
1               5                   10                  15

Val Lys Ala Cys Asn Asp Arg Ser His Arg His Thr His Thr His Thr
            20                  25                  30

His Thr Asn Ser Phe Val Ser Gly Asp Val Phe His Val Trp Arg Val
        35                  40                  45

Arg Ser Phe His Ser Ala Pro Ser Val Phe Phe Cys Phe Ser Val Cys
```

-continued

```
                50                  55                  60
Thr His Leu Leu Phe Ser Pro Ser Ser Pro Tyr Ala His His Ala Arg
 65                  70                  75                  80

Val Cys Val Arg Ala Cys Val Cys Val Cys Val Cys Val Val
                 85                  90
```

<210> SEQ ID NO 118
<211> LENGTH: 121
<212> TYPE: PRT
<213> ORGANISM: L. major
<220> FEATURE:
<221> NAME/KEY: misc_feature
<223> OTHER INFORMATION: hypothetical protein L2719.11
<221> NAME/KEY: misc_feature
<223> OTHER INFORMATION: gi[58]69911

<400> SEQUENCE: 118

```
Met Ile Ser Leu Met Leu Leu Ala Ala Leu Leu Trp Gly Val Thr Asn
 1               5                   10                  15

Pro Leu Leu Lys His Tyr Ser Arg Gly Met Ala Ser Ser Gly Ser Ala
                 20                  25                  30

Lys Asp Asp Ala Leu Phe Leu Val Arg Arg Pro Lys Tyr Leu Val Ala
             35                  40                  45

Gln Ala Val Asn Leu Ser Gly Ser Val Val Phe Phe His Ser Leu Arg
         50                  55                  60

Glu Val Asp Val Ser Val Gly Ser Ile Val Val Asn Ser Leu Ala Phe
 65                  70                  75                  80

Val Ile Thr Val Leu Met Ser Val Leu Val Leu Arg Glu Gly Leu Leu
                 85                  90                  95

Arg Ala Arg Thr Thr Ala Gly Cys Leu Leu Val Met Val Gly Thr Ala
                100                 105                 110

Leu Cys Thr Tyr Ser Ser Ser Ala Ser
             115                 120
```